United States Patent
Iwata et al.

(10) Patent No.: US 9,873,695 B2
(45) Date of Patent: Jan. 23, 2018

(54) SERINE DERIVATIVES AS GHRELIN RECEPTOR AGONISTS

(71) Applicant: RaQualia Pharma Inc., Aichi (JP)

(72) Inventors: Yasuhiro Iwata, Aichi (JP); Kiyoshi Kawamura, Aichi (JP); Masaki Sudo, Aichi (JP); Kaoru Shimada, Aichi (JP); Shinichi Koizumi, Aichi (JP); Nobuyuki Takahashi, Aichi (JP); Keiko Obata, Aichi (JP); Makiko Kuroda, Aichi (JP)

(73) Assignee: RaQualia Pharma Inc., Aichi (JP)

( * ) Notice: Subject to any disclaimer, the term of this patent is extended or adjusted under 35 U.S.C. 154(b) by 0 days.

(21) Appl. No.: 15/316,543

(22) PCT Filed: Aug. 5, 2015

(86) PCT No.: PCT/JP2015/003939
§ 371 (c)(1),
(2) Date: Dec. 6, 2016

(87) PCT Pub. No.: WO2016/021191
PCT Pub. Date: Feb. 11, 2016

(65) Prior Publication Data
US 2017/0197961 A1    Jul. 13, 2017

Related U.S. Application Data

(60) Provisional application No. 62/033,369, filed on Aug. 5, 2014.

(51) Int. Cl.
| | |
|---|---|
| C07D 401/14 | (2006.01) |
| A61K 31/437 | (2006.01) |
| C07D 471/04 | (2006.01) |
| C07K 5/062 | (2006.01) |
| G01N 33/68 | (2006.01) |

(52) U.S. Cl.
CPC .......... *C07D 471/04* (2013.01); *A61K 31/437* (2013.01); *C07K 5/06034* (2013.01); *G01N 33/6893* (2013.01); *G01N 2333/575* (2013.01)

(58) Field of Classification Search
CPC .......................... C07D 401/14; A61K 31/437
USPC .......................................... 546/119; 514/303
See application file for complete search history.

(56) References Cited

U.S. PATENT DOCUMENTS 6,448,263 B1 * 9/2002 Carpino ................ A61K 38/05
                                                              514/303

FOREIGN PATENT DOCUMENTS

| EP | 1 132 388 | 9/2001 |
| WO | 97/24369 | * 7/1997 |

OTHER PUBLICATIONS

Extended European Search Report dated Feb. 13, 2017 in corresponding European Application No. 15830440.2.
International Search Report dated Nov. 2, 2015 in International Application No. PCT/JP2015/003939.
Written Opinion of the International Searching Authority dated Nov. 2, 2015 in International Application No. PCT/JP2015/003939.
Japanese Petition dated Mar. 7, 2016 in International Application No. PCT/JP2015/003939, with English translation.
Japanese Office Action dated Aug. 2, 2016 in corresponding Japanese patent application No. 2016-512151, with English translation.
Philip A. Carpino, et al., "Pyrazolirtone-piperidine Dipeptide Growth Hormone Secretagogues (GHSs): Discovery of Capromorelin", Bioorganic & Medicinal Chemistry, vol. 11, pp. 581-590, 2003.
Christine Delporte, "Structure and Physiological Actions of Ghrelin", Scientifica, vol. 2013, pp. 1-25, 2013.
Scientifica 2013, Article ID 518909 (http://dx.doi.org/10.1155/2013/518909), 25 pages, 2013.
Jose M. Garcia et al., "Effect on Body Weight and Safety of RC-1291, a Novel, Orally Available Ghrelin Mimetic and Growth Hormone Secretagogue: Results of a Phase I, Randomized, Placebo-Controlled, Multiple-Dose Study in Healthy Volunteers", The Oncologist 12, pp. 594-600, 2007.
R. Northrup et al., "Effect of ghrelin and anamorelin (ONO-7643), a selective ghrelin receptor agonist, on tumor growth in a lung cancer mouse xenograft model", Support Care Cancer 21, pp. 2409-2415, 2013.
G.J. Sanger et al., "Development of drugs for gastrointestinal motor disorders: translating science to clinical need", Neurogastroenterol Motil 20, pp. 177-184, 2008.
José M. Garcia et al., "Ghrelin Prevents Cisplatin-Induced Mechanical Hyperalgesia and Cachexia", Endocrinology 149, pp. 455-460, 2008.

(Continued)

*Primary Examiner* — Niloofar Rahmani
(74) *Attorney, Agent, or Firm* — Wenderoth, Lind & Ponack, L.L.P.

(57) ABSTRACT

The present invention relates to novel compounds of formula (I) or a pharmaceutically acceptable salt or solvate thereof, processes for their preparation, pharmaceutical compositions containing them and their use in therapy, for example as modulators of the growth hormone secretagogue receptor (also referred to as the ghrelin receptor or GHSR1a receptor) and/or for the treatment and/or prophylaxis of a disorder mediated by the ghrelin receptor.

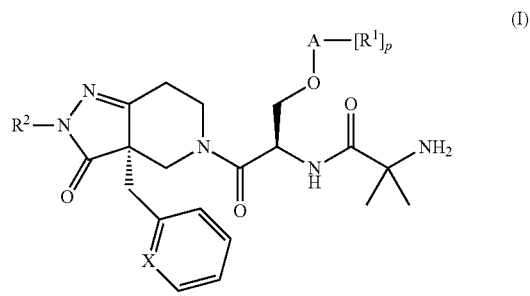

(I)

16 Claims, No Drawings

(56) References Cited

OTHER PUBLICATIONS

Keisuke Miki et al., "Effects of Ghrelin Treatment on Exercise Capacity in Underweight COPD Patients: a substudy of a multicenter, randomized, double-blind, placebo-controlled trial of ghrelin treatment", BMC Pulmonary Medicine 13, pp. 37-46, 2013.

Nobuhiro Matsumoto et al., "Clinical Application of Ghrelin for Chronic Respiratory Diseases", Methods in Enzymology 514, pp. 399-407, 2012.

Markus S. Anker et al., "Highlights of mechanistic and therapeutic cachexia and sarcopenia research 2010 to 2012 and their relevance for cardiology", Arch Med Sci 9, pp. 166-171, 2013.

Mathieu Méquinion et al., "Ghrelin: central and peripheral implications in anorexia nervosa", Frontiers in Endocrinology 4, pp. 1-27, 2013.

Ralf Nass, M.D. et al., "Effects of an Oral Ghrelin Mimetic on Body Composition and Clinical Outcomes in Healthy Older Adults: A Randomized, Controlled Trial", Ann Intern Med 149, pp. 601-611, 2008.

Shuji Takiguchi et al., "Clinical application of ghrelin administration for gastric cancer patients undergoing gastrectomy", Gastric Cancer 17, pp. 200-205, 2014.

Konstantinos Karmiris et al., "Leptin, adiponectin, resistin, and ghrelin-Implications for inflammatory bowel disease", Mol Nutr Food Res 52, pp. 855-866, 2008.

N. Ejskjaer et al., "A phase 2a, randomized, double-blind 28-day study of TZP-102 a ghrelin receptor agonist for diabetic gastroparesis", Neurogastroenterol Motil 25, pp. e140-e150, 2013.

Ichiro Kishimoto (MD, PhD), et al., "Ghrelin and cardiovascular diseases", Journal of Cardiology 59, pp. 8-13, 2012.

Geetali Pradhan et al., "Ghrelin: much more than a hunger hormone", Curr Opin Clin Nutr Metab Care 16, pp. 619-624, 2013.

Daryl O. Schwenke et al., "One Dose of Ghrelin Prevents the Acute and Sustained Increase in Cardiac Sympathetic Tone after Myocardial Infarction", Endocrinology 153, pp. 2436-2443, 2012.

Itaru Kyoraku et al., "Ghrelin reverses experimental diabetic neuropathy in mice", Biochemical and Biophysical Research Communications 389, pp. 405-408, 2009.

Elli Markaki et al., "The Role of Ghrelin, Neuropeptide Y and Leptin Peptides in Weight Gain after Deep Brain Stimulation for Parkinson's Disease", Stereotact Funct Neurosurg 90, pp. 104-112, 2012.

Elham Eftekhari et al., "The relation between peptide hormones and sex hormone in patients with multiple sclerosis", Ir J Neurol 12, pp. 60-65, 2013.

Michael Ankersen et al., "Growth hormone secretagogues: recent advances and applications", Drug Discovery Today 4, pp. 497-506, 1999.

A.D. Shafton et al., "Oral administration of a centrally acting ghrelin receptor agonist to conscious rats triggers defecation", Neurogastroenterol Motil 21, pp. 71-77, 2009.

Pierre Poitras et al., "Gastrokinetic effect of ghrelin analog RC-1139 in the rat-Effect on post-operative and on morphine induced ileus", Peptides 26, pp. 1598-1601, 2005.

Hotta et al., "Ghrelin Increases Hunger and Food Intake in Patients with Restricting-type Anorexia Nervosa: A Pilot Study", Endocrine Journal, vol. 56, No. 9: pp. 1119-1128 (2009).

Akamizu et al., "Ghrelin for cachexia", J Cachexia Sarcopenia Muscle, vol. 1: pp. 169-176 (2010).

* cited by examiner

SERINE DERIVATIVES AS GHRELIN RECEPTOR AGONISTS

TECHNICAL FIELD

The present invention relates to novel serine derivatives, processes for their preparation, intermediates usable in these processes, and pharmaceutical compositions containing the compounds. The invention also relates to the use of the serine derivatives in therapy, for example as modulators of the growth hormone secretagogue receptor (also referred to as the ghrelin receptor or GHSRIa receptor) and/or for the treatment and/or prophylaxis of cancer anorexia/cachexia; cachexia and anorexia by anti-cancer drugs; hyperalgesia by anti-cancer drugs; COPD (chronic obstructive pulmonary disease)/COPD cachexia; sarcopenia; eating disorders and neurological eating disorders; weight loss suppression; early postoperative recovery of cancer patients; chronic respiratory tract infection; inflammation; IBD (inflammatory bowel disease); FD (functional-dyspepsia); constipation; diabetic gastroparesis and gastroparesis; heart failure; myocardial infarction; diabetic neuropathy; Parkinson's disease; multiple sclerosis; diagnosis and treatment of growth hormone deficiency; elderly QOL (quality of life) improvement; bowel movement disturbance of spinal cord injury patients; postoperative ileus; and morphine induced ileus.

BACKGROUND ART

Ghrelin is the endogenous ligand for the growth hormone (GH) secretagogue receptor. It was originally purified from stomach and is a 28 amino acid peptide hormone in which the serine at position 3 is n-octanoylated. It has potent GH releasing activity and thus is believed to play an important role in maintaining GH release and energy homeostasis (NPL 1). In particular, it appears to exert potent appetite-stimulating activities. Then it has been known that a ghrelin agonist is useful for the treatment and/or prophylaxis of cancer anorexia/cachexia (NPL 2, 3 and 4); cachexia and anorexia by anti-cancer drugs (NPL 4 and 5); hyperalgesia by anti-cancer drugs (NPL 5); COPD/COPD cachexia (NPL 6 and 7); sarcopenia (NPL 8); eating disorders and neurological eating disorders (NPL 9); weight loss suppression (NPL 10); early postoperative recovery of cancer patients (NPL 11); chronic respiratory tract infection (NPL 7); inflammation (NPL 12); IBD (NPL 12); FD (NPL 4); constipation (NPL 9); diabetic gastroparesis and gastroparesis (NPL 4 and 13); heart failure (NPL 14, 15 and 16); myocardial infarction (NPL 14, 15 and 16); diabetic neuropathy (NPL 17); Parkinson's disease (NPL 18); multiple sclerosis (NPL 19); diagnosis and treatment of growth hormone deficiency (NPL 20); elderly QOL improvement (NPL 20); bowel movement disturbance of spinal cord injury patients (NPL 21); postoperative ileus (NPL 4 and 22); and morphine induced ileus (NPL 22).

CITATION LIST

Non Patent Literature

{NPL 1} Scientifica 2013, Article ID 518909 (http://dx.doi.org/10.1155/2013/518909), 25 pages, 2013
{NPL 2} The Oncologist 12, 594-600, 2007.
{NPL 3} Support Care Cancer 21, 2409-2415, 2013
{NPL 4} Neurogastroenterol Motil 20, 177-184, 2008
{NPL 5} Endocrinology 149, 455-460, 2008
{NPL 6} BMC Pulmonary Medicine 13, 37-46, 2013
{NPL 7} Methods in Enzymology 514, 399-407, 2012
{NPL 8} Arch Med Sci 9, 166-171, 2013
{NPL 9} Frontiers in Endocrinology 4, 1-27, 2013
{NPL 10} Ann intern Med 149, 601-611, 2008
{NPL 11} Gastric Cancer 17, 200-205, 2014
{NPL 12} Mol Nutr Food Res 52, 855-866, 2008
{NPL 13} Neurogastroenterol Motil 25, e140-e150, 2013
{NPL 14} Journal of Cardiology 59, 8-13, 2012
{NPL 15} Curr Opin Clin Nutr Metab Care 16, 619-624, 2013
{NPL 16} Endocrinology 153, 2436-2443, 2012
{NPL 17} Biochemical and Biophysical Research Communications 389, 405-408, 2009
{NPL 18} Stereotact Funct Neurosurg 90, 104-112, 2012
{NPL 19} Ir J neurol 12, 60-65, 2013
{NPL 20} Drug Discovery Today 4, 497-506, 1999
{NPL 21} Neurogastroenterol Motil 21, 71-77, 2009
{NPL 22} Peptides 26, 1598-1601, 2005

SUMMARY OF INVENTION

Technical Problem

It is therefore desirable to find new compounds which modulate ghrelin receptor activity.

Solution to Problem

[1] This invention provides a compound of the following formula (I):

[Chem. 1]

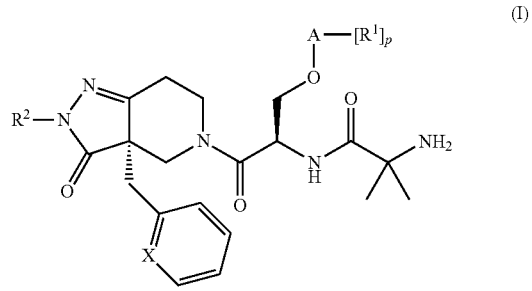

Wherein:
A is aryl; preferable aryl is phenyl, naphtyl, or pyridyl; more preferable aryl is phenyl or pyridyl; the most preferable A is phenyl, 2-pyridyl or 3-pyridyl;
X is CH or N;
$R^1$ is independently selected from the group consisting of (1) hydrogen, (2) halogen, (3) $C_{1-6}$ alkyl, where the alkyl is unsubstituted or substituted with one or more substituents independently selected from halogen, hydroxy, —O—$C_{1-6}$ alkyl, amino, $C_{1-6}$ alkylamino, and ($C_{1-6}$ alkyl) ($C_{1-6}$ alkyl)N—, (4) —O—$C_{1-6}$alkyl, where the alkyl is unsubstituted or substituted with one or more substituents independently selected from halogen, hydroxy, —O—$C_{1-6}$ alkyl, amino, $C_{1-6}$ alkylamino, and ($C_{1-6}$ alkyl) ($C_{1-6}$ alkyl)N—, (5) —CN and (6) —SO$_2$$C_{1-6}$ alkyl; preferable $R^1$ is independently selected from the group consisting of; (1) hydrogen, (2) halogen, (3) trifluoromethyl, (4) trifluoromethoxy, and (5) —CN; more preferable $R^1$ is independently selected from the group consisting of; (1) hydrogen, (2) —F, (3) —Cl, (4) trifluoromethyl, (5) trifluoromethoxy, and (6) —CN;

R² is hydrogen or C₁₋₆ alkyl, where the alkyl is unsubstituted or substituted with one or more substituents independently selected from halogen, hydroxy, —O—C₁₋₆ alkyl, amino, C₁₋₆ alkylamino, and (C₁₋₆ alkyl)(C₁₋₆ alkyl)N—; preferable R² is C₁₋₆ alkyl, where the alkyl is unsubstituted or substituted with one to three substituents independently selected from halogen; more preferable R² is methyl or difluoroethyl; the most preferable R² is methyl or 2,2-difluoroethyl;

p is 1, 2, 3, or 4; when p is two or more than two, R¹ may be same or different;

preferable p is 1 or 2;

or a pharmaceutically acceptable salt thereof.

[2] This invention provides a compound represented by above formula (I) according to [1]
wherein:
A is phenyl, naphtyl, or pyridyl;
or a pharmaceutically acceptable salt thereof.

[3] This invention provides a compound represented by above formula (I) according to [1] or [2]
wherein:
A is phenyl, naphtyl, or pyridyl;
R² is hydrogen or C₁-C₆ alkyl, where the alkyl is unsubstituted or substituted with one to three substituents independently selected from halogen;
or a pharmaceutically acceptable salt thereof.

[4] This invention provides a compound represented by above formula (I) according to any one of [1] to [3]
wherein:
A is phenyl, naphtyl, or pyridyl;
R¹ is independently selected from the group consisting of; (1) hydrogen, (2) halogen, (3) trifluoromethyl, (4) trifluoromethoxy, (5) —CN and (6) —SO₂C₁₋₆ alkyl;
R² is C₁₋₆ alkyl, where the alkyl is unsubstituted or substituted with one to three substituents independently selected from halogen;
or a pharmaceutically acceptable salt thereof.

[5] This invention provides a compound represented by above formula (I) according to any one of [1] to [4]
wherein:
A is phenyl, naphtyl, or pyridyl;
R¹ is independently selected from the group consisting of; (1) hydrogen, (2) —F, (3) —Cl (4) trifluoromethyl, (5) trifluoromethoxy, (6) —CN and (7) —SO₂CH₃;
R² is methyl or difluoroethyl;
or a pharmaceutically acceptable salt thereof.

[6] The compound represented by above formula (I) according to any one of [1] to [5].
wherein:
A is phenyl, 2-pyridyl or 3-pyridyl;
R¹ is independently selected from the group consisting of; (1) hydrogen, (2) —F, (3) —Cl (4) trifluoromethyl, (5) trifluoromethoxy and (6) —CN;
R² is methyl or 2,2-difluoroethyl;
or a pharmaceutically acceptable salt thereof.

[7] Suitable individual compounds of the invention are:

2-amino-N—((R)-1-((R)-3a-benzyl-2-methyl-3-oxo-3a,4,6,7-tetrahydro-2H-pyrazolo[4,3-c]pyridin-5(3H)-yl)-3-(2,4-difluorophenoxy)-1-oxopropan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-3-phenoxypropan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-3-(4-chlorophenoxy)-1-oxopropan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-3-(3-chlorophenoxy)-1-oxopropan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-3-(3,5-dichlorophenoxy)-1-oxopropan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-3-(2-(trifluoromethyl)phenoxy)propan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-3-(3,4-difluorophenoxy)-1-oxopropan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-3-(2-chlorophenoxy)-1-oxopropan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-3-(3,5-bis(trifluoromethyl)phenoxy)-1-oxopropan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-3-(3-fluorophenoxy)-1-oxopropan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-3-(3-methoxyphenoxy)-1-oxopropan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-3-(2-fluorophenoxy)-1-oxopropan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-3-(naphthalen-2-yloxy)-1-oxopropan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-3-(naphthalen-1-yloxy)-1-oxopropan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-3-((5-chloropyridin-3-yl)oxy)-1-oxopropan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-3-(3-cyanophenoxy)-1-oxopropan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-3-(pyridin-2-yloxy)propan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-3-((5-fluoropyridin-3-yl)oxy)-1-oxopropan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-3-((6-(trifluoromethyl)pyridin-2-yl)oxy)propan-2-yl)-2-methylpropanamide;

2-amino-N—((R)-1-((R)-3a-benzyl-2-methyl-3-oxo-3a,4,6,
7-tetrahydro-2H-pyrazolo[4,3-c]pyridin-5(3H)-yl)-3-(4-
cyanophenoxy)-1-oxopropan-2-yl)-2-methylpropana-
mide;
2-amino-N—((R)-1-((R)-3a-benzyl-2-(2,2-difluoroethyl)-3-
oxo-3a,4,6,7-tetrahydro-2H-pyrazolo[4,3-c]pyridin-5
(3H)-yl)-1-oxo-3-phenoxypropan-2-yl)-2-methylpro-
panamide;
2-amino-N—((R)-1-((R)-2-(2,2-difluoroethyl)-3-oxo-3a-
(pyridin-2-ylmethyl)-3a,4,6,7-tetrahydro-2H-pyrazolo[4,
3-c]pyridin-5(3H)-yl)-1-oxo-3-phenoxypropan-2-yl)-2-
methylpropanamide;
2-amino-N—((R)-3-(2-chlorophenoxy)-1-((R)-2-(2,2-dif-
luoroethyl)-3-oxo-3a-(pyridin-2-ylmethyl)-3a,4,6,7-tetra-
hydro-2H-pyrazolo[4,3-c]pyridin-5(3H)-yl)-1-oxopro-
pan-2-yl)-2-methylpropanamide;
2-amino-N—((R)-1-((R)-2-(2,2-difluoroethyl)-3-oxo-3a-
(pyridin-2-ylmethyl)-3a,4,6,7-tetrahydro-2H-pyrazolo[4,
3-c]pyridin-5(3H)-yl)-3-(2-fluorophenoxy)-1-oxopropan-
2-yl)-2-methylpropanamide;
2-amino-N—((R)-3-(3-chlorophenoxy)-1-((R)-2-(2,2-dif-
luoroethyl)-3-oxo-3a-(pyridin-2-ylmethyl)-3a,4,6,7-tetra-
hydro-2H-pyrazolo[4,3-c]pyridin-5(3H)-yl)-1-oxopro-
pan-2-yl)-2-methylpropanamide;
2-amino-N—((R)-1-((R)-2-(2,2-difluoroethyl)-3-oxo-3a-
(pyridin-2-ylmethyl)-3a,4,6,7-tetrahydro-2H-pyrazolo[4,
3-c]pyridin-5(3H)-yl)-3-(3-methoxyphenoxy)-1-oxopro-
pan-2-yl)-2-methylpropanamide;
2-amino-N—((R)-1-((R)-2-(2,2-difluoroethyl)-3-oxo-3a-
(pyridin-2-ylmethyl)-3a,4,6,7-tetrahydro-2H-pyrazolo[4,
3-c]pyridin-5(3H)-yl)-3-(3-fluorophenoxy)-1-oxopropan-
2-yl)-2-methylpropanamide; and
2-amino-N—((R)-1-((R)-3a-benzyl-2-methyl-3-oxo-3a,4,6,
7-tetrahydro-2H-pyrazolo[4,3-c]pyridin-5(3H)-yl)-3-(4-
fluorophenoxy)-1-oxopropan-2-yl)-2-methylpropana-
mide;
or a pharmaceutically acceptable salt thereof.

[8] More suitable individual compounds of the invention are:
  2-amino-N—((R)-1-((R)-3a-benzyl-2-methyl-3-oxo-3a,
  4,6,7-tetrahydro-2H-pyrazolo[4,3-c]pyridin-5(3H)-yl)-3-(2,
  4-difluorophenoxy)-1-oxopropan-2-yl)-2-methylpropana-
  mide;
  2-amino-N—((R)-1-((R)-3a-benzyl-2-methyl-3-oxo-3a,
  4,6,7-tetrahydro-2H-pyrazolo[4,3-c]pyridin-5(3H)-yl)-1-
  oxo-3-phenoxypropan-2-yl)-2-methylpropanamide;
2-amino-N—((R)-1-((R)-3a-benzyl-2-methyl-3-oxo-3a,4,6,
  7-tetrahydro-2H-pyrazolo[4,3-c]pyridin-5(3H)-yl)-3-(3,
  4-difluorophenoxy)-1-oxopropan-2-yl)-2-methylpro-
  panamide;
2-amino-N—((R)-1-((R)-3a-benzyl-2-methyl-3-oxo-3a,4,6,
  7-tetrahydro-2H-pyrazolo[4,3-c]pyridin-5(3H)-yl)-3-(3-
  fluorophenoxy)-1-oxopropan-2-yl)-2-methylpropana-
  mide;
2-amino-N—((R)-1-((R)-3a-benzyl-2-methyl-3-oxo-3a,4,6,
  7-tetrahydro-2H-pyrazolo[4,3-c]pyridin-5(3H)-yl)-3-(3-
  methoxyphenoxy)-1-oxopropan-2-yl)-2-methylpropana-
  mide;
2-amino-N—((R)-1-((R)-3a-benzyl-2-methyl-3-oxo-3a,4,6,
  7-tetrahydro-2H-pyrazolo[4,3-c]pyridin-5(3H)-yl)-3-(2-
  fluorophenoxy)-1-oxopropan-2-yl)-2-methylpropana-
  mide;
2-amino-N—((R)-1-((R)-3a-benzyl-2-methyl-3-oxo-3a,4,6,
  7-tetrahydro-2H-pyrazolo[4,3-c]pyridin-5(3H)-yl)-3-(3-
  cyanophenoxy)-1-oxopropan-2-yl)-2-methylpropana-
  mide;
2-amino-N—((R)-1-((R)-2-(2,2-difluoroethyl)-3-oxo-3a-
  (pyridin-2-ylmethyl)-3a,4,6,7-tetrahydro-2H-pyrazolo[4,
  3-c]pyridin-5(3H)-yl)-1-oxo-3-phenoxypropan-2-yl)-2-
  methylpropanamide;
2-amino-N—((R)-3-(2-chlorophenoxy)-1-((R)-2-(2,2-dif-
  luoroethyl)-3-oxo-3a-(pyridin-2-ylmethyl)-3a,4,6,7-tetra-
  hydro-2H-pyrazolo[4,3-c]pyridin-5(3H)-yl)-1-oxopro-
  pan-2-yl)-2-methylpropanamide;
2-amino-N—((R)-1-((R)-2-(2,2-difluoroethyl)-3-oxo-3a-
  (pyridin-2-ylmethyl)-3a,4,6,7-tetrahydro-2H-pyrazolo[4,
  3-c]pyridin-5(3H)-yl)-3-(2-fluorophenoxy)-1-oxopropan-
  2-yl)-2-methylpropanamide;
2-amino-N—((R)-1-((R)-2-(2,2-difluoroethyl)-3-oxo-3a-
  (pyridin-2-ylmethyl)-3a,4,6,7-tetrahydro-2H-pyrazolo[4,
  3-c]pyridin-5(3H)-yl)-3-(3-methoxyphenoxy)-1-oxopro-
  pan-2-yl)-2-methylpropanamide;
2-amino-N—((R)-1-((R)-2-(2,2-difluoroethyl)-3-oxo-3a-
  (pyridin-2-ylmethyl)-3a,4,6,7-tetrahydro-2H-pyrazolo[4,
  3-c]pyridin-5(3H)-yl)-3-(3-fluorophenoxy)-1-oxopropan-
  2-yl)-2-methylpropanamide; and
2-amino-N—((R)-1-((R)-3a-benzyl-2-methyl-3-oxo-3a,4,6,
  7-tetrahydro-2H-pyrazolo[4,3-c]pyridin-5(3H)-yl)-3-(4-
  fluorophenoxy)-1-oxopropan-2-yl)-2-methylpropana-
  mide;
or a pharmaceutically acceptable salt thereof.

[9] The present invention provides a pharmaceutical composition comprising a compound or a pharmaceutically acceptable salt thereof, as described in any one of [1] to [8], and a pharmaceutically acceptable carrier.

[10] The present invention provides the pharmaceutical composition as described in [9], further comprising another pharmacologically active agent.

[11] The present invention provides a method of treatment of an animal including human suffering from a condition or disorder mediated by the ghrelin receptor, which comprises administering to said subject an effective amount of a compound of formula (I) or a pharmaceutically acceptable salt according to any one of [1] to [8].

[12] The present invention provides the method as described in [11], wherein said condition or disorder is selected from the group consisting of: cancer anorexia/cachexia; cachexia and anorexia by anti-cancer drugs; hyperalgesia by anti-cancer drugs; COPD/COPD cachexia; sarcopenia; eating disorders and neurological eating disorders; weight loss suppression; early postoperative recovery of cancer patients; chronic respiratory tract infection; inflammation; IBD; FD; constipation; diabetic gastroparesis and gastroparesis; heart failure; myocardial infarction; diabetic neuropathy; Parkinson's disease; multiple sclerosis; diagnosis and treatment of growth hormone deficiency; elderly QOL improvement; bowel movement disturbance of spinal cord injury patients; postoperative ileus; and morphine induced ileus; and combinations thereof.

[13] The present invention provides a use of a compound described in any one of [1] to [8] or a pharmaceutically acceptable salt, or composition thereof for the manufacture of a medicament for the treatment of a condition or disorder mediated by the ghrelin receptor.

[14] The present invention provides the use as described in [13], wherein said condition or disorder is selected from the group consisting of: cancer anorexia/cachexia; cachexia and anorexia by anti-cancer drugs; hyperalgesia by anti-cancer drugs; COPD/COPD cachexia; sarcopenia; eating disorders and neurological eating disorders; weight loss suppression; early postoperative recovery of cancer patients; chronic respiratory tract infection; inflammation; IBD; FD; constipation; diabetic gastroparesis and gastroparesis; heart failure; myocardial infarction; diabetic neuropathy; Parkinson's disease; multiple sclerosis; diagnosis and treatment of growth hormone deficiency; elderly QOL improvement; bowel movement disturbance of spinal cord injury patients; postoperative ileus; and morphine induced ileus; and combinations thereof.

[15] The present invention provides a compound described in any one of [1] to [8] or a pharmaceutically acceptable salt thereof for use in the treatment of a condition or disorder mediated by the ghrelin receptor.

[16] The present invention provides a process for preparing a pharmaceutical composition comprising mixing a compound described in any one of [1] to [8] or a pharmaceutically acceptable salt thereof with a pharmaceutically acceptable carrier, diluent or excipient.

[17] The present invention provides an assay process for Growth hormone (GH) response in conscious fasting mice comprising oral administration of test compounds to BALB/c mice.

[18] The present invention provides an assay process for cisplatin-induced cachexia/anorexia in rats comprising administration of test compounds and cisplatin in the evening to well-handled rats.

[19] The present invention provides an assay process for cachexia (weight loss and muscle wasting) in rats bearing the AH-130 cells comprising oral administration of test compounds to immature male rats injected intraperitoneally with more than $1 \times 10^8$ AH-130 ascites hepatoma cells.

Advantageous Effects of Invention

The serine derivatives of the present invention are ghrelin receptor agonists and have a number of therapeutic applications, particularly in the treatment of cancer anorexia/cachexia; cachexia and anorexia by anti-cancer drugs; hyperalgesia by anti-cancer drugs; COPD/COPD cachexia; sarcopenia; eating disorders and neurological eating disorders; weight loss suppression; early postoperative recovery of cancer patients; chronic respiratory tract infection; inflammation; IBD; FD; constipation; diabetic gastroparesis and gastroparesis; heart failure; myocardial infarction; diabetic neuropathy; Parkinson's disease; multiple sclerosis; diagnosis and treatment of growth hormone deficiency; elderly QOL improvement; bowel movement disturbance of spinal cord injury patients; postoperative ileus; and morphine induced ileus.

As illustrated in the following Scheme I, the present invention is characterized by the serine moiety in the center part of serine derivatives. Pfizer Inc. discloses ghrelin receptor agonist in WO97/24369, which is regarded as a structurally close art. The closest compound is thought to be a compound of the example 183 in the WO97/24369, which is a homoserine derivative illustrated in Scheme II. The serine derivatives of the present invention show much better activities against the ghrelin receptor comparing with the homoserine examples. As shown in Table 7 in the experiment of the present specification, deletion of one carbon from a homoserine derivative surprisingly leads to a dramatic increase of the activity.

Scheme I: serine derivative

[Chem. 2]

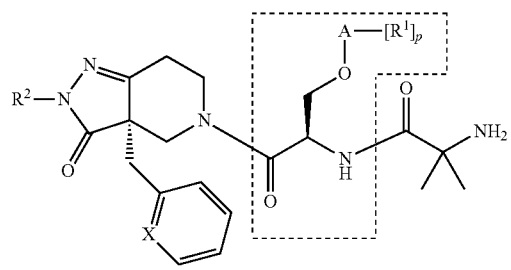

Scheme II: homoserine derivative

[Chem. 3]

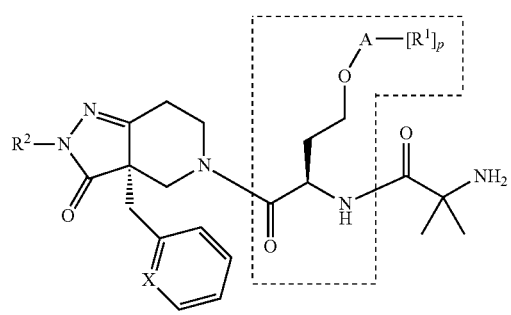

With respect to other compounds disclosed in the art, the compounds of the present invention can show less toxicity, good absorption and distribution, good solubility, less plasma protein binding, less drug-drug interaction, good metabolic stability, reduced inhibitory activity at HERG channel, and/or reduced QT prolongation.

DESCRIPTION OF EMBODIMENTS

As appreciated by those of skill in the art, "halogen" or "halo" as used herein is intended to include fluoro, chloro, bromo and iodo. Similarly, 1-6, as in $C_{1-6}$ is defined to identify the number as having 1, 2, 3, 4, 5 or 6. According to the definition, for example, $C_{1-6}$, as in $C_{1-6}$ alkyl is defined to identify the alkyl group as having 1, 2, 3, 4, 5 or 6 carbons. A group which is designated as being independently substituted with substituents may be independently substituted with multiple numbers of such substituents.

The term "alkyl", as used herein, means a linear saturated monovalent hydrocarbon radical or a branched saturated monovalent hydrocarbon radical, e.g., methyl, ethyl, propyl, 2-propyl, butyl (including all isomeric forms), pentyl (including all isomeric forms), and the like.

The term "aryl", as used herein, means mono- or bi-carbocyclic or mono- or bi-heterocyclic ring which may contain 0 to 4 heteroatoms selected from O, N and S, but not limited to, phenyl, naphthyl, benzofuranyl, benzofurazanyl, benzimidazolonyl, benzoimidazolyl, benzoisothiazolyl, benzoisoxazolyl, benzothiadiazolyl, benzothiazolyl, benzoxadiazolyl, benzoxazolonyl, benzoxazolyl, benzothiophenyl, benzotriazolyl, carbazolyl, carbolinyl, chromanyl, cinnolinyl, 2,3-dioxoindolyl, furanyl, furazanyl, furopyridyl, furopyrrolyl, imidazolyl, imidazopyrazinyl, imidazopyridinyl, imidazopyrimidinyl, imidazothiazolyl, indazolyl, indolazinyl, indolinyl, indolyl, isobenzofuranyl, isochromanyl, isoindolyl, isoquinolyl, isoxazolopyridyl, isoxazolinyl, isoxazolyl, isothiazolyl, naphthyridinyl, oxazolinyl, oxadiazolyl, oxazolyl, oxetanyl, 2-oxoindolyl, phthalazyl, pyrazolopyridyl, pyrazolopyrimidinyl, pyrazolyl, pyrazinyl, pyridyl, pyrimidyl, pyridazinyl, pyridopyrimidinyl, pyrrolopyridyl, pyrrolyl, quinazolinyl, quinolyl, quinoxalinyl, tetrazolopyridyl, tetrazolyl, thiadiazolyl, thiazolyl, thiophenyl, thienopyrazinyl, thienopyrazolyl, thienopyridyl, thienopyrrolyl, triazolopyrimidinyl, triazolyl, 4-oxo-1,4-dihydroquinolyl, 2-oxo-1,2-dihydropyridyl, 4-oxo-1,4-dihydropyrimidyl, 2-oxo-1,2-dihydroquinolyl, 4-oxo-4H-pyrido[1,2-a]pyrimidyl, 4-oxo-1,4-dihydro-1,8-naphthyridyl, and N-oxides thereof.

As used herein, the term "treatment" refers to alleviating the specified condition, eliminating or reducing the symptoms of the condition, slowing or eliminating the progression of the condition, and preventing or delaying the reoccurrence of the condition in a previously afflicted patient or subject.

As used herein, the term "evening" refers to from around 16:00 to 24:00, preferably around from 17:00 to 20:00.

As used herein, the article "a" or "an" refers to both the singular and plural form of the object to which it refers unless indicated otherwise.

The term "animal," as used herein, includes a mammalian subject or a non-mammalian subject. Examples of suitable mammalian subject may include, without limit, human, rodents, companion animals, livestock, and primates. Suitable rodents may include, but are not limited to, mice, rats, hamsters, gerbils, and guinea pigs. Suitable companion animals may include, but are not limited to, cats, dogs, rabbits, and ferrets. Suitable livestock may include, but are not limited to, horses, goats, sheep, swine, cattle, llamas, and alpacas. Suitable primates may include, but are not limited to, chimpanzees, lemurs, macaques, marmosets, spider monkeys, squirrel monkeys, and vervet monkeys. Examples of suitable non-mammalian subject may include, without limit, birds, reptiles, amphibians, and fish. Non-limiting examples of birds include chickens, turkeys, ducks, and geese. The preferred mammalian subject is a human.

Salts of the compounds of the present invention are also encompassed within the scope of the invention. Because of their potential use in medicine, the salts of the compounds of formula (I) are preferably pharmaceutically acceptable. Suitable pharmaceutically acceptable salts can include acid addition salts. A pharmaceutically acceptable acid addition salt can be formed by reaction of a compound of formula (I) with a suitable inorganic or organic acid (such as hydrobromic, hydrochloric, hydroiodic, sulfuric, nitric, phosphoric, p-toluenesulfonic, methanesulfonic or naphthalenesulfonic acid), optionally in a suitable solvent such as an organic solvent, to give the salt which is usually isolated for example by crystallisation and filtration. Examples of pharmaceutically acceptable acid addition salts of a compound of formula (I) include the HCl, HBr, HI, sulfate or bisulfate, nitrate, phosphate or hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate salts. For reviews on suitable pharmaceutical salts see Berge et al, J. Pharm, Sci, 66, 1-19, 1977; P L Gould, International Journal of Pharmaceutics, 33 (1986), 201-217; and Bighley et al, Encyclopedia of Pharmaceutical Technology, Marcel Dekker Inc, New York 1996, Volume 13, page 453-497. Other salts, which are not pharmaceutically acceptable, for example the trifluoroacetate salt, may be useful in the preparation of compounds of this invention and these form a further aspect of the invention. The invention includes within its scope all possible stoichiometric and non-stoichiometric forms of the salts of the compounds of formula (I).

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention.

Salts and solvates having non-pharmaceutically acceptable counter-ions or associated solvents are within the scope of the present invention, for example, for use as intermediates in the preparation of other compounds of formula (I) and their pharmaceutically acceptable salts.

Compounds of formula (I) may have polymorphs in crystalline form, which are within the scope of the present invention.

Also within the scope of the invention are so-called "prodrugs" of the compounds of formula (I). Thus certain derivatives of compounds of formula (I) which may have little or no pharmacological activity themselves can, when administered into or onto the body, be converted into compounds of formula (I) having the desired activity, for example, by hydrolytic or hydrolysis cleavage. Such derivatives are referred to as "prodrugs". Further information on the use of prodrugs may be found in Pro-drugs as Novel Delivery Systems, Vol. 14, ACS Symposium Series (T Higuchi and W Stella) and Bioreversible Carriers in Drug Design, Pergamon Press, 1987 (ed. E B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in Design of Prodrugs by H. Bundgaard (Elsevier, 1985). Some examples of prodrugs in accordance with the invention include:

(i) where the compound of formula (I) contains an alcohol functionality (—OH), compounds wherein the hydroxy group is replaced with a moiety convertible in vivo into the hydroxy group. Said moiety convertible in vivo into the hydroxy group means a moiety transformable in vivo into a hydroxyl group by e.g. hydrolysis and/or by an enzyme, e.g. an esterase. Examples of said moiety include, but are not limited to, ester and ether groups which may be hydrolyzed easily in vivo. Preferred are the moieties replaced the hydrogen of hydroxy group with acyloxyalkyl, 1-(alkoxycarbonyloxy) alkyl, phthalidyl and acyloxyalkyloxycarbonyl such as pivaloyloxymethyloxycarbonyl; and (ii) where the compound of formula (I) contains an amino group, a pyrrolopyridinone derivative prepared by reacting with a suitable acid halide or a suitable acid anhydride is exemplified as a prodrug. A particularly preferred pyrrolopyridinone derivative as a prodrug is —NHCO(CH$_2$)$_2$OCH$_3$, —NHCOCH(NH$_2$)CH$_3$ or the like.

Further examples of replacement groups in accordance with the foregoing examples and examples of other prodrug types may be found in the aforementioned references.

Additionally, compounds of formula (I) may be administered as prodrugs. As used herein, a "prodrug" of a compound of formula (I) is a functional derivative of the compound which, upon administration to a patient, eventually liberates the compound of formula (I) in vivo. Administration of a compound of formula (I) as a prodrug may enable the skilled artisan to do one or more of the following: (a) modify the onset of action of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

In certain of the compounds of formula (I), there may be one or more chiral carbon atoms. In such cases, compounds of formula (I) exist as stereoisomers. The invention extends to all optical isomers such as stereoisomeric forms of the compounds of formula (I) including enantiomers, diastereoisomers and mixtures thereof, such as racemates. The different stereoisomeric forms may be separated or resolved one from the other by conventional methods or any given isomer may be obtained by conventional stereoselective or asymmetric syntheses.

Certain of the compounds herein can exist in various tautomeric forms and it is to be understood that the invention encompasses all such tautomeric forms.

The invention also includes all suitable isotopic variations of a compound of the invention. An isotopic variation of a compound of the invention is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, phosphorus, sulphur, fluorine and chlorine such as $^{2}H$, $^{3}H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the invention, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and detectability. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. Isotopic variations of the compounds of the invention can generally be prepared by conventional procedures such as by the illustrative methods or by the preparations described in the Compounds hereafter using appropriate isotopic variations of suitable reagents.

In a further embodiment the present invention thus also provides compounds of formula (I) and pharmaceutically acceptable salts or solvates thereof, for use in medical therapy, and particularly in the treatment of disorders mediated by the ghrelin receptor.

In a further embodiment the present invention is directed to methods of modulating ghrelin receptor activity for the prevention and/or treatment of disorders mediated by the ghrelin receptor.

In a further embodiment the present invention provides a method of treatment of an animal including human suffering from a disorder mediated by the ghrelin receptor, which comprises administering to said subject an effective amount of a compound of formula (I) or a pharmaceutically acceptable salt or solvate thereof. Such treatment comprises the step of administering a therapeutically effective amount of the compound of formula (I), including a pharmaceutically acceptable salt or solvate thereof. Such treatment can also comprise the step of administering a therapeutically effective amount of a pharmaceutical composition containing a compound of formula (I), including a pharmaceutically acceptable salt or solvate thereof.

A further embodiment of the present invention provides the use of a compound of formula (I), or a pharmaceutically acceptable salt or solvate thereof, in the preparation of a medicament for the treatment of a disorder mediated by the ghrelin receptor.

The action of the endogenous ligand ghrelin at the ghrelin receptor has been shown to result in potent growth-hormone releasing activity, appetite stimulation, stimulation of gastric motility and acid secretion, positive cardiovascular effects and direct action on bone formation. Thus, a ghrelin receptor modulator may achieve a beneficial effect in the treatment of growth-hormone deficiencies, eating disorders, gastrointestinal disease, cardiovascular diseases, osteoporosis, aging and catabolic states or chronic wasting syndromes (Kojima and Kangawa, Nature Clinical Practice, February 2006, Vol. 2, No. 2, 80-88). A ghrelin receptor modulator may also achieve a beneficial effect in the treatment of sleep disorders (Brain Research, 1088 (2006) 131-140).

Particular disorders which are associated with the ghrelin receptor and thus may be mediated by the ghrelin receptor such that a ghrelin receptor modulator may achieve a beneficial effect include obesity and risk factors associated with obesity, including but not limited to diabetes, complications associated with diabetes, metabolic syndrome, cardiovascular disorders (including atherosclerosis and dyslipidemia).

Other diseases and/or conditions mediated by the ghrelin receptor wherein a ghrelin include the following, treating a growth hormone deficient state, increasing muscle mass, increasing bone density, treating sexual dysfunction in males and females, facilitating a weight gain, facilitating weight maintenance, facilitating appetite increase (for example facilitating weight gain, maintenance or appetite increase is useful in a patient having a disorder, or undergoing a treatment, accompanied by weight loss). Examples of diseases or disorders accompanied by weight loss include anorexia, bulimia, cancer cachexia, AIDS, wasting, cachexia and wasting in frail elderly. Examples of treatments accompanied by weight loss include chemotherapy, radiation therapy, temporary or permanent immobilisation, and dialysis.

Further diseases or conditions include sleep disorders, congestive heart failure, metabolic disorder, improvements in memory function, breast cancer, thyroid cancer, ameliorating ischemic nerve or muscle damage.

The compounds of the invention function by modulating the activity of the ghrelin receptor. They may activate/inactivate the receptor by acting as an agonist, partial agonist, inverse agonist, antagonist or partial antagonist.

Eating disorders include Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; Binge Eating Disorder; and Eating Disorder Not Otherwise Specified (307.50) [the numbers in brackets after the listed diseases above refer to the classification code in Diagnostic and Statistical Manual of Mental Disorders, 4th Edition, published by the American Psychiatric Association (DSM-IV) and/or the International Classification of Diseases, 10th Edition (ICD-10)].

In a further embodiment the invention provides the use of a compound of formula (I), or a pharmaceutically acceptable salt or solvate thereof, in the preparation of a medicament for the treatment of an eating disorder.

In a further embodiment the present invention provides a method of treatment of an animal including human suffering from an eating disorder which comprises administering to said subject an effective amount of a compound of formula (I) or a pharmaceutically acceptable salt or solvate thereof.

Gastrointestinal diseases include gastric ileus, gastric ulcer and inflammatory bowel diseases such as Crohn's disease and ulcerative colitis. The compounds of the invention may also be useful for treatments to alleviate symptoms associated with gastroesophageal reflux and/or with dyspepsia, with or without appetite-/metabolic-related cachexia, and in the treatment of paralytic ileus or pseudo obstruction, and of conditions associated with constipation, such as constipation-predominant irritable bowel syndrome.

Cardiovascular diseases include heart failure and dilated cardiomyopathy.

Catabolic states or chronic wasting syndromes may be seen in post-operative patients and also include AIDS-associated and cancer-associated wasting syndromes, such as cancer cachexia.

While it is possible that, for use in therapy a therapeutically effective amount of a compound of formula (I), or a pharmaceutically acceptable salt or solvate thereof, may be administered as the raw chemical, it is possible to present the active ingredient as a pharmaceutical composition. Thus, in a further embodiment the invention provides a pharmaceutical composition comprising a compound of formula (I), or a pharmaceutically acceptable salt or solvate thereof, in admixture with one or more pharmaceutically acceptable carriers, diluents, or excipients. The carrier(s), diluent(s) or excipient(s) must be acceptable in the sense of being compatible with the other ingredients of the formulation and not deleterious to the recipient thereof. In a further embodiment the invention also provides a process for the preparation of a pharmaceutical composition including admixing a compound of formula (I), or a pharmaceutically acceptable salt or solvate thereof, with one or more pharmaceutically acceptable carriers, diluents or excipients.

Pharmaceutical compositions of the invention may be formulated for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Therefore, the pharmaceutical compositions of the invention may be formulated, for example, as tablets, capsules, powders, granules, lozenges, creams or liquid preparations, such as oral or sterile parenteral solutions or suspensions. Such pharmaceutical formulations may be prepared by any method known in the art of pharmacy, for example by bringing into association the active ingredient with the carrier(s) or excipient(s).

Tablets and capsules for oral administration may be in unit dose presentation form, and may contain conventional excipients such as binding agents, for example syrup, acacia, gelatine, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatine, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams. The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Pharmaceutical formulations adapted for parenteral administration include aqueous and nonaqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical formulations adapted for rectal administration may be presented as suppositories or as enemas.

Pharmaceutical formulations adapted for nasal administration wherein the carrier is a solid may include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

It should be understood that in addition to the ingredients particularly mentioned above, the formulations may include other agents conventional in the art having regard to the type of formulation in question.

A therapeutically effective amount of a compound of formula (I), or a pharmaceutically acceptable salt or solvate thereof will depend upon a number of factors including, for example, the age and weight of the human or other animal, the precise condition requiring treatment and its severity, the nature of the formulation, and the route of administration, and will ultimately be at the discretion of the attendant physician or veterinarian. However, an effective amount of a compound of formula (I) for the treatment of disorders mediated by the ghrelin receptor will generally be in the range of 0.1 to 100 mg/kg body weight of recipient (animal) per day and more usually in the range of 1 to 10 mg/kg body weight per day. Thus, for a 70 kg adult animal, the actual amount per day would usually be from 70 to 700 mg and this amount may be given in a single dose per day or more usually in a number (such as two, three, four, five or six) of sub-doses per day such that the total daily dose is the same. An effective amount of a pharmaceutically acceptable salt or solvate thereof, may be determined as a proportion of the effective amount of the compound of formula (I) per se.

A compound of formula (I), or a pharmaceutically acceptable salt or solvate thereof for use in the instant invention may be used in combination with one or more other therapeutic agents. The invention thus provides in a further embodiment a combination comprising a compound of formula (I), or a pharmaceutically acceptable salt or solvate thereof together with a further therapeutic agent, which may be for example an additional anti-obesity agent. In a yet further embodiment the invention also provides the use of a combination comprising a compound of formula (I), or a pharmaceutically acceptable salt or solvate thereof with a further therapeutic agent in the treatment of disorders mediated by the ghrelin receptor.

When a compound of formula (I), or a pharmaceutically acceptable salt or solvate thereof is used in combination with one or more other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optimally together with a pharmaceutically acceptable carrier or excipient comprise a further embodiment of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, conveniently in such a manner as are known for such compounds in the art.

When a compound is used in combination with a second therapeutic agent active against the same disease, the dose of each compound may differ from that when the compound is used alone. Appropriate doses will be readily appreciated by those skilled in the art.

A compound of the present invention may be usefully combined with another pharmacologically active compound, or with two or more other pharmacologically active compounds, particularly in the treatment of inflammatory, pain and urological diseases or disorders. For example, a ghrelin receptor agonist, particularly a compound of formula (I), or a prodrug thereof or a pharmaceutically acceptable salt or solvate thereof, may be administered simultaneously, sequentially or separately in combination with one or more agents selected from:

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflunisal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butalbital, mephobarbital, metharbital, methohexital, pentobarbital, phenobarbital, secobarbital, talbutal, thiamylal or thiopental;

a benzodiazepine having a sedative action, e.g. chlordiazepoxide, clorazepate, diazepam, flurazepam, lorazepam, oxazepam, temazepam or triazolam;

an H1 antagonist having a sedative action, e.g. diphenhydramine, pyrilamine, promethazine, chlorpheniramine or chlorcyclizine; —a sedative such as gluethimide, meprobamate, methaqualone or dichloralphenazone;

a skeletal muscle relaxant, e.g. baclofen, carisoprodol, chlorzoxazone, cyclobenzaprine, methocarbamol or orphenadrine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex (Trademark), a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazosin, tamsulosin, clonidine, guanfacine, dexmedetomidine, modafinil, or 4-amino-6,7-dimethoxy-2-(5-methane-sulfonamido-1,2,3,4-tetrahydroisoquinol-2-yl)-5-(2-pyridyl) quinazoline;

a tricyclic antidepressant, e.g. desipramine, imipramine, amitriptyline or nortriptyline;

an anticonvulsant, e.g. carbamazepine, lamotrigine, topiratmate or valproate;

a tachykinin (NK) antagonist, particularly an NK-3, NK-2 or NK-1 antagonist, e.g. alphaR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6, 13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g. oxybutynin, tolterodine, propiverine, trospium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion (Trademark) or sarizotan;

a vanilloid receptor agonist (e.g. resiniferatoxin) or antagonist (e.g. capsazepine);

a transient receptor potential cation channel subtype (V1, V2, V3, V4, M8, M2, A1) agonist or antagonist;

a beta-adrenergic such as propranolol;

a local anaesthetic such as mexiletine;

a corticosteroid such as dexamethasone;

a 5-HT receptor agonist or antagonist, particularly a 5-HT1B/1D agonist such as eletriptan, sumatriptan, naratriptan, zolmitriptan or rizatriptan;

a 5-HT2A receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol (Trademark);

a PDEV inhibitor, such as 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil), (6R, 12aR)-2,3,6,7,12,12a-hexahydro-2-methyl-6-(3,4-methylenedioxyphenyl)pyrazino [2',1':6,1]pyrido[3,4-b]indole-1,4-dione (IC-351 or tadalafil), 2-[2-ethoxy-5-(4-ethyl-piperazin-1-yl-sulphonyl)phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl) pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (3-(aminomethyl)bicyclo[3.2.0]hept-3-yl)acetic acid, (3S,5R)-3-(aminomethyl)-5-methylheptanoic acid, (3S,5R)-3-amino-5-methylheptanoic acid, (3S,5R)-3-amino-5-methyloctanoic acid, (2S,4S)-4-(3-chlorophenoxy)proline, (2S,4S)-4-(3-fluorobenzyl)proline, [(1R,5R,6S)-6-(aminomethyl)bicyclo[3.2.0]hept-6-yl]acetic acid, 3-((1-(aminomethyl)cyclohexyl)methyl)-4H-[1,2,4] oxadiazol-5-one, C-[1-((1H-tetrazol-5-yl)methyl)cycloheptyl]methylamine, (3S,4S)-(1-(aminomethyl)-3,4-dimethylcyclopentyl)acetic acid, (3S,5R)-3-(aminomethyl)-5-methyloctanoic acid, (3S,5R)-3-amino-5-methylnonanoic acid, (3S,5R)-3-amino-5-methyloctanoic acid, (3R,4R,5R)-3-amino-4,5-dimethylheptanoic acid, and (3R,4R,5R)-3-amino-4,5-dimethyloctanoic acid;

a cannabinoid;

a metabotropic glutamate subtype 1 receptor (mGluR1) antagonist;

a serotonin reuptake inhibitor such as sertraline, sertraline metabolite desmethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazapine, oxaprotiline, fezolamine, tomoxetine, mianserin, bupropion, bupropion metabolite hydroxybupropion, nomifensine and viloxazine (Vivalan (Trademark)), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl] thio]-5-thiazolebutanol, 2-[[(1R,3S)-3-amino-4-hydroxy-1-(5-thiazolyl)butyl]thio]-6-(trifluoromethyl)-3-pyridinecarbonitrile, 2-[[(1R,3S)-3-amino-4-hydroxy-1-(5-thiazolyl) butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin E2 subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(1S)-1-({[5-chloro-2-(3-fluorophenoxy) pyridin-3-yl]carbonyl}amino)ethyl]benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxymethyl]-1-methyl-2-quinolone (ZD-2138), or 2,3,5-trimethyl-6-3-pyridylmethyl)-1, 4-benzoquinone (CV-6504);

a sodium channel blocker, such as lidocaine;

a calcium channel blocker, such as ziconotide, zonisamide, mibefradil;

a 5-HT3 antagonist, such as ondansetron;

a calcitonin gene related peptide (CGRP) antagonist;

a bradykinin (BK1 and BK2) antagonist;

a voltage gated sodium dependent channel blocker ($Na_{v1.3}$, $Na_{v1.7}$, $Na_{v1.8}$);

a voltage dependent calcium channel blocker (N-type, T-type);

a P2X (ion channel type ATP receptor) antagonist;

an acid-sensing ion channel (ASIC1a, ASIC3) antagonist;

an Angiotensin AT2 antagonist;

a Chemokine CCR2B receptor antagonist;

a Cathepsin (B, S, K) inhibitor;

a sigmal receptor agonist or antagonist;

and the pharmaceutically acceptable salts and solvates thereof.

In particular, the therapeutic or prophylactic agent of the present invention can be preferably used in combination with chemotherapeutic agents, immunotherapeutic agents, diuretic agents and the like.

Examples of the chemotherapeutic agents include alkylating agents such as cyclosphosphamide, ifosfamide, melphalan, busulfan, nimustine, ranimustine, temozolomide and the like; antimetabolites of nucleic acid metabolism such as methotrexate, fluorouracil, tegafur, carmofur, doxifluridine, capecitabine, cytarabine, ancitabine, enocitabine, cytarabine ocfosfate, gemcitabine, mercaptopurine, fludarabine and the like; antitumor antibiotics such as doxorubicin, daunorubicin, pirarubicin, epirubicin, idarubicin, mitoxantrone, mitomycin C, bleomycin, peplomycin and the like; microtubule inhibitors such as vincristine, vinblastine, vindesine, vinorelbine, paclitaxel, docetaxel and the like; platinum-based drugs such as cisplatin, carboplatin, nedaplatin and the like; topoisomerase inhibitors such as irinotecan, nogitecan, etoposide and the like; molecular targeted therapeutic agents such as trastuzumab, rituximab, imanitib and the like; or the like.

Examples of the immunotherapeutic agents include muramyl dipeptide derivatives, lentinan, sizofiran, ubenimex, picibanil, krestin, interferon, interleukin, granulocyte colony stimulating factor, erythropoietin and the like.

Examples of the diuretic agents include xanthine derivative drugs such as theobromine sodium salicylate; thiazide drugs such as ethiazide, cyclopenthiazide, trichlormethiazide, hydrochlorothiazide, hydroflumethiazide, benzyl hydrochlorothiazide, penflutizide, polythiazide, methyclothiazide; anti-aldosterone drugs such as spironolactone, triamterene and the like; carbonic anhydrase inhibitors such as acetazolamide and the like; chlorobenzene sulfonamide drugs such as chlortalidone, mefruside, indapamide, furosemide, azosemide and the like; isosorbide, ethacrynic acid, piretanide, bumetanide and the like.

Such combinations offer significant advantages, including synergistic activity, in therapy.

All publications, including but not limited to patents and patent applications, cited in this specification are herein incorporated by reference as if each individual publication were specifically and individually indicated to be incorporated by reference herein as though fully set forth.

General Synthesis

Throughout the instant application, the following abbreviations are used with the following meanings:

DCM Dichloromethane
DMA N,N-dimethylacetamide
DME 1,2-dimethoxyethane
DMF N,N-dimethylformamide
DMSO Dimethyl sulfoxide
EDC 1-Ethyl-3-(3-dimethylaminopropyl) carbodiimide Hydrochloride
EtOAc Ethyl acetate
EtOH ethanol
ESI Electrospray ionization
HOBT 1-Hydroxybenztriazole
HBTU O-(Benzotriazol-1-yl)-N,N,N',N'-tetramethyluronium hexafluorophosphate
HPLC High pressure liquid chromatography
LC liquid chromatography
LG Leaving group
MeCN Acetonitrile
MeOH methanol
MHz Megahertz
MS Mass spectrometry
NMR Nuclear magnetic resonance
PG Protecting group
T3P 2,4,6-tripropyl-1,3,5,2,4,6-trioxatriphosphinane 2,4,6-trioxide
TBME Methyl ter-butyl ether
TFA Trifluoroacetic acid
THF Tetrahydrofuran
TLC Thin layer chromatography
tR Retention time
UV Ultraviolet The term of "base" is likewise no particular restriction on the nature of the bases used, and any base commonly used in reactions of this type may equally be used here. Examples of such bases include: alkali metal hydroxides, such as lithium hydroxide, sodium hydroxide, potassium hydroxide, potassium phosphate, and barium hydroxide; alkali metal hydrides, such as lithium hydride, sodium hydride, and potassium hydride; alkali metal alkoxides, such as sodium methoxide, sodium ethoxide, and potassium t-butoxide; alkali metal carbonates, such as lithium carbonate, sodium carbonate, potassium carbonate, and cesium carbonate; alkali metal hydrogencarbonates, such as lithium hydrogencarbonate, sodium hydrogencarbonate, and potassium hydrogen-carbonate; amines, such as N-methylmorpholine, triethylamine, tripropylamine, tributylamine, diisopropylethylamine, N-methylpiperidine, pyridine, 4-pyrrolidinopyridine, picoline, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO), 1,8-diazabicyclo[5.4.0]undec-7-ene (DBU), lutidine, and colidine; alkali metal amides, such as lithium amide, sodium amide, potassium amide, lithium diisopropyl amide, potassium diisopropyl amide, sodium diisopropyl amide, lithium bis(trimethylsilyl)amide and potassium bis(trimethylsilyl)amide. Of these, triethylamine, diisopropylethylamine, DBU, DBN, DABCO, pyridine, lutidine, colidine, sodium carbonate, sodium hydrogencarbonate, sodium hydroxide, potassium carbonate, potassium hydrogencarbonate, potassium hydroxide, potassium phosphate, barium hydroxide, and cesium carbonate are preferred.

The reactions are normally and preferably effected in the presence of inert solvent. There is no particular restriction on the nature of the solvent to be employed, provided that it has no adverse effect on the reaction or the reagents involved and that it can dissolve reagents, at least to some extent. Examples of suitable solvents include, but not limited to: halogenated hydrocarbons, such as dichloromethane, chloroform, carbon tetrachloride, and dichloroethane; ethers, such as diethyl ether, diisopropyl ether, THF, and dioxane; aromatic hydrocarbons, such as benzene, toluene and nitrobenzene; amides, such as, DMF, N,N-dimethylacetamide (DMA), and hexamethylphosphoric triamide; amines, such as N-methylmorpholine, triethylamine, tripropylamine, tributylamine, diisopropylethylamine, N-methylpiperidine, pyridine, 4-pyrrolidinopyridine, N,N-dimethylaniline, and N,N-diethylaniline; alcohols, such as methanol, ethanol, propanol, isopropanol, and butanol; nitriles, such as acetonitrile and benzonitrile; sulfoxides, such as dimethyl sulfoxide (DMSO) and sulfolane; ketones, such as acetone and diethylketone. Of these solvents, including but not limited to DMF, DMA, DMSO, THF, diethylether, diisopropylether, dimethoxyethane, acetonitrile, dichloromethane, dichloroethane and chloroform are preferred.

EXAMPLES

The invention is illustrated in the following non-limiting examples in which, unless stated otherwise: all reagents are commercially available, all operations were carried out at room or ambient temperature, that is, in the range of about 18-25° C.; evaporation of solvent was carried out using a rotary evaporator under reduced pressure with a bath temperature of up to about 60° C.; reactions were monitored by thin layer chromatography (TLC) or LC-MS (low-resolution mass spectrum) and reaction times are given for illustration only; the structure and purity of all isolated compounds were assured by at least one of the following techniques: TLC (Merck silica gel 60 $F_{254}$ precoated TLC plates or Merck NH2 $F_{254}$ precoated HPTLC plates), mass spectrometry or NMR. Yields are given for illustrative purposes only. Flash column chromatography was carried out using Wakogel (registered trademark) C-300HGT or Fuji Silysia Chromatorex (registered trademark) DM2035 (Amino Type, 30-50 micrometer) or Biotage silica (32-63 mm, KP-Sil) or Biotage amino bounded silica (35-75 mm, KP-NH). Low-resolution mass spectral data (ESI) were obtained by the following apparatus:

Apparatus; Waters Alliance 2695 HPLC system with UV2487 detector and ZQ2000 mass spectrometer The purification of compounds using HPLC (preparative LC-MS) was performed by the following apparatus and conditions.

Apparatus; Waters MS-trigger Auto-purification system

Column; Waters XBridge C18, 19×50 mm, 5 micrometer particle size Condition A: Methanol or Acetonitrile/0.05% (v/v) Ammonia aqueous solution Condition B: Methanol or Acetonitrile/0.05% (v/v) Formic acid aqueous solution Conditions for determining HPLC retention time:

Method: QC1

Apparatus: Waters ACQUITY Ultra Performance LC with TUV detector and ZQ2000 mass spectrometer Column: Waters ACQUITY C18, 2.1×100 mm, 1.7 micrometer particle size Column temperature: 60° C.
Flow rate: 0.7 mL/min
Run time: 3 min
UV detection: 210 nm
MS detection: ESI positive/negative mode
Mobile phases:
A1: 10 mM Ammonium acetate
B1: Acetonitrile
Table 1. Gradient program:

TABLE 1

| Time (min) | A1(%) | B1(%) |
|---|---|---|
| 0 | 95 | 5 |
| 0.1 | 95 | 5 |
| 1.8 | 5 | 95 |
| 2.3 | 95 | 5 |

Method: QC2

Apparatus: Waters Alliance2795 HPLC system with 2996PDA detector and ZQ2000 mass spectrometer Column: XBridge C18, 4.6×50 mm, 3.5 micrometer particle size Column temperature: 45° C.
Flow rate: 1.2 mL/min
Run time: 4.5 min
UV detection: 210-400 nm (scan range)
MS detection: ESI positive/negative mode
Mobile phases:
A: Water
B: Acetonitrile
C: 1% Formic acid aqueous solution
D: 1% Ammonia aqueous solution
Table 2. Gradient program:

TABLE 2

| Time (min) | A (%) | B (%) | C (%) | D (%) |
|---|---|---|---|---|
| 0 | 85 | 10 | 2.5 | 2.5 |
| 0.2 | 85 | 10 | 2.5 | 2.5 |
| 3.2 | 0 | 95 | 2.5 | 2.5 |
| 3.7 | 0 | 95 | 2.5 | 2.5 |
| 3.71 | 85 | 10 | 2.5 | 2.5 |
| 4.5 | 85 | 10 | 2.5 | 2.5 |

Optical purity evaluation was performed by the following apparatus and conditions:

Apparatus: Waters Alliance2695 HPLC system with 2996PDA detector

Column: DAICEL CHIRALCEL OD-H, 4.6×250 mm, 5 micrometer particle size

Column temperature: 25° C. (room temperature)
Mobile phase: n-Hexane/2-Propanol/Diethylamine=90/10/0.1 (v/v/v)
Flow rate: 1 mL/min
Run time: 30 min
Auto-sampler temperature: 5° C.
UV detection: 259 nm NMR data were determined at 270 MHz (JEOL JNM-LA 270 spectrometer) or 300 MHz (JEOL JNM-LA300) using deuterated chloroform (99.8% D) or dimethyl-sulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br=broad, etc. Chemical symbols have their usual meanings; M (mol(s) per liter), L (liter(s)), mL (milliliter(s)), g (gram(s)), mg (milligram(s)), mol (moles), mmol (millimoles). Each prepared compound is generally named by ChemBioDraw (Ultra, version 12.0, CambridgeSoft).

All of the serine derivatives of formula (I) can be prepared by the procedures described in the general methods presented below or by the specific methods described in the Examples section and the Preparations section, or by routine modifications thereof. The present invention also encompasses any one or more of these processes for preparing the serine derivatives of formula (I), in addition to any novel intermediates used therein.

In the following general methods, descriptors are as previously defined for the serine derivatives of formula (I) unless otherwise stated.

<Scheme A>

[Chem. 4]

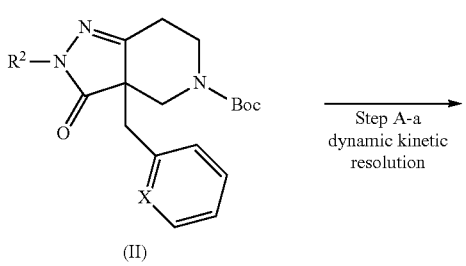

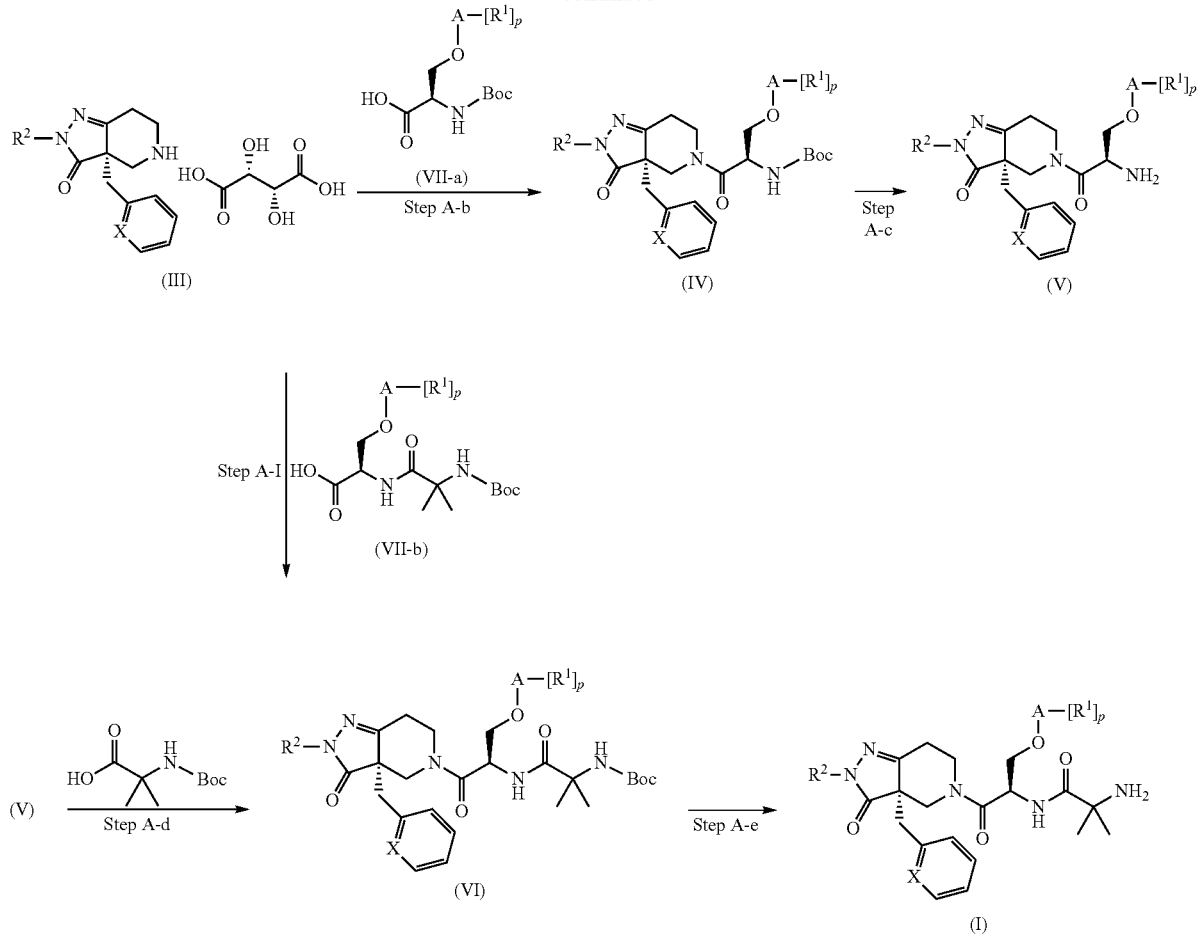

In Step A-a, a compound of formula (III) can be prepared from a compound of formula (II) by de-protection followed by dynamic kinetic resolution of the corresponding salt. De-protection can be conducted by the conventional methods known to those skilled in the art (typical amino protecting groups described in "Protective Groups in Organic Synthesis Forth Edition" edited by T. W. Greene et al. (John Wiley & Sons, 2007)). Further, de-protected compound can be converted to enantiomerically pure salt by dynamic kinetic resolution with enantiomerically pure acid, but not limited to, such as D-tartaric acid using suitable solvent. Examples of suitable solvent include such as DCM (dichloromethane), acetone, EtOAc, THF, and water. The dynamic kinetic resolution can be carried out at a temperature from about 0 to 150° C., more preferably from about 20 to 100° C. The dynamic kinetic resolution can be carried out in a time, in general, from about 1 hr to 48 hrs.

In Step A-b, a compound of formula (IV) can be prepared from a compound of formula (III) by amidation with a compound of formula (VII-a) using a suitable condensation reagent, but not limited to, such as T3P, HBTU and EDC-HOBT. The condensation can be carried out preferably under the presence of a base such as triethylamine and N,N-diisopropylethylamine in a suitable solvent such as EtOAc, THF, DMF, DMA and DCM at a temperature from about −70 to 60° C. for about 1-24 hours.

In Step A-c, a compound of formula (V) can be prepared from a compound of formula (IV) by de-protection. De-protection can be conducted by the conventional methods known to those skilled in the art (typical amino protecting groups described in "Protective Groups in Organic Synthesis Forth Edition" edited by T. W. Greene et al. (John Wiley & Sons, 2007)).

In Step A-d, a compound of formula (VI) can be prepared from a compound of formula (V) by amidation with 2-((tert-butoxycarbonyl)amino)-2-methylpropanoic acid using a suitable condensation reagent, but not limited to, such as T3P, HBTU and EDC-HOBT. The condensation can be carried out preferably under the presence of a base such as triethylamine and N,N-diisopropylethylamine in a suitable solvent such as EtOAc, THF, DMF, DMA and DCM at a temperature from about 0 to 60° C. for about 1-24 hours.

In Step A-e, a compound of formula (I) can be prepared from a compound of formula (VI) by de-protection. De-protection can be conducted by the conventional methods known to those skilled in the art (typical amino protecting groups described in "Protective Groups in Organic Synthesis Forth Edition" edited by T. W. Greene et al. (John Wiley & Sons, 2007)).

In Step A-f, a compound of formula (VI) can be prepared from a compound of formula (III) by amidation with a compound of formula (VII-b) using a suitable condensation reagent, but not limited to, such as T3P, HBTU and EDC-HOBT. The condensation can be carried out preferably under the presence of a base such as triethylamine and N,N-diisopropylethylamine in a suitable solvent such as EtOAc, THF, DMF, DMA and DCM at a temperature from about −40 to 60° C. for about 1-24 hours.

<Scheme B>

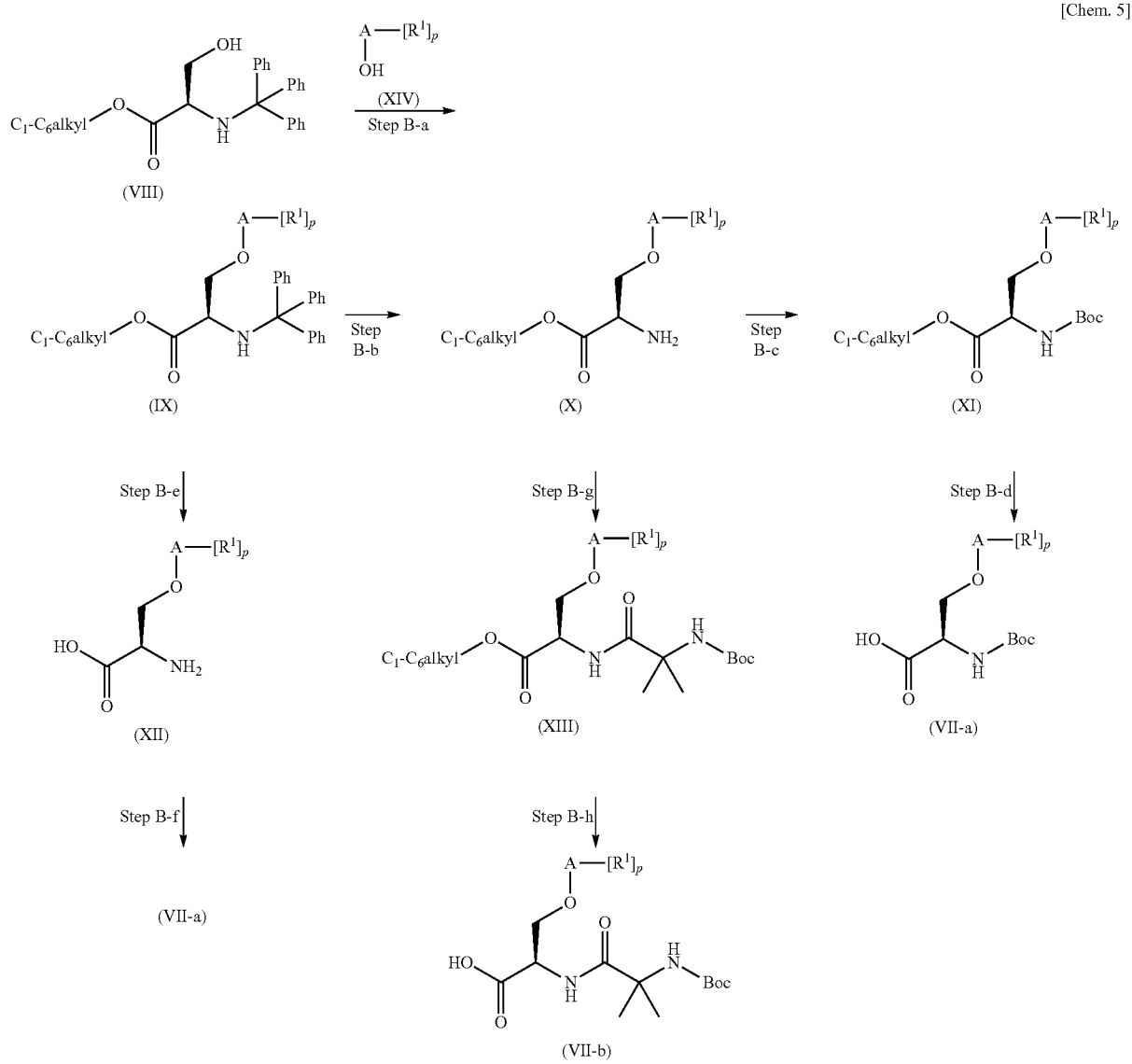

[Chem. 5]

In Step B-a, a compound of formula (IX) can be prepared from a compound of formula (VIII) by Mitsunobu reaction with a compound of formula (XIV). Mitsunobu reaction can be carried out in organic solvent in the presence of azodicarboxylate include, but not limited to, such as diethyl azodicarboxylate, diisopropyl azodicarboxylate, di-tert-butyl azodicarboxylate and bis(2-methoxyethyl) azodicarboxylate as a coupling reagent, and also in the presence of a suitable reducing agent, but not limited to, such as triphenylphosphine in an inert organic solvent. Examples of suitable inert organic solvent include such as THF, 1,4-dioxane, MeCN, TBME, and toluene. The reaction can be carried out at a temperature from about −20 to 150° C., more preferably from about 0 to 60° C. Reaction times are, in general, from about 30 minutes to 48 hours, more preferably from about 30 minutes to 24 hours.

In Step B-b, a compound of formula (X) can be prepared from a compound of formula (IX) by de-protection. De-protection can be conducted by the conventional methods known to those skilled in the art (typical amino protecting groups described in "Protective Groups in Organic Synthesis Forth Edition" edited by T. W. Greene et al. (John Wiley & Sons, 2007)).

In Step B-c, a compound of formula (XI) can be prepared from a compound of formula (X) by protection of amino moiety. Protection can be carried out by the conventional methods known to those skilled in the art (typical amino protecting groups described in "Protective Groups in Organic Synthesis Forth Edition" edited by T. W. Greene et al. (John Wiley & Sons, 2007)).

In Step B-d, a compound of formula (VII-a) can be prepared by hydrolysis of the ester compound of formula (XI). The hydrolysis can be carried out by the conventional procedures. In a typical procedure, the hydrolysis is carried out under basic conditions, e.g. in the presence of sodium hydroxide, potassium hydroxide or lithium hydroxide. Suitable solvents include, but not limited to, water, methanol, ethanol, propanol, butanol, 2-methoxyethanol, ethylene glycol, THF, DME, 1,4-dioxane, DMF, and DMA. The reaction can be carried out at a temperature from about 20 to 100° C. for from about 10 min to 24 hrs.

In Step B-e, a compound of formula (XII) can be prepared by the treatment under acidic conditions. In a typical procedure, the reaction can be carried out under acidic conditions, e.g. in the presence of hydrochloric acid, hydrobromic acid. Suitable solvents include, but not limited to, water, 1,4-dioxane, THF, MeCN. The reaction can be carried out at a temperature from about 50 to 120° C. for from about 1 hr to 24 hrs.

In Step B-f, a compound of formula (VII-a) can be prepared from a compound of formula (XII) by protection of amino moiety. Protection can be carried out by the conventional methods known to those skilled in the art (typical amino protecting groups described in "Protective Groups in Organic Synthesis Forth Edition" edited by T. W. Greene et al. (John Wiley & Sons, 2007)).

In Step B-g, a compound of formula (XIII) can be prepared from a compound of formula (X) by protection of amino moiety. Protection can be carried out by the conventional methods known to those skilled in the art (typical amino protecting groups described in "Protective Groups in Organic Synthesis Forth Edition" edited by T. W. Greene et al. (John Wiley & Sons, 2007)).

In Step B-h, a compound of formula (VII-b) can be prepared by hydrolysis of the ester compound of formula (XIII) The hydrolysis can be carried out by the conventional procedures. In a typical procedure, the hydrolysis is carried out under basic conditions, e.g. in the presence of sodium hydroxide, potassium hydroxide or lithium hydroxide. Suitable solvents include, but not limited to, water, methanol, ethanol, propanol, butanol, 2-methoxyethanol, ethylene glycol, THF, DME, 1,4-dioxane, DMF, and DMA. The reaction can be carried out at a temperature from about 20 to 100° C. for from about 10 min to 24 hrs.

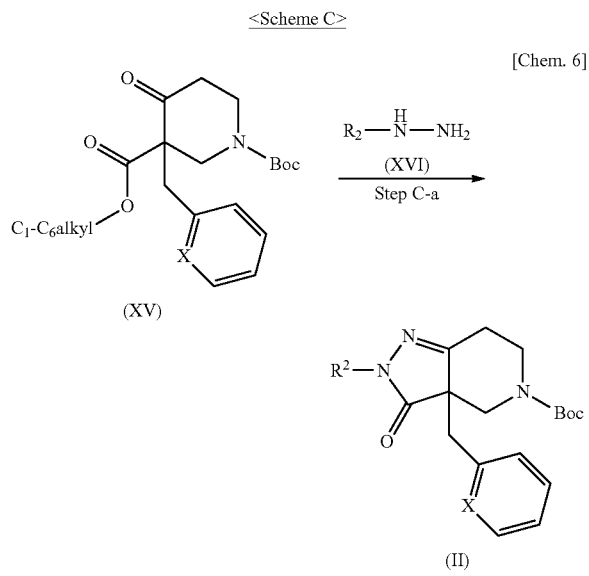

<Scheme C>

[Chem. 6]

(XV)

(II)

In Step C-a, a compound of formula (II) can be prepared from a compound of formula (XV) by in situ hydrazone formation with a compound of formula (XVI) followed by ring closure. The reaction can be carried out in the presence of metal acetate include, but not limited to, such as sodium acetate, potassium acetate, and lithium acetate. Suitable solvents include, but not limited to, methanol, ethanol, propanol, butanol, 2-methoxyethanol, ethylene glycol, THF, DME, and 1,4-dioxane. The reaction can be carried out at a temperature from about 50 to 150° C. for from about 1 hr to 48 hrs.

All starting materials in the following general syntheses may be commercially available or obtained by the conventional methods known to those skilled in the art, otherwise noted in the intermediate synthesis part.

Nucleus Synthesis Part

Nucleus compounds are prepared as follows. Names and structures of the nucleus compounds are shown in Table 3.

Nucleus 1

3a-benzyl-2-(2,2-difluoroethyl)-4,5,6,7-tetrahydro-2H-pyrazolo[4,3-c]pyridin-3(3aH)-one 2,2,2-trifluoroacetate Step 1: tert-butyl 3a-benzyl-2-(2,2-difluoroethyl)-3-oxo-3a,4,6,7-tetrahydro-2H-pyrazolo[4,3-c]pyridine-5(3H)-carboxylate A mixture of 1-tert-butyl 3-methyl 3-benzyl-4-oxopiperidine-1,3-dicarboxylate (2.4 g, 7.0 mmol), (2,2-difluoroethyl)hydrazine hydrochloride (930 mg, 7.0 mmol), and sodium acetate (2.3 g, 28 mmol) in EtOH (40 mL) was stirred for 24 hrs at reflux temperature. After cooled to room temperature, the mixture was concentrated in vacuo. The residue was diluted with EtOAc (80 mL). The diluted mixture was washed with water, and was dried over $Na_2SO_4$. After filtration, the filtrate was concentrated in vacuo. The residue was purified by column chromatography (silica gel, eluted with 25% EtOAc in hexane) to give the title compound as a white solid (1.8 g, 65% yield). MS (ESI) m/z: 394 $(M+H)^+$ Step 2

3a-benzyl-2-(2,2-difluoroethyl)-4,5,6,7-tetrahydro-2H-pyrazolo[4,3-c]pyridin-3(3aH)-one 2,2,2-trifluoroacetate To a solution of tert-butyl 3a-benzyl-2-(2,2-difluoroethyl)-3-oxo-3a,4,6,7-tetrahydro-2H-pyrazolo[4,3-c]pyridine-5(3H)-carboxylate (100 mg, 0.25 mmol) in DCM (3 mL) was added trifluoroacetic acid (2 mL) at 0° C., and the mixture was stirred for 1 hr at the same temperature. The mixture was concentrated in vacuo to give the title compound as a pale yellow gum (104 mg, >99% yield).

MS (ESI) m/z: 294 $(M+H)^+$, 292 (M−H)

Nucleus 2

(R)-2-(2,2-difluoroethyl)-3a-(pyridin-2-ylmethyl)-4,5,6,7-tetrahydro-2H-pyrazolo[4,3-c]pyridin-3(3aH)-one (2S,3S)-2,3-dihydroxysuccinate Step 1: tert-butyl 2-(2,2-difluoroethyl)-3-oxo-3a-(pyridin-2-ylmethyl)-3a,4,6,7-tetrahydro-2H-pyrazolo[4,3-c]pyridine-5(3H)-carboxylate The title compound was prepared in 87% yield (3600 mg, pale purple gum) from 1-tert-butyl 3-methyl 4-oxo-3-(pyridin-2-ylmethyl)piperidine-1,3-dicarboxylate (3700 mg, 11 mmol) in a similar manner to Step 1 of Nucleus 1.

$^1$H-NMR (270 MHz, CDCl$_3$) delta 8.38 (1H, d, J=3.9 Hz), 7.58-7.50 (1H, m), 7.13-7.05 (2H, m), 5.94-5.30 (1H, m), 4.75-4.40 (2H, br), 4.10-3.76 (2H, m), 3.42-3.26 (2H, m), 2.93-2.50 (4H, m), 1.53 (9H, s).

MS (ESI) m/z: 395 (M+H)$^+$.

Step 2

(R)-2-(2,2-difluoroethyl)-3a-(pyridin-2-ylmethyl)-4, 5,6,7-tetrahydro-2H-pyrazolo[4,3-c]pyridin-3(3aH)-one To a solution of tert-butyl 2-(2,2-difluoroethyl)-3-oxo-3a-(pyridin-2-ylmethyl)-3a,4,6,7-tetrahydro-2H-pyrazolo[4,3-c]pyridine-5(3H)-carboxylate (4.9 g, 13 mmol, racemic) in DCM (50 mL) was cooled to 0° C., and trifluoroacetic acid (4.1 mL) was added slowly. The mixture was stirred at room temperature for 1.5 hrs, and then cooled to 0° C. To the resulting suspension was added triethylamine (9.6 mL, 69 mmol) at the same temperature. The resulting yellow, clear solution was diluted with DCM (50 mL), washed with brine (30 mL×3), dried over Na$_2$SO$_4$, filtered, and concentrated in vacuo to give the title compound as a brown oil (3.8 g, >100% yield).

MS (ESI) m/z: 295 (M+H)$^+$.

$^1$H-NMR (270 MHz, CDCl$_3$) delta 8.41 (1H, d, J=5.9 Hz), 7.58-7.51 (1H, m), 7.14-7.06 (2H, m), 5.76 (1H, tt, J=55.7 Hz, 4.6 Hz), 4.16-3.72 (2H, m), 3.53-3.32 (4H, m), 2.74-2.52 (4H, m). NH was not observed.

MS (ESI) m/z: 295 (M+H)$^+$.

Step 3

(R)-2-(2,2-difluoroethyl)-3a-(pyridin-2-ylmethyl)-4, 5,6,7-tetrahydro-2H-pyrazolo[4,3-c]pyridin-3(3aH)-one (2S,3S)-2,3-dihydroxysuccinate A solution of (R)-2-(2,2-difluoroethyl)-3a-(pyridin-2-ylmethyl)-4,5,6,7-tetrahydro-2H-pyrazolo[4,3-c]pyridin-3 (3aH)-one (ca. 12.5 mmol) was dissolved in DCM (6 mL) and acetone (20 mL). To the mixture was added a solution of D-tartaric acid (2.07 g, 13.8 mmol) in acetone-water (7:3, 10 mL) at room temperature. The mixture was immediately changed to white slurry. Acetone (10 mL) was added again to make stirring of the mixture easier. After stirring at room temperature overnight, the mixture was filtered and the solid was washed with cold acetone (10 mL) and dried under reduced pressure at 40° C. for 3 hours to afford the title compound as a white solid (4.68 g, 84%).

$^1$H NMR (DMSO-d$_6$, 270 MHz) delta 8.33 (1H, d, J=5.9 Hz), 7.66-7.60 (1H, m), 7.19-7.08 (2H, m), 5.96 (1H, tt, J=55.3 Hz, 4.0 Hz), 4.28 (2H, s), 4.03-3.74 (2H, m), 3.62 (1H, d, J=14.1 Hz), 3.41-3.18 (4H, m), 3.14 (1H, d, J=14.1 Hz), 2.50-2.33 (2H, m).

MS (ESI) m/z: 295 (M+H)$^+$.

TABLE 3

| Nucleus | Name | Structure |
|---|---|---|
| 1 | 3a-benzyl-2-(2,2-difluoroethyl)-4,5,6,7-tetrahydro-2H-pyrazolo[4,3-c]pyridin-3(3aH)-one 2,2,2-trifluoroacetate | 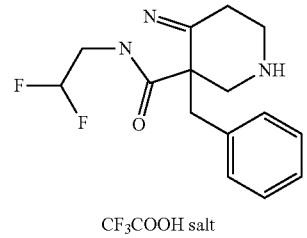 [SMILES: N=C1CCNCC1(Cc1ccccc1)C(=O)NCC(F)F]<br>CF$_3$COOH salt |
| 2 | (R)-2-(2,2-difluoroethyl)-3a-(pyridin-2-ylmethyl)-4,5,6,7-tetrahydro-2H-pyrazolo[4,3-c]pyridin-3(3aH)-one (2S,3S)-2,3-dihydroxysuccinate | 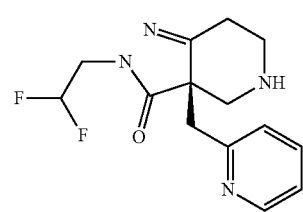<br>D-tartaric acid salt |

Intermediate Synthesis Part

Intermediate compounds are prepared as follows. Names and structures of the intermediate compounds are shown in Table 4.

Intermediate 1

(R)-2-((tert-butoxycarbonyl)amino)-3-(2,4-difluorophenoxy)propanoic acid

Step 1: (R)-methyl 3-(2,4-difluorophenoxy)-2-(tritylamino)propanoate

To a stirred solution of (R)-methyl 3-hydroxy-2-(tritylamino)propanoate (800 mg, 2.2 mmol), 2,4-difluorophenol (370 mg, 2.9 mmol), and triphenylphosphine (760 mg, 2.9 mmol) in THF (15 mL) was added dropwise a solution of bis(2-methoxyethyl) azodicarboxylate (670 mg, 2.9 mmol) in THF (2 mL) at 0° C. The mixture was stirred at room temperature for 2 hrs. The mixture was concentrated, and the residue was diluted with EtOAc (50 mL). The diluted mixture was washed with a saturated aqueous NaHCO$_3$ solution and then brine, and was dried over Na$_2$SO$_4$. After filtration, the filtrate was concentrated. The residue was purified by column chromatography (silica gel, eluted with 3% to 13% EtOAc in hexane) to give the title compound as a colorless gum (771 mg, 74% yield).

$^1$H NMR (300 MHz, CDCl$_3$) delta 7.52 (6H, d, J=7.3 Hz), 7.30-7.16 (9H, m), 6.99-6.72 (3H, m), 4.29 (1H, d, J=9.5, 5.2 Hz), 4.02 (1H, dd, J=9.5, 6.9 Hz), 3.78-3.71 (1H, m), 3.24 (3H, s), 2.88 (1H, d, J=10.3 Hz).

MS (ESI) m/z: fragment signal of 243 (positive ion) was observed.

Step 2: (R)-methyl 2-((tert-butoxycarbonyl)amino)-3-(2,4-difluorophenoxy)propanoate To a stirred solution of (R)-methyl 3-(2,4-difluorophenoxy)-2-(tritylamino)propanoate (760 mg, 1.6 mmol) in DCM (10 mL) was added trifluoroacetic acid (3.7 mL) at room temperature, and the mixture was stirred for 2 hrs at the same temperature. To the mixture was added MeOH (25 mL) and the resulting mixture was stirred for 5 min, and then concentrated in vacuo. The residue was dissolved in DCM (20 mL), and then, triethylamine (0.67 mL, 4.8 mmol) and di-tert-butyl dicarbonate (530 mg, 2.4 mmol) were added to the mixture successively at room temperature. After stirring for 2 hrs at room temperature, the mixture was concentrated in vacuo. The residue was purified by column chromatography (silica gel, eluted with 5% to 14% EtOAc in hexane) to give the title compound as a colorless oil (470 mg, 88% yield).

$^1$H NMR (300 MHz, CDCl$_3$) delta 6.96-6.75 (3H, m), 5.53 (1H, d, J=8.8 Hz), 4.66-4.63 (1H, m), 4.42 (1H, dd, J=8.8, 2.9 Hz), 4.25 (1H, dd, J=9.2, 3.3 Hz), 3.79 (3H, s), 1.46 (9H, s).

MS (ESI) m/z: 232 (M−Boc+H)$^+$.

Step 3: (R)-2-((tert-butoxycarbonyl)amino)-3-(2,4-difluorophenoxy)propanoic acid To a stirred solution of (R)-methyl 2-((tert-butoxycarbonyl)amino)-3-(2,4-difluorophenoxy)propanoate (470 mg, 1.4 mmol) in THF (10 mL) was added LiOH monohydrate (65 mg, 1.6 mmol), and then water (2 mL) was added to the mixture. The mixture was stirred for 30 min at room temperature. To the mixture was added 0.5N hydrochloric acid (2 mL), and the mixture was extracted with EtOAc (50 mL×2). The extract was dried over Na$_2$SO$_4$. After filtration, the filtrate was concentrated in vacuo. The residue was purified by column chromatography (silica gel, eluted with 9% MeOH in DCM) to give the title compound as a colorless gum (200 mg, 45% yield).

MS (ESI) m/z: 318 (M+H)$^+$, 316 (M−H)$^-$.

Intermediate 2: (R)-2-((tert-butoxycarbonyl)amino)-3-phenoxypropanoic acid

Step 1: (R)-methyl 3-phenoxy-2-(tritylamino)propanoate

The title compound was prepared in 23% yield (390 mg, colorless gum) from (R)-methyl 3-hydroxy-2-(tritylamino) propanoate (1.4 g, 3.9 mmol) and phenol (0.73 g, 7.8 mmol) in a similar manner to Step 1 of Intermediate 1.

$^1$H NMR (300 MHz, CDCl$_3$) delta 7.54-7.49 (6H, m), 7.30-7.16 (11H, m), 6.96 (1H, t, J=7.3 Hz), 6.88 (2H, d, J=8.0 Hz) 4.26 (1H, dd, J=9.2, 4.8 Hz), 4.03-4.00 (1H, m), 3.76-3.72 (1H, m), 3.22 (3H, s), 2.88 (1H, br s).

MS (ESI) m/z: fragment signal of 243 (positive ion) was observed.

Step 2: (R)-methyl 2-((tert-butoxycarbonyl)amino)-3-phenoxypropanoate

The title compound was prepared in 87% yield (230 mg, colorless gum) from (R)-methyl 3-phenoxy-2-(tritylamino) propanoate (390 mg, 0.89 mmol) in a similar manner to Step 2 of Intermediate 1.

$^1$H NMR (300 MHz, CDCl$_3$) delta 7.28 (2H, t, J=7.7 Hz), 6.98 (1H, t, J=7.3 Hz), 6.88 (2H, d, J=8.1 Hz), 5.52 (1H, d, J=8.0 Hz), 4.67 (1H, dt, J=8.8, 2.6 Hz), 4.40 (1H, dd, J=9.2, 2.7 Hz), 4.20 (1H, dd, J=9.5, 2.9 Hz), 3.77 (3H, s), 1.49 (9H, s).

MS (ESI) m/z: 232 (M−Boc+H)$^+$.

Step 3: (R)-2-((tert-butoxycarbonyl)amino)-3-phenoxypropanoic acid

The title compound was prepared in 73% yield (150 mg, colorless gum) from (R)-methyl 2-((tert-butoxycarbonyl) amino)-3-phenoxypropanoate (220 mg, 0.75 mmol) in a similar manner to Step 3 of Intermediate 1.

MS (ESI) m/z: 282 (M+H)$^+$, 280 (M−H)$^-$.

Intermediate 3: (R)-2-((tert-butoxycarbonyl)amino)-3-(4-chlorophenoxy)propanoic acid

Step 1: (R)-methyl 3-(4-chlorophenoxy)-2-(tritylamino)propanoate

The title compound was prepared in 56% yield (730 mg, colorless gum) from (R)-methyl 3-hydroxy-2-(tritylamino) propanoate (1.0 g, 2.8 mmol) and 4-chlorophenol (0.46 g, 3.6 mmol) in a similar manner to Step 1 of Intermediate 1.

$^1$H NMR (300 MHz, CDCl$_3$) delta 7.53-7.49 (6H, m), 7.28-7.16 (11H, m), 6.82-6.77 (2H, m), 4.20 (1H, dd, J=9.2, 4.8 Hz), 4.00-3.95 (1H, m), 3.80-3.67 (1H, m), 3.23 (3H, s), 2.87 (1H, d, J=10.3 Hz).

MS (ESI) m/z: fragment signal of 243 (positive ion) was observed.

Step 2: (R)-methyl 2-((tert-butoxycarbonyl)amino)-3-(4-chlorophenoxy)propanoate The title compound was prepared in 95% yield (480 mg, colorless gum) from (R)-methyl 3-(4-chlorophenoxy)-2-(tritylamino)propanoate (720 mg, 1.5 mmol) in a similar manner to Step 2 of Intermediate 1.

$^1$H NMR (300 MHz, CDCl$_3$) delta 7.23 (2H, d, J=8.8 Hz), 6.81 (2H, d, J=9.5 Hz), 5.49 (1H, d, J=8.1 Hz), 4.74-4.61 (1H, m), 4.37 (1H, dd, J=9.2, 2.7 Hz), 4.18 (1H, dd, J=9.5, 2.9 Hz), 3.72 (3H, s), 1.46 (9H, s).

MS (ESI) m/z: 230 (M−Boc+H)$^+$.

Step 3: (R)-2-((tert-butoxycarbonyl)amino)-3-(4-chlorophenoxy)propanoic acid The title compound was prepared in 58% yield (260 mg, colorless gum) from (R)-methyl 2-((tert-butoxycarbonyl) amino)-3-(4-chlorophenoxy)propanoate (480 mg, 1.4 mmol) in a similar manner to Step 3 of Intermediate 1.

MS (ESI) m/z: 316 (M+H)$^+$, 314 (M−H)$^-$.

Intermediate 4: (R)-2-((tert-butoxycarbonyl)amino)-3-(3-chlorophenoxy)propanoic acid

Step 1: (R)-methyl 3-(3-chlorophenoxy)-2-(tritylamino)propanoate

The title compound was prepared in 76% yield (890 mg, colorless gum) from (R)-methyl 3-hydroxy-2-(tritylamino) propanoate (900 mg, 2.5 mmol) and 3-chlorophenol (420 mg, 3.2 mmol) in a similar manner to Step 1 of Intermediate 1.

$^1$H NMR (300 MHz, CDCl$_3$) delta 7.53-7.13 (16H, m), 6.95-6.70 (3H, m), 4.23 (1H, dd, J=9.2, 4.7 Hz), 3.99 (1H, dd, J=9.5, 6.6 Hz), 3.77-3.68 (1H, m), 3.23 (3H, s), 2.88 (1H, d, J=10.3 Hz).

MS (ESI) m/z: fragment signal of 243 (positive ion) was observed.

Step 2: (R)-methyl 2-((tert-butoxycarbonyl)amino)-3-(3-chlorophenoxy)propanoate The title compound was prepared in 73% yield (450 mg, colorless oil) from (R)-methyl 3-(3-chlorophenoxy)-2-(tritylamino)propanoate (880 mg, 1.8 mmol) in a similar manner to Step 2 of Intermediate 1.

$^1$H NMR (300 MHz, CDCl$_3$) delta 7.20 (1H, t, J=8.1 Hz), 6.96 (1H, d, J=8.0 Hz), 6.89 (1H, t, J=2.2 Hz), 6.77 (1H, dd, J=8.4, 2.6 Hz), 5.49 (1H, d, J=4.4 Hz), 4.69-4.65 (1H, m), 4.38 (1H, dd, J=9.2, 2.6 Hz), 4.20 (1H, dd, J=8.8, 2.9 Hz), 3.78 (3H, s), 1.46 (9H, s).

MS (ESI) m/z: 230 (M−Boc+H)$^+$.

Step 3: (R)-2-((tert-butoxycarbonyl)amino)-3-(3-chlorophenoxy)propanoic acid

The title compound was prepared in 57% yield (240 mg, colorless gum) from (R)-methyl 2-((tert-butoxycarbonyl)amino)-3-(3-chlorophenoxy)propanoate (440 mg, 1.3 mmol) in a similar manner to Step 3 of Intermediate 1.

MS (ESI) m/z: 316 (M+H)$^+$, 314 (M−H)$^-$.

Intermediate 5

(R)-2-((tert-butoxycarbonyl)amino)-3-(3,5-dichlorophenoxy)propanoic acid

Step 1: (R)-methyl 3-(3,5-dichlorophenoxy)-2-(tritylamino)propanoate

The title compound was prepared in 42% yield (530 mg, colorless solid) from (R)-methyl 3-hydroxy-2-(tritylamino)propanoate (900 mg, 2.5 mmol) and 3,5-dichlorophenol (530 mg, 3.2 mmol) in a similar manner to Step 1 of Intermediate 1.

$^1$H NMR (300 MHz, CDCl$_3$) delta 7.51 (6H, d, J=7.3 Hz), 7.35-7.17 (9H, m), 6.98-6.95 (1H, br s), 6.78 (2H, d, J=1.5 Hz), 4.21 (1H, dd, J=9.2, 4.8 Hz), 3.97 (1H, dd, J=8.8, 6.6 Hz), 3.74-3.67 (1H, m), 3.25 (3H, s), 2.88 (1H, d, J=10.3 Hz).

MS (ESI) m/z: fragment signal of 243 (positive ion) was observed.

Step 2: (R)-methyl 2-((tert-butoxycarbonyl)amino)-3-(3,5-dichlorophenoxy)propanoate The title compound was prepared in 85% yield (320 mg, colorless gum) from (R)-methyl 3-(3,5-dichlorophenoxy)-2-(tritylamino)propanoate (520 mg, 1.0 mmol) in a similar manner to Step 2 of Intermediate 1.

$^1$H NMR (300 MHz, CDCl$_3$) delta 6.98 (1H, d, J=1.5 Hz), 6.79 (2H, d, J=1.5 Hz), 5.45 (1H, d, J=8.8 Hz), 4.68-4.65 (1H, m), 4.37 (1H, dd, J=8.8, 1.5 Hz), 4.20 (1H, dd, J=9.2, 2.6 Hz), 3.79 (3H, s), 1.46 (9H, s).

MS (ESI) m/z: 264 (M−Boc+H)$^+$.

Step 3: (R)-2-((tert-butoxycarbonyl)amino)-3-(3,5-dichlorophenoxy)propanoic acid The title compound was prepared in 48% yield (140 mg, colorless gum) from (R)-methyl 2-((tert-butoxycarbonyl)amino)-3-(3,5-dichlorophenoxy)propanoate (310 mg, 0.85 mmol) in a similar manner to Step 3 of Intermediate 1.

MS (ESI) m/z: 250 (M−Boc+H)$^+$, 348 (M−H)$^-$.

Intermediate 6

(R)-2-((tert-butoxycarbonyl)amino)-3-(2-(trifluoromethyl)phenoxy)propanoic acid

Step 1: (R)-methyl 3-(2-(trifluoromethyl)phenoxy)-2-(tritylamino)propanoate

The title compound was prepared in 55% yield (690 mg, colorless gum) from (R)-methyl 3-hydroxy-2-(tritylamino)propanoate (900 mg, 2.5 mmol) and 2-(trifluoromethyl)phenol (530 mg, 3.2 mmol) in a similar manner to Step 1 of Intermediate 1.

$^1$H NMR (300 MHz, CDCl$_3$) delta 7.56-7.46 (7H, m), 7.30-7.17 (10H, m), 7.04-6.96 (2H, m), 4.36 (1H, dd, J=8.8, 3.6 Hz), 4.07-4.02 (1H, m), 3.82-3.74 (1H, m), 3.22 (3H, s), 2.92 (1H, d, J=10.3 Hz).

MS (ESI) m/z: fragment signal of 243 (positive ion) was observed.

Step 2: (R)-methyl 2-((tert-butoxycarbonyl)amino)-3-(2-(trifluoromethyl)phenoxy)propanoate The title compound was prepared in 86% yield (420 mg, colorless oil) from (R)-methyl 3-(2-(trifluoromethyl)phenoxy)-2-(tritylamino)propanoate (680 mg, 1.3 mmol) in a similar manner to Step 2 of Intermediate 1.

$^1$H NMR (300 MHz, CDCl$_3$) delta 7.56 (1H, d, J=8.1 Hz), 7.49 (1H, t, J=8.1 Hz), 7305 (1H, t, J=7.3 Hz), 6.96 (1H, d, J=8.1 Hz), 5.51 (1H, d, J=8.8 Hz), 4.72 (1H, dt, J=8.8, 2.6 Hz), 4.48 (1H, dd, J=8.8, 2.2 Hz), 4.30 (1H, dd, J=9.2, 2.6 Hz), 3.78 (3H, s), 1.46 (9H, s).

MS (ESI) m/z: 364 (M+H)$^+$.

Step 3: (R)-2-((tert-butoxycarbonyl)amino)-3-(2-(trifluoromethyl)phenoxy)propanoic acid The title compound was prepared in 55% yield (220 mg, colorless gum) from (R)-methyl 2-((tert-butoxycarbonyl)amino)-3-(2-(trifluoromethyl)phenoxy)propanoate (410 mg, 1.1 mmol) in a similar manner to Step 3 of Intermediate 1.

MS (ESI) m/z: 250 (M−Boc+H)$^+$, 348 (M−H)$^-$.

Intermediate 7

(R)-2-((tert-butoxycarbonyl)amino)-3-(3,4-difluorophenoxy)propanoic acid

Step 1: (R)-methyl 3-(3,4-difluorophenoxy)-2-(tritylamino)propanoate

The title compound was prepared in 56% yield (660 mg, colorless gum) from (R)-methyl 3-hydroxy-2-(tritylamino)propanoate (900 mg, 2.5 mmol) and 3,4-difluorophenol (420 mg, 3.2 mmol) in a similar manner to Step 1 of Intermediate 1.

$^1$H NMR (300 MHz, CDCl$_3$) delta 7.52-7.49 (6H, m), 7.30-7.17 (9H, m), 7.05 (1H, q, J=9.3 Hz), 6.73-6.65 (1H, m), 6.59-6.53 (1H, m), 4.17 (1H, dd, J=9.5, 5.1 Hz), 3.94 (1H, dd, J=9.5, 6.6 Hz), 3.73-3.66 (1H, m), 3.24 (3H, s), 2.87 (1H, d, J=10.3 Hz).

MS (ESI) m/z: fragment signal of 243 (positive ion) was observed.

Step 2: (R)-methyl 2-((tert-butoxycarbonyl)amino)-3-(3,4-difluorophenoxy)propanoate The title compound was prepared in 81% yield (370 mg, colorless oil) from (R)-methyl 3-(3,4-difluorophenoxy)-2-(tritylamino)propanoate (650 mg, 1.4 mmol) in a similar manner to Step 2 of Intermediate 1.

$^1$H NMR (300 MHz, CDCl$_3$) delta 7.06 (1H, q, J=9.3 Hz), 6.75-6.67 (1H, m), 6.61-6.55 (1H, m), 5.46 (1H, d, J=8.0 Hz), 4.70-4.61 (1H, m), 4.34 (1H, dd, J=8.8, 2.9 Hz), 4.16 (1H, dd, J=9.5, 2.9 Hz), 3.78 (3H, s), 1.46 (9H, s).

MS (ESI) m/z: 332 (M+H)$^+$.

Step 3: (R)-2-((tert-butoxycarbonyl)amino)-3-(3,4-difluorophenoxy)propanoic acid The title compound was prepared in 57% yield (200 mg, pale brown gum) from (R)-methyl 2-((tert-butoxycarbonyl)amino)-3-(3,4-difluorophenoxy)propanoate (360 mg, 1.1 mmol) in a similar manner to Step 3 of Intermediate 1.

MS (ESI) m/z: 318 (M−Boc+H)$^+$, 316 (M−H)$^−$.

Intermediate 8: (R)-2-((tert-butoxycarbonyl)amino)-3-(2-chlorophenoxy)propanoic acid

Step 1: (R)-methyl 3-(2-chlorophenoxy)-2-(tritylamino)propanoate

The title compound was prepared in 68% yield (880 mg, colorless solid) from (R)-methyl 3-hydroxy-2-(tritylamino)propanoate (1000 mg, 2.8 mmol) and 2-chlorophenol (460 mg, 3.2 mmol) in a similar manner to Step 1 of Intermediate 1.

$^1$H NMR (300 MHz, CDCl$_3$) delta 7.53 (6H, d, J=7.3 Hz), 7.36-6.92 (11H, m), 6.93-6.88 (2H, m), 4.35 (1H, dd, J=8.8, 5.1 Hz), 4.05-3.99 (1H, m), 3.85-3.78 (1H, m), 3.24 (3H, s), 2.91 (1H, d, J=10.3 Hz).

MS (ESI) m/z: 494 (M+Na+H)$^+$.

Step 2: (R)-methyl 2-((tert-butoxycarbonyl)amino)-3-(2-chlorophenoxy)propanoate The title compound was prepared in 90% yield (550 mg, colorless oil) from (R)-methyl 3-(2-chlorophenoxy)-2-(tritylamino)propanoate (870 mg, 1.8 mmol) in a similar manner to Step 2 of Intermediate 1.

$^1$H NMR (300 MHz, CDCl$_3$) delta 7.35 (1H, dd, J=8.1, 1.5 Hz), 7.21 (1H, td, J=7.7, 1.5 Hz), 6.96-6.90 (2H, m), 5.60 (1H, d, J=8.8 Hz), 4.76-4.66 (1H, m), 4.45 (1H, dd, J=9.2, 2.6 Hz), 4.27 (1H, dd, J=9.5, 2.9 Hz), 3.80 (3H, s), 1.46 (9H, s).

MS (ESI) m/z: 330 (M+H)$^+$.

Step 3: (R)-2-((tert-butoxycarbonyl)amino)-3-(2-chlorophenoxy)propanoic acid The title compound was prepared in 51% yield (260 mg, colorless gum) from (R)-methyl 2-((tert-butoxycarbonyl)amino)-3-(2-chlorophenoxy)propanoate (540 mg, 1.6 mmol) in a similar manner to Step 3 of Intermediate 1.

MS (ESI) m/z: 216 (M−Boc+H)$^+$, 314 (M−H)$^−$.

Intermediate 9 (R)-3-(3,5-bis(trifluoromethyl)phenoxy)-2-((tert-butoxycarbonyl)amino)propanoic acid

Step 1: (R)-methyl 3-(3,5-bis(trifluoromethyl)phenoxy)-2-(tritylamino)propanoate The title compound was prepared in 35% yield (550 mg, colorless gum) from (R)-methyl 3-hydroxy-2-(tritylamino)propanoate (1000 mg, 2.8 mmol) and 3,5-bis(trifluoromethyl)phenol (830 mg, 3.6 mmol) in a similar manner to Step 1 of Intermediate 1.

$^1$H NMR (300 MHz, CDCl$_3$) delta 7.52 (6H, d, J=7.3 Hz), 7.34-7.18 (12H, m), 4.28 (1H, dd, J=9.5, 4.4 Hz), 4.03 (1H, dd, J=9.5, 6.6 Hz), 3.81-3.70 (1H, m), 3.28 (3H, s), 2.93 (1H, d, J=9.5 Hz).

MS (ESI) m/z: fragment signal of 243 (positive ion) was observed.

Step 2: (R)-methyl 3-(3,5-bis(trifluoromethyl)phenoxy)-2-((tert-butoxycarbonyl)amino)propanoate The title compound was prepared in 96% yield (390 mg, colorless oil) from (R)-methyl 3-(3,5-bis(trifluoromethyl)phenoxy)-2-(tritylamino)propanoate (540 mg, 0.94 mmol) in a similar manner to Step 2 of Intermediate 1.

$^1$H NMR (300 MHz, CDCl$_3$) delta 7.50 (1H, s), 7.31 (2H, s), 5.50 (1H, d, J=8.0 Hz), 4.79-4.69 (1H, m), 4.49 (1H, dd, J=9.1, 2.6 Hz), 4.33 (1H, 8.8, 2.9 Hz), 3.81 (3H, s), 1.46 (9H, s).

MS (ESI) m/z: 432 (M+H)$^+$.

Step 3 (R)-3-(3,5-bis(trifluoromethyl)phenoxy)-2-((tert-butoxycarbonyl)amino)propanoic acid The title compound was prepared in 30% yield (110 mg, colorless gum) from (R)-methyl 3-(3,5-bis(trifluoromethyl)phenoxy)-2-((tert-butoxycarbonyl)amino)propanoate (380 mg, 0.88 mmol) in a similar manner to Step 3 of Intermediate 1.

MS (ESI) m/z: 418 (M+H)$^+$, 416 (M−H)$^−$.

Intermediate 10: (R)-2-((tert-butoxycarbonyl)amino)-3-(3-fluorophenoxy)propanoic acid

Step 1: (R)-methyl 3-(3-fluorophenoxy)-2-(tritylamino)propanoate

The title compound was prepared in 74% yield (1400 mg, colorless gum) from (R)-methyl 3-hydroxy-2-(tritylamino)propanoate (1500 mg, 4.2 mmol) and 3-fluorophenol (610 mg, 5.4 mmol) in a similar manner to Step 1 of Intermediate 1.

$^1$H NMR (300 MHz, CDCl$_3$) delta 7.60-7.48 (6H, m), 7.31-7.15 (10H, m), 6.70-6.55 (3H, m), 4.22 (1H, dd, J=9.9, 5.3 Hz), 3.99 (1H, dd, J=9.2, 6.6 Hz), 3.76-3.68 (1H, m), 3.23 (3H, s), 2.88 (1H, d, J=10.5 Hz).

MS (ESI) m/z: 478 (M+Na)$^+$.

Step 2: (R)-methyl 2-((tert-butoxycarbonyl)amino)-3-(3-fluorophenoxy)propanoate The title compound was prepared in 77% yield (290 mg, colorless oil) from (R)-methyl 3-(3-fluorophenoxy)-2-(tritylamino)propanoate (550 mg, 1.2 mmol) in a similar manner to Step 2 of Intermediate 1.

$^1$H NMR (300 MHz, CDCl$_3$) delta 7.26-7.18 (1H, m), 6.72-6.57 (3H, m), 5.48 (1H, d, J=7.9 Hz), 4.72-4.62 (1H, m), 4.38 (1H, dd, J=9.2, 2.6 Hz), 4.20 (1H, dd, J=9.2, 3.3 Hz), 3.78 (3H, s), 1.46 (9H, s).

MS (ESI) m/z: 314 (M+H)$^+$.

Step 3: (R)-2-((tert-butoxycarbonyl)amino)-3-(3-fluorophenoxy)propanoic acid The title compound was prepared in 29% yield (80 mg, colorless gum) from (R)-methyl 2-((tert-butoxycarbonyl)amino)-3-(3-fluorophenoxy)propanoate (290 mg, 0.93 mmol) in a similar manner to Step 3 of Intermediate 1.

MS (ESI) m/z: 300 (M+H)$^+$, 298 (M−H)$^−$.

Intermediate 11

(R)-2-((tert-butoxycarbonyl)amino)-3-(3-methoxyphenoxy)propanoic acid

Step 1: (R)-methyl 3-(3-methoxyphenoxy)-2-(tritylamino)propanoate

The title compound was prepared in 43% yield (830 mg, colorless gum) from (R)-methyl 3-hydroxy-2-(tritylamino)propanoate (1500 mg, 4.2 mmol) and 3-methoxyphenol (670 mg, 5.4 mmol) in a similar manner to Step 1 of Intermediate 1.

$^1$H NMR (300 MHz, CDCl$_3$) delta 7.60-7.50 (6H, m), 7.30-7.13 (10H, m), 6.54-6.40 (3H, m), 4.24 (1H, dd, J=9.2, 5.3 Hz), 4.01 (1H, dd, J=9.2, 6.6 Hz), 3.82 (3H, s), 3.80-3.70 (1H, m), 3.23 (3H, s), 2.88 (1H, d, J=10.5 Hz).

MS (ESI) m/z: fragment signal of 243 (positive ion) was observed.

Step 2: (R)-methyl 2-((tert-butoxycarbonyl)amino)-3-(3-methoxyphenoxy)propanoate The title compound was prepared in 93% yield (530 mg, pale brown oil) from (R)-methyl 3-(3-methoxyphenoxy)-2-(tritylamino)propanoate (820 mg, 1.8 mmol) in a similar manner to Step 2 of Intermediate 1.

$^1$H NMR (300 MHz, CDCl$_3$) delta 7.17 (1H, t, J=8.2 Hz), 6.55-6.44 (3H, m), 5.49 (1H, d, J=7.9 Hz), 4.68-4.62 (1H, m), 4.38 (1H, dd, J=9.6, 2.3 Hz), 4.18 (1H, dd, J=9.2, 2.6 Hz), 3.78 (3H, s), 3.77 (3H, s), 1.46 (9H, s).

MS (ESI) m/z: 326 (M+H)$^+$.

Step 3: (R)-2-((tert-butoxycarbonyl)amino)-3-(3-methoxyphenoxy)propanoic acid The title compound was prepared in 43% yield (220 mg, colorless gum) from (R)-methyl 2-((tert-butoxycarbonyl)amino)-3-(3-methoxyphenoxy)propanoate (530 mg, 1.6 mmol) in a similar manner to Step 3 of Intermediate 1.

MS (ESI) m/z: 312 (M+H)$^+$, 310 (M−H)$^−$.

Intermediate 12: (R)-2-((tert-butoxycarbonyl)amino)-3-(2-fluorophenoxy)propanoic acid

Step 1: (R)-methyl 3-(2-fluorophenoxy)-2-(tritylamino)propanoate

The title compound was prepared in 71% yield (890 mg, colorless gum) from (R)-methyl 3-hydroxy-2-(tritylamino)propanoate (1000 mg, 2.8 mmol) and 2-fluorophenol (400 mg, 3.6 mmol) in a similar manner to Step 1 of Intermediate 1.

$^1$H NMR (300 MHz, CDCl$_3$) delta 7.52 (6H, d, J=7.2 Hz), 7.28-7.15 (9H, m), 6397-6.87 (4H, m), 4.32 (1H, dd, J=9.2, 5.3 Hz), 4.06 (1H, dd, J=9.9, 6.6 Hz), 3.78 (1H, br s), 3.23 (3H, s), 2.89 (1H, br s).

MS (ESI) m/z: fragment signal of 243 (positive ion) was observed.

Step 2: (R)-methyl 2-((tert-butoxycarbonyl)amino)-3-(2-fluorophenoxy)propanoate The title compound was prepared in 89% yield (550 mg, colorless oil) from (R)-methyl 3-(2-fluorophenoxy)-2-(tritylamino)propanoate (890 mg, 2.0 mmol) in a similar manner to Step 2 of Intermediate 1.

$^1$H NMR (300 MHz, CDCl$_3$) delta 7.10-7.02 (2H, m), 6.98-6.90 (2H, m), 5.54 (1H, d, J=7.9 Hz), 4.71-4.61 (1H, m), 4.46 (1H, dd, J=9.2, 2.6 Hz), 4.27 (1H, dd, J=9.6, 3.0 Hz), 3.78 (3H, s), 1.46 (9H, s).

MS (ESI) m/z: 314 (M+H)$^+$.

Step 3: (R)-2-((tert-butoxycarbonyl)amino)-3-(2-fluorophenoxy)propanoic acid The title compound was prepared in 50% yield (260 mg, colorless syrup) from (R)-methyl 2-((tert-butoxycarbonyl)amino)-3-(2-fluorophenoxy)propanoate (550 mg, 1.7 mmol) in a similar manner to Step 3 of Intermediate 1.

MS (ESI) m/z: 300 (M+H)$^+$, 298 (M−H)$^−$.

Intermediate 13

(R)-2-(2-((tert-butoxycarbonyl)amino)-2-methylpropanamido)-3-(4-cyanophenoxy)propanoic acid

Step 1: (R)-methyl 3-(4-cyanophenoxy)-2-(tritylamino)propanoate

The title compound was prepared in 49% yield (630 mg, white solid) from (R)-methyl 3-hydroxy-2-(tritylamino)propanoate (1000 mg, 2.8 mmol) and 4-hydroxybenzonitrile (660 mg, 5.5 mmol) in a similar manner to Step 1 of Intermediate 1.

$^1$H NMR (300 MHz, CDCl$_3$) delta 7.58 (2H, d, J=8.6 Hz), 7.56-7.48 (6H, m), 7.30-7.15 (9H, m), 6.91 (2H, d, J=8.6 Hz), 4.25 (1H, dd, J=9.2, 4.6 Hz), 4.03 (1H, dd, J=9.2, 5.9 Hz), 3.74 (1H, m), 3.25 (3H, s), 2.90 (1H, d, J=9.9 Hz).

MS (ESI) m/z: fragment signal of 243 (positive ion) was observed.

Step 2: (R)-methyl 2-(2-((tert-butoxycarbonyl)amino)-2-methylpropanamido)-3-(4-cyanophenoxy)propanoate To a stirred solution of (R)-methyl 3-(4-cyanophenoxy)-2-(tritylamino)propanoate (630 mg, 1.4 mmol) in DCM (8 mL) was slowly added trifluoroacetic acid (3 mL) at room temperature, and the mixture was stirred for 2 hrs at the same temperature. To the mixture was added MeOH (1 mL). The resulting mixture was stirred for 5 min, and then concentrated in vacuo. The residue was dissolved in DCM (5 mL), and then 2-((tert-butoxycarbonyl)amino)-2-methylpropanoic acid (280 mg, 1.4 mmol), 1-ethyl-3-(3-dimethylaminopropyl)carbodiimide hydrochloride (WSC, 390 mg, 2.0 mmol), 1H-benzo[d][1,2,3]triazol-1-ol (HOBt, 210 mg, 1.4 mmol), and triethylamine (0.94 mL, 6.8 mmol) were added to the solution successively at room temperature. After stirring overnight, a saturated aqueous NaHCO$_3$ solution was added to the mixture, and the mixture was extracted with DCM (30 mL×2). The extract was dried over Na$_2$SO$_4$. After filtration, the filtrate was concentrated in vacuo. The residue was purified by column chromatography (silica gel, eluted with 25% to 50% EtOAc in hexane) to give the title compound as a white solid (220 mg, 40% yield).

$^1$H NMR (300 MHz, CDCl$_3$) delta 7.57 (2H, d, J=8.6 Hz), 7.33 (1H, m), 6.93 (2H, d, J=8.6 Hz), 4.97 (1H, m), 4.84 (1H, m), 4.43 (1H, dd, J=9.2, 3.3 Hz), 4.29 (1H, dd, J=9.2, 2.6 Hz), 3.78 (3H, s), 1.49 (3H, s), 1.47 (3H, s), 1.33 (9H, s).

MS (ESI) m/z: 406 (M+H)$^+$, 404 (M−H)$^−$.

Step 3

(R)-2-(2-((tert-butoxycarbonyl)amino)-2-methylpropanamido)-3-(4-cyanophenoxy)propanoic acid The title compound was prepared in 24% yield (51 mg, colorless oil) from (R)-methyl 2-(2-((tert-butoxycarbonyl)amino)-2-methylpropanamido)-3-(4-cyanophenoxy)propanoate (220 mg, 0.54 mmol) in a similar manner to Step 3 of Intermediate 1.

MS (ESI) m/z: 392 (M+H)$^+$.

Intermediate 14

(R)-2-((tert-butoxycarbonyl)amino)-3-(naphthalen-2-yloxy)propanoic acid

Step 1: (R)-methyl 3-(naphthalen-2-yloxy)-2-(tritylamino)propanoate

The title compound was prepared in 32% yield (430 mg, white solid) from (R)-methyl 3-hydroxy-2-(tritylamino)propanoate (1000 mg, 2.8 mmol) and naphthalen-2-ol (520 mg, 3.6 mmol) in a similar manner to Step 1 of Intermediate 1.

$^1$H NMR (300 MHz, CDCl$_3$) delta 7.77-7.70 (3H, m), 7.56-7.40 (7H, m), 7.40-7.10 (12H, m), 4.39 (1H, dd, J=9.2, 4.6 Hz), 4.17-4.08 (1H, m), 3.82-3.77 (1H, m), 3.24 (3H, s), 2.94 (1H, d, J=10.6 Hz)

MS (ESI) m/z: fragment signal of 243 (positive ion) was observed.

Step 2: (R)-methyl 2-((tert-butoxycarbonyl)amino)-3-(naphthalen-2-yloxy)propanoate The title compound was prepared in 95% yield (290 mg, colorless oil) from (R)-methyl 3-(naphthalen-2-yloxy)-2-(tritylamino)propanoate (430 mg, 0.88 mmol) in a similar manner to Step 2 of Intermediate 1.

$^1$H NMR (300 MHz, CDCl$_3$) delta 7.78-7.64 (3H, m), 7.47-7.32 (2H, m), 7.15-7.09 (2H, m), 5.55 (1H, d, J=8.6 Hz), 4.75-4.68 (1H, m), 4.52 (1H, dd, J=9.2, 2.6 Hz), 4.33 (1H, dd, J=9.2, 3.3 Hz), 3.78 (3H, s), 1.47 (9H, s).

MS (ESI) m/z: 246 (M−Boc+H)$^+$.

Step 3: (R)-2-((tert-butoxycarbonyl)amino)-3-(naphthalen-2-yloxy)propanoic acid

The title compound was prepared in 46% yield (130 mg, colorless syrup) from (R)-methyl 2-((tert-butoxycarbonyl)amino)-3-(naphthalen-2-yloxy)propanoate (290 mg, 0.84 mmol) in a similar manner to Step 3 of Intermediate 1.

MS (ESI) m/z: 332 (M+H)$^+$, 330 (M−H)$^−$.

Intermediate 15

(R)-2-((tert-butoxycarbonyl)amino)-3-(naphthalen-1-yloxy)propanoic acid

Step 1: (R)-methyl 3-(naphthalen-1-yloxy)-2-(tritylamino)propanoate

The title compound was prepared in 46% yield (920 mg, white solid) from (R)-methyl 3-hydroxy-2-(tritylamino)propanoate (1500 mg, 4.2 mmol) and naphthalen-1-ol (780 mg, 5.4 mmol) in a similar manner to Step 1 of Intermediate 1.

$^1$H NMR (300 MHz, CDCl$_3$) delta 8.16 (1H, d, J=8.6 Hz), 7.78 (1H, d, J=7.9 Hz), 7.56 (6H, d, J=7.9 Hz), 7.50-7.33 (4H, m), 7.30-7.17 (9H, m), 6.81 (1H, d, J=7.9 Hz), 4.46 (1H, dd, J=8.9, 4.9 Hz), 4.26-4.20 (1H, m), 3.93-3.85 (1H, m), 3.25 (3H, s), 3.01 (1H, d, J=10.5 Hz).

MS (ESI) m/z: fragment signal of 243 (positive ion) was observed.

Step 2: (R)-methyl 2-((tert-butoxycarbonyl)amino)-3-(naphthalen-1-yloxy)propanoate The title compound was prepared in >99% yield (650 mg, colorless oil) from (R)-methyl 3-(naphthalen-1-yloxy)-2-(tritylamino)propanoate (910 mg, 1.9 mmol) in a similar manner to Step 2 of Intermediate 1.

$^1$H NMR (300 MHz, CDCl$_3$) delta 8.15-8.12 (1H, m), 7.81-7.78 (1H, m), 7.52-7.44 (3H, m), 7.36 (1H, t, J=7.9 Hz), 6.78 (1H, d, J=7.9 Hz), 5.63 (1H, d, J=8.6 Hz), 4.87-4.77 (1H, m), 4.52 (1H, dd, J=9.2, 2.7 Hz), 4.42 (1H, dd, J=8.9, 2.3 Hz), 3.79 (3H, s), 1.46 (9H, s).

MS (ESI) m/z: 246 (M−Boc+H)$^+$.

Step 3: (R)-2-((tert-butoxycarbonyl)amino)-3-(naphthalen-1-yloxy)propanoic acid

The title compound was prepared in 69% yield (420 mg, colorless syrup) from (R)-methyl 2-((tert-butoxycarbonyl)amino)-3-(naphthalen-1-yloxy)propanoate (640 mg, 1.9 mmol) in a similar manner to Step 3 of Intermediate 1.

MS (ESI) m/z: 332 (M+H)$^+$, 330 (M−H)$^−$.

Intermediate 16

(R)-2-((tert-butoxycarbonyl)amino)-3-((5-chloropyridin-3-yl)oxy)propanoic acid

Step 1: (R)-methyl 3-((5-chloropyridin-3-yl)oxy)-2-(tritylamino)propanoate

The title compound was prepared in 37% yield (720 mg, white solid) from (R)-methyl 3-hydroxy-2-(tritylamino)propanoate (1500 mg, 4.2 mmol) and 5-chloropyridin-3-ol (700 mg, 5.4 mmol) in a similar manner to Step 1 of Intermediate 1.

$^1$H NMR (300 MHz, CDCl$_3$) delta 8.20 (1H, d, J=1.3 Hz), 8.16 (1H, d, J=2.0 Hz), 7.53-7.45 (6H, m), 7.34-7.15 (10H, m), 4.25 (1H, dd, J=9.2, 4.6 Hz), 4.02 (1H, dd, J=9.2, 6.6 Hz), 3.77-3.69 (1H, m), 3.27 (3H, s), 2.95 (1H, d, J=9.9 Hz).

MS (ESI) m/z: fragment signal of 243 (positive ion) was observed.

Step 2: (R)-2-((tert-butoxycarbonyl)amino)-3-((5-chloropyridin-3-yl)oxy)propanoic acid To a solution of (R)-methyl 3-((5-chloropyridin-3-yl)oxy)-2-(tritylamino)propanoate (600 mg, 1.3 mmol) in dioxane (10 mL) was added 6N hydrochloric acid (3 mL) at room temperature. The mixture was stirred at reflux temperature for 4 hrs. After cooled to room temperature, the mixture was concentrated in vacuo to give a white solid. The white solid was suspended in dioxane (5 mL), and a saturated aqueous NaHCO$_3$ solution (1 mL) and di-tert-butyl dicarbonate (550 mg, 2.5 mmol) were added to the mixture successively. The mixture was stirred for 5 hrs at room temperature, and diluted with water (40 mL). The mixture was washed with DCM (10 mL×2), and water layer was acidified by the addition of 2N hydrochloric acid (~pH5). The water layer was extracted with EtOAc (40 mL×2), and the extract was dried over Na$_2$SO$_4$. After filtration, the filtrate was concentrated in vacuo to give the title compound as a colorless gum (390 mg, 97% yield).

$^1$H NMR (300 MHz, CDCl$_3$) delta 8.24 (1H, s), 8.18 (1H, s), 7.32-7.27 (1H, m), 5.59 (1H, d, J=7.2 Hz), 4.75-4.66 (1H, m), 4.53-4.45 (1H, m), 4.40-4.33 (1H, m), 1.47 (9H, s). COOH was not observed.

MS (ESI) m/z: 317 (M+H)$^+$, 315 (M−H)$^-$.

Intermediate 17: (R)-2-((tert-butoxycarbonyl)amino)-3-(3-cyanophenoxy)propanoic acid

Step 1: (R)-methyl 3-(3-cyanophenoxy)-2-(tritylamino)propanoate

The title compound was prepared in 23% yield (580 mg, colorless solid) from (R)-methyl 3-hydroxy-2-(tritylamino) propanoate (2000 mg, 5.5 mmol) and 3-hydroxybenzonitrile (1000 mg, 8.3 mmol) in a similar manner to Step 1 of Intermediate 1.

$^1$H NMR (300 MHz, CDCl$_3$) delta 7.52 (6H, d, J=7.3 Hz), 7.50-7.16 (11H, m), 7.11-7.08 (2H, m), 4.26-4.21 (1H, m), 4.03-3.97 (1H, m), 3.77-3.69 (1H, m), 3.25 (3H, s), 2.90 (1H, d, J=9.9 Hz).

MS (ESI) m/z: fragment signal of 243 (positive ion) was observed.

Step 2: (R)-methyl 2-((tert-butoxycarbonyl)amino)-3-(3-cyanophenoxy)propanoate The title compound was prepared in 93% yield (370 mg, pale yellow oil) from (R)-methyl 3-(3-cyanophenoxy)-2-(tritylamino)propanoate (570 mg, 1.2 mmol) in a similar manner to Step 2 of Intermediate 1.

$^1$H NMR (300 MHz, CDCl$_3$) delta 7.41-7.36 (1H, m), 7.28 (1H, d, J=6.6 Hz), 7.14-7.10 (2H, m), 5.48 (1H, d, J=7.9 Hz), 4.69 (1H, d, J=7.9 Hz), 4.41 (1H, dd, J=9.2, 2.6 Hz), 4.25 (1H, dd, J=9.2, 3.3 Hz), 3.79 (3H, s), 1.46, 1.49 (9H, s).

MS (ESI) m/z: 221 (M−Boc+H)$^+$.

Step 3: (R)-2-((tert-butoxycarbonyl)amino)-3-(3-cyanophenoxy)propanoic acid

The title compound was prepared in 45% yield (150 mg, colorless gum) from (R)-methyl 2-((tert-butoxycarbonyl) amino)-3-(3-cyanophenoxy)propanoate (360 mg, 1.1 mmol) in a similar manner to Step 3 of Intermediate 1.

MS (ESI) m/z: 307 (M+H)$^+$.

Intermediate 18: (R)-2-((tert-butoxycarbonyl)amino)-3-(pyridin-2-yloxy)propanoic acid

Step 1: (R)-methyl 3-(pyridin-2-yloxy)-2-(tritylamino)propanoate

The title compound was prepared in 15% yield (887 mg, colorless gum) from (R)-methyl 3-hydroxy-2-(tritylamino) propanoate (5000 mg, 14 mmol) and pyridin-2-ol (2000 mg, 21 mmol) in a similar manner to Step 1 of Intermediate 1 by using (E)-diazene-1,2-diylbis(piperidin-1-ylmethanone) (ADDP, 7000 mg, 28 mmol) and tributylphosphine (5600 mg, 28 mmol) instead of bis(2-methoxyethyl) azodicarboxylate and triphenylphosphine, respectively.

MS (ESI) m/z: fragment signal of 243 (positive ion) was observed.

Step 2: (R)-2-((tert-butoxycarbonyl)amino)-3-(pyridin-2-yloxy)propanoic acid The title compound was prepared in 38% yield (210 mg, colorless gum) from (R)-methyl 3-(pyridin-2-yloxy)-2-(tritylamino)propanoate (860 mg, 2.0 mmol) in a similar manner to Step 2 of Intermediate 16.

MS (ESI) m/z: 283 (M+H)$^+$, 281 (M−H)$^-$.

Intermediate 19

(R)-2-((tert-butoxycarbonyl)amino)-3-((5-fluoropyridin-3-yl)oxy)propanoic acid

Step 1: (R)-methyl 3-((5-fluoropyridin-3-yl)oxy)-2-(tritylamino)propanoate

The title compound was prepared in 40% yield (760 mg, white solid) from (R)-methyl 3-hydroxy-2-(tritylamino)propanoate (1500 mg, 4.2 mmol) and 5-fluoropyridin-3-ol (560 mg, 5.0 mmol) in a similar manner to Step 1 of Intermediate 1.

MS (ESI) m/z: fragment signal of 243 (positive ion) was observed.

Step 2: (R)-2-((tert-butoxycarbonyl)amino)-3-((5-fluoropyridin-3-yl)oxy)propanoic acid The title compound was prepared in 46% yield (230 mg, colorless gum) from (R)-methyl 3-((5-fluoropyridin-3-yl) oxy)-2-(tritylamino)propanoate (760 mg, 1.7 mmol) in a similar manner to Step 2 of Intermediate 16.

MS (ESI) m/z: 301 (M+H)$^+$, 299 (M−H)$^-$.

Intermediate 20

(R)-2-((tert-butoxycarbonyl)amino)-3-((6-(trifluoromethyl)pyridin-2-yl)oxy)propanoic acid

Step 1: (R)-methyl 3-((6-(trifluoromethyl)pyridin-2-yl)oxy)-2-(tritylamino)propanoate The title compound was prepared in 81% yield (2300 mg, colorless gum) from (R)-methyl 3-hydroxy-2-(tritylamino)propanoate (2000 mg, 5.5 mmol) and 6-(trifluoromethyl)pyridin-2-ol (900 mg, 5.5 mmol) in a similar manner to Step 1 of Intermediate 1.

$^1$H NMR (300 MHz, CDCl$_3$) delta 7.68 (1H, t, J=7.9 Hz), 7.51 (6H, d, J=7.9 Hz), 7.28-7.14 (10H, m), 6.88 (1H, d, J=8.6 Hz), 4.78 (1H, dd, J=10.9, 4.9 Hz), 4.47 (1H, dd, J=10.9, 6.9 Hz), 3.77 (1H, quint, J=5.6 Hz), 3.16 (3H, s), 2.86 (1H, d, J=10.5 Hz).

MS (ESI) m/z: fragment signal of 243 (positive ion) was observed.

Step 2

(R)-2-((tert-butoxycarbonyl)amino)-3-((6-(trifluoromethyl)pyridin-2-yl)oxy)propanoic acid The title compound was prepared in 70% yield (580 mg, colorless solid) from (R)-methyl 3-((6-(trifluoromethyl)pyridin-2-yl)oxy)-2-(tritylamino)propanoate (1200 mg, 2.4 mmol) in a similar manner to Step 2 of Intermediate 16.

MS (ESI) m/z: 251 (M−Boc+H)$^+$, 349 (M−H)$^-$.

Intermediate 21: (R)-2-((tert-butoxycarbonyl)amino)-3-(4-fluorophenoxy)propanoic acid

Step 1: (R)-methyl 3-(4-fluorophenoxy)-2-(tritylamino)propanoate

The title compound was prepared in 15% yield (95 mg, colorless gum) from (R)-methyl 3-hydroxy-2-(tritylamino)propanoate (0.50 g, 1.4 mmol) and 4-fluorophenol (0.20 g, 1.8 mmol) in a similar manner to Step 1 of Intermediate 1.

MS (ESI) m/z: 478 (M+Na)$^+$, and fragment signal of 243 (positive ion) was observed.

Step 2: (R)-2-((tert-butoxycarbonyl)amino)-3-(4-fluorophenoxy)propanoic acid The title compound was prepared in 72% yield (45 mg, colorless oil) from (R)-methyl 3-(4-fluorophenoxy)-2-(tritylamino)propanoate (95 mg, 0.21 mmol) in a similar manner to Step 2 of Intermediate 16.

$^1$H NMR (270 MHz, CDCl$_3$): delta 7.00-6.93 (2H, m), 6.86-6.80 (2H, m), 5.49 (1H, d, J=7.9 Hz), 4.68 (1H, d, J=8.6 Hz), 4.40 (1H, dd, J=9.2, 2.6 Hz), 4.19 (1H, dd, J=9.2, 3.3 Hz).

MS (ESI) m/z: 300 (M+H)$^+$, 298 (M−H)$^-$.

TABLE 4

| Intermediate | Name | Structure |
|---|---|---|
| 1 | (R)-2-((tert-butoxycarbonyl)amino)-3-(2,4-difluorophenoxy)propanoic acid | 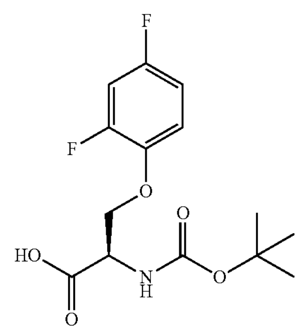 [SMILES: CC(C)(C)OC(=O)N[C@H](COc1ccc(F)cc1F)C(=O)O] |
| 2 | (R)-2-((tert-butoxycarbonyl)amino)-3-phenoxypropanoic acid | 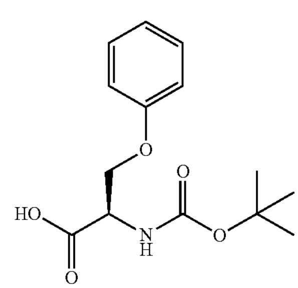 [SMILES: CC(C)(C)OC(=O)N[C@H](COc1ccccc1)C(=O)O] |

TABLE 4-continued

| Intermediate | Name | Structure |
|---|---|---|
| 3 | (R)-2-((tert-butoxycarbonyl)amino)-3-(4-chlorophenoxy)propanoic acid | 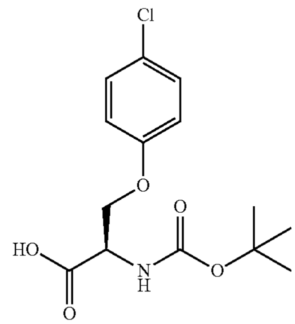 [SMILES: CC(C)(C)OC(=O)N[C@H](COc1ccc(Cl)cc1)C(=O)O] |
| 4 | (R)-2-((tert-butoxycarbonyl)amino)-3-(3-chlorophenoxy)propanoic acid | 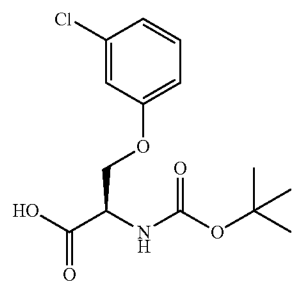 [SMILES: CC(C)(C)OC(=O)N[C@H](COc1cccc(Cl)c1)C(=O)O] |
| 5 | (R)-methyl-3-(3,5-dichlorophenoxy)-2-(tritylamino)propanoate | 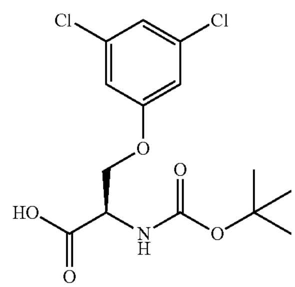 [SMILES: CC(C)(C)OC(=O)N[C@H](COc1cc(Cl)cc(Cl)c1)C(=O)O] |
| 6 | (R)-2-((tert-butoxycarbonyl)amino)-3-(2-(trifluoromethyl)phenoxy)propanoic acid | 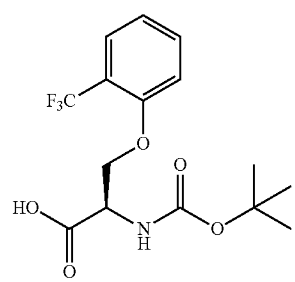 [SMILES: CC(C)(C)OC(=O)N[C@H](COc1ccccc1C(F)(F)F)C(=O)O] |
| 7 | (R)-2-((tert-butoxycarbonyl)amino)-3-(3,4-difluorophenoxy)propanoic acid | 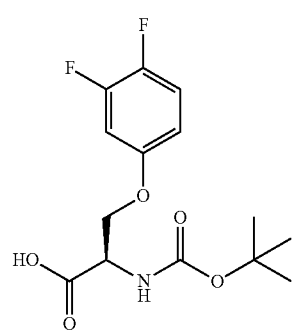 [SMILES: CC(C)(C)OC(=O)N[C@H](COc1ccc(F)c(F)c1)C(=O)O] |

TABLE 4-continued

| Intermediate | Name | Structure |
|---|---|---|
| 8 | (R)-2-((tert-butoxycarbonyl)amino)-3-(2-chlorophenoxy)propanoic acid | 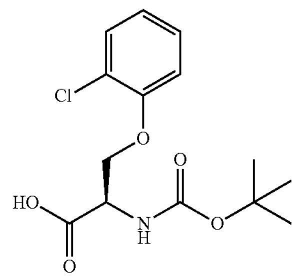 [SMILES: CC(C)(C)OC(=O)N[C@H](COc1ccccc1Cl)C(=O)O] |
| 9 | (R)-3-(3,5-bis(trifluoromethyl)phenoxy)-2-((tert-butoxycarbonyl)amino)propanoic acid | 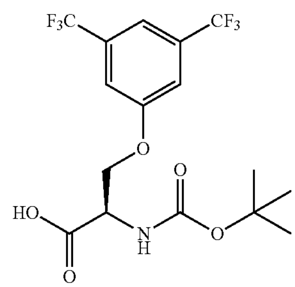 [SMILES: CC(C)(C)OC(=O)N[C@H](COc1cc(C(F)(F)F)cc(C(F)(F)F)c1)C(=O)O] |
| 10 | (R)-2-((tert-butoxycarbonyl)amino)-3-(3-fluorophenoxy)propanoic acid | 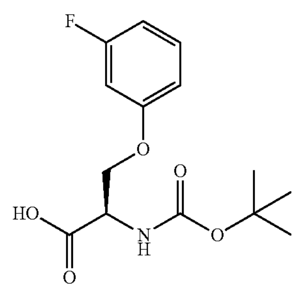 |
| 11 | (R)-2-((tert-butoxycarbonyl)amino)-3-(3-methoxyphenoxy)propanoic acid | 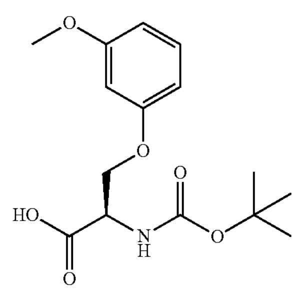 [SMILES: COc1cccc(OC[C@@H](NC(=O)OC(C)(C)C)C(=O)O)c1] |
| 12 | (R)-2-((tert-butoxycarbonyl)amino)-3-(2-fluorophenoxy)propanoic acid | 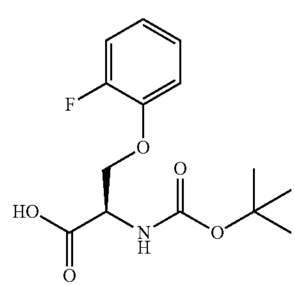 [SMILES: CC(C)(C)OC(=O)N[C@H](COc1ccccc1F)C(=O)O] |

TABLE 4-continued

| Intermediate | Name | Structure |
|---|---|---|
| 13 | (R)-2-(2-((tert-butoxycarbonyl)amino)-2-methylpropanamido)-3-(4-cyanophenoxy)propanoic acid | 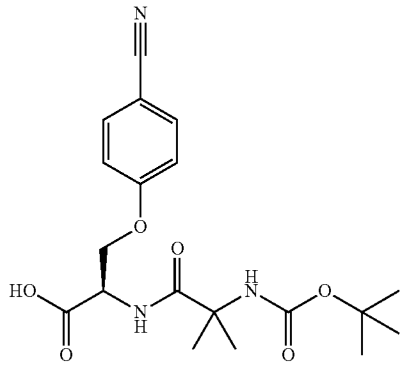 [SMILES: CC(C)(C)OC(=O)NC(C)(C)C(=O)N[C@H](COc1ccc(C#N)cc1)C(=O)O] |
| 14 | (R)-2-((tert-butoxycarbonyl)amino)-3-(naphthalen-2-yloxy)propanoic acid | 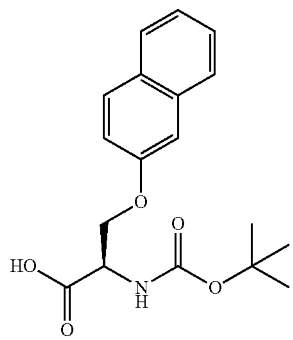 [SMILES: CC(C)(C)OC(=O)N[C@H](COc1ccc2ccccc2c1)C(=O)O] |
| 15 | (R)-2-((tert-butoxycarbonyl)amino)-3-(naphthalen-1-yloxy)propanoic acid | 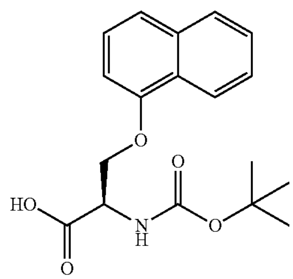 [SMILES: CC(C)(C)OC(=O)N[C@H](COc1cccc2ccccc12)C(=O)O] |
| 16 | (R)-2-((tert-butoxycarbonyl)amino)-3-((5-chloropyridin-3-yl)oxy)propanoic acid | 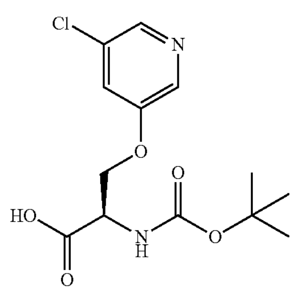 [SMILES: CC(C)(C)OC(=O)N[C@H](COc1cncc(Cl)c1)C(=O)O] |
| 17 | (R)-2-((tert-butoxycarbonyl)amino)-3-(3-cyanophenoxy)propanoic acid | 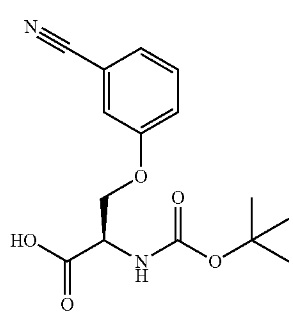 [SMILES: CC(C)(C)OC(=O)N[C@H](COc1cccc(C#N)c1)C(=O)O] |

TABLE 4-continued

| Intermediate | Name | Structure |
|---|---|---|
| 18 | (R)-2-((tert-butoxycarbonyl)amino)-3-(pyridin-2-yloxy)propanoic acid | 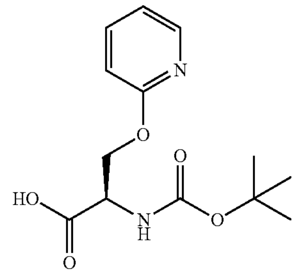 [SMILES: CC(C)(C)OC(=O)N[C@H](COc1ccccn1)C(=O)O] |
| 19 | (R)-2-((tert-butoxycarbonyl)amino)-3-((5-fluoropyridin-3-yl)oxy)propanoic acid | 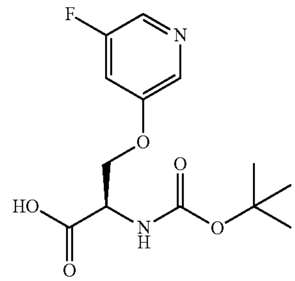 |
| 20 | (R)-2-((tert-butoxycarbonyl)amino)-3-((6-(trifluoromethyl)pyridin-2-yl)oxy)propanoic acid | 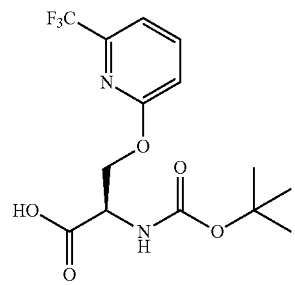 [SMILES: CC(C)(C)OC(=O)N[C@H](COc1cccc(C(F)(F)F)n1)C(=O)O] |
| 21 | (R)-2-((tert-butoxycarbonyl)amino)-3-(4-fluorophenoxy)propanoic acid | 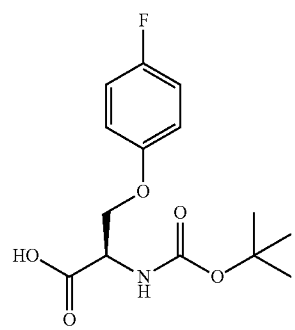 [SMILES: CC(C)(C)OC(=O)N[C@H](COc1ccc(F)cc1)C(=O)O] |

Example 1

2-amino-N—((R)-1-((R)-3a-benzyl-2-methyl-3-oxo-3a,4,6,7-tetrahydro-2H-pyrazolo[4,3-c]pyridin-5(3H)-yl)-3-(2,4-difluorophenoxy)-1-oxopropan-2-yl)-2-methylpropanamide

Step 1: tert-butyl ((R)-1-((R)-3a-benzyl-2-methyl-3-oxo-3a,4,6,7-tetrahydro-2H-pyrazolo[4,3-c]pyridin-5(3H)-yl)-3-(2,4-difluorophenoxy)-1-oxopropan-2-yl)carbamate A suspension of (R)-3a-benzyl-2-methyl-4,5,6,7-tetrahydro-2H-pyrazolo[4,3-c]pyridin-3(3aH)-one (2R,3R)-2,3-dihydroxysuccinate (100 mg, 0.25 mmol) in EtOAc (3 mL) was cooled to −5° C. under nitrogen atmosphere, and triethylamine (0.18 mL, 1.3 mmol) was added dropwise to the suspension at the same temperature. After stirring for 20 min, a solution of (R)-2-((tert-butoxycarbonyl)amino)-3-(2,4-difluorophenoxy)propanoic acid (113 mg, 0.36 mmol, Step 3 of Intermediate 1) in EtOAc (2 mL), and 2,4,6-tripropyl-1,3,5,2,4,6-trioxatriphosphinane 2,4,6-trioxide (0.30 mL, 0.51 mmol; 1.7 M solution in EtOAc) were added to the mixture successively at the same temperature. After stirring for 1 hr at −5° C., the mixture was quenched by the addition of a saturated aqueous NaHCO$_3$ solution (5 mL). The mixture was diluted with water and extracted with EtOAc (20 mL×3). The combined organic layers were washed with brine, and was dried over Na$_2$SO$_4$. After filtration, the filtrate was concentrated in vacuo. The residue was purified by column chromatography (silica gel, eluted with 50% EtOAc in hexane) to give the title compound as a colorless solid (72 mg, 52% yield).

MS (ESI) m/z: 543 (M+H)+

Step 2

(R)-5-((R)-2-amino-3-(2,4-difluorophenoxy)propanoyl)-3a-benzyl-2-methyl-4,5,6,7-tetrahydro-2H-pyrazolo[4,3-c]pyridin-3(3aH)-one To a stirred solution of tert-butyl ((R)-1-((R)-3a-benzyl-2-methyl-3-oxo-3a,4,6,7-tetrahydro-2H-pyrazolo[4,3-c]pyridin-5(3H)-yl)-3-(2,4-difluorophenoxy)-1-oxopropan-2-yl)carbamate (70 mg, 0.13 mmol) in DCM (1 mL) was added trifluoroacetic acid (1 mL) in one portion at 0° C., and stirring was continued for 1 hr at the same temperature. The mixture was concentrated in vacuo, and the residue was diluted with DCM (5 mL). The extracted solution was washed with a saturated aqueous NaHCO$_3$ solution and then brine, and was dried over Na$_2$SO$_4$. After filtration, the filtrate was concentrated in vacuo to give the title compound as a colorless gum (66 mg, >99% yield).

MS (ESI) m/z: 443 (M+H)+

Step 3: tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(2,4-difluorophenoxy)-1-oxopropan-2-yl)amino)-2-methyl-1-oxopropan-2-yl)carbamate To a solution of (R)-5-((R)-2-amino-3-(2,4-difluorophenoxy)propanoyl)-3a-benzyl-2-methyl-4,5,6,7-tetrahydro-2H-pyrazolo[4,3-c]pyridin-3(3aH)-one (66 mg, 0.15 mmol), 2-((tert-butoxycarbonyl)amino)-2-methylpropanoic acid (38 mg, 0.19 mmol), and triethylamine (0.083 mL, 0.60 mmol) in DCM (1 mL) was added O-(benzotriazol-1-yl)-N,N,N',N'-tetramethyluronium hexafluorophosphate (HBTU, 68 mg, 0.18 mmol) at room temperature. After stirring for 1 hr, the mixture was concentrated in vacuo. The residue was passed through a short column chromatography (amino-gel, eluted with EtOAc) to give the title compound as a colorless gum (60 mg, 87% yield).

MS (ESI) m/z: 628 (M+H)+, 626 (M−H)

Step 4

2-amino-N—((R)-1-((R)-3a-benzyl-2-methyl-3-oxo-3a,4,6,7-tetrahydro-2H-pyrazolo[4,3-c]pyridin-5(3H)-yl)-3-(2,4-difluorophenoxy)-1-oxopropan-2-yl)-2-methylpropanamide To a stirred solution of tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(2,4-difluorophenoxy)-1-oxopropan-2-yl)amino)-2-methyl-1-oxopropan-2-yl)carbamate (81 mg, 0.13 mmol) in DCM (1 mL) was added trifluoroacetic acid (1 mL) in one portion at 0° C., and stirring was continued for 2 hrs at the same temperature. The mixture was concentrated in vacuo, and the residue was diluted with DCM (5 mL). The solution was washed with a saturated aqueous NaHCO$_3$ solution and then brine, and was dried over Na$_2$SO$_4$. After filtration, the solvent, and volatiles were removed. The residue was purified by preparative LC-MS to give 11 mg (16% yield) of the title compound.

Condition for the preparative LC-MS and quality check (QC) method are shown in Table 5.

Example 2

2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-3-phenoxypropan-2-yl)-2-methylpropanamide

Step 1: tert-butyl ((R)-1-((R)-3a-benzyl-2-methyl-3-oxo-3a,4,6,7-tetrahydro-2H-pyrazolo[4,3-c]pyridin-5(3H)-yl)-1-oxo-3-phenoxypropan-2-yl)carbamate The title compound was prepared in 50% yield (510 mg, white solid) from (R)-3a-benzyl-2-methyl-4,5,6,7-tetrahydro-2H-pyrazolo[4,3-c]pyridin-3(3aH)-one (2R,3R)-2,3-dihydroxysuccinate (800 mg, 2.0 mmol) and (R)-2-((tert-butoxycarbonyl)amino)-3-phenoxypropanoic acid (630 mg, 2.2 mmol, Step 3 of Intermediate 2) in a similar manner to Step 1 of Example 1.

$^1$H NMR (300 MHz, CDCl$_3$) delta 7.31-7.15 (5H, m), 7.10-6.90 (3H, m), 6.87 (2H, d, J=7.9 Hz), 5.52-5.42 (1H, m), 5.23-5.05 (2H, m), 4.61-4.50 (1H, m), 4.26-4.08 (2H, m), 3.23 (1H, d, J=13.2 Hz), 3.09 (3H, s), 3.08-2.90 (2H, m), 2.66-2.50 (2H, m), 1.45 (9H, s). NHBoc was not observed.

MS (ESI) m/z: 507 (M+H)+, 505 (M−H)−.

Step 2

(R)-5-((R)-2-amino-3-phenoxypropanoyl)-3a-benzyl-2-methyl-4,5,6,7-tetrahydro-2H-pyrazolo[4,3-c]pyridin-3(3aH)-one The title compound was prepared in 95% yield (390 mg, white solid) from tert-butyl ((R)-1-((R)-3a-benzyl-2-methyl-3-oxo-3a,4,6,7-tetrahydro-2H-pyrazolo[4,3-c]pyridin-5(3H)-yl)-1-oxo-3-phenoxypropan-2-yl)carbamate (800 mg, 2.0 mmol) in a similar manner to Step 2 of Example 1.

MS (ESI) m/z: 407 (M+H)+.

Step 3: tert-butyl (1-(((R)-1-((R)-3a-benzyl-2-methyl-3-oxo-3a,4,6,7-tetrahydro-2H-pyrazolo[4,3-c]pyridin-5(3H)-yl)-1-oxo-3-phenoxypropan-2-yl)amino)-2-methyl-1-oxopropan-2-yl)carbamate The title compound was prepared in 99% yield (560 mg, white solid) from (R)-5-((R)-2-amino-3-phenoxypropanoyl)-3a-benzyl-2-methyl-4,5,6,7-tetrahydro-2H-pyrazolo[4,3-c]pyridin-3(3aH)-one (390 mg, 0.96 mmol) and 2-((tert-butoxycarbonyl)amino)-2-methylpropanoic acid (230 mg, 1.2 mmol) in a similar manner to Step 3 of Example 1.

$^1$H NMR (300 MHz, CDCl$_3$) delta 7.35-7.12 (5H, m), 7.10-7.04 (2H, m), 7.00-6.84 (3H, m), 5.52-5.42 (1H, m), 5.07 (1H, d, J=12.5 Hz), 4.85 (1H, br s), 4.64-4.52 (1H, m), 4.30-4.22 (1H, m), 4.16-4.10 (1H, m), 3.19 (1H, d, J=13.8 Hz), 3.07 (3H, s), 3.05-2.85 (2H, m), 2.64-2.50 (2H, m), 1.51 (3H, s), 1.49 (3H, s), 1.38 (9H, s). CONH and NHBoc were not observed.

MS (ESI) m/z: 592 (M+H)+, 590 (M−H)−.

Step 4

2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-3-phenoxypropan-2-yl)-2-methylpropanamide The title compound was prepared in 86% yield (395 mg, white solid) from tert-butyl (1-(((R)-1-((R)-3a-benzyl-2-methyl-3-oxo-3a,4,6,7-tetrahydro-2H-pyrazolo[4,3-c]pyridin-5(3H)-yl)-1-oxo-3-phenoxypropan-2-yl)amino)-2-methyl-1-oxopropan-2-yl)carbamate (550 mg, 0.93 mmol) in a similar manner to Step 4 of Example 1. In this case, the title compound was purified by column chromatography (NH-gel, eluted with 0% to 80% EtOAc in hexane).

$^1$H-NMR (300 MHz, CDCl$_3$) delta 8.45 (1H, d, J=7.3 Hz), 7.30-7.15 (5H, m), 7.12-6.85 (5H, m), 5.45-5.35 (1H, m), 5.09 (1H, d, J=12.5 Hz), 4.61 (1H, d, J=10.6 Hz), 4.24 (2H, d, J=6.6 Hz), 3.22 (1H, d, J=13.1 Hz), 3.08 (3H, s), 3.10-2.85 (3H, m), 2.65-2.48 (2H, m), 1.40 (3H, s), 1.35 (3H, s). NH$_2$ was not observed.

MS (ESI) m/z: 492 (M+H)$^+$, 490 (M−H).

A part of the product was further purified by preparative LC-MS to give the title compound.

Example 3

2-amino-N—((R)-1-((R)-3a-benzyl-2-methyl-3-oxo-3a,4,6,7-tetrahydro-2H-pyrazolo[4,3-c]pyridin-5(3H)-yl)-3-(4-chlorophenoxy)-1-oxopropan-2-yl)-2-methylpropanamide

Step 1: tert-butyl ((R)-1-((R)-3a-benzyl-2-methyl-3-oxo-3a,4,6,7-tetrahydro-2H-pyrazolo[4,3-c]pyridin-5(3H)-yl)-3-(4-chlorophenoxy)-1-oxopropan-2-yl)carbamate The title compound was prepared in 53% yield (73 mg, white solid) from (R)-3a-benzyl-2-methyl-4,5,6,7-tetrahydro-2H-pyrazolo[4,3-c]pyridin-3(3aH)-one (2R,3R)-2,3-dihydroxysuccinate (100 mg, 0.25 mmol) and (R)-2-((tert-butoxycarbonyl)amino)-3-(4-chlorophenoxy)propanoic acid (110 mg, 0.36 mmol, Step 3 of Intermediate 3) in a similar manner to Step 1 of Example 1.

MS (ESI) m/z: 541 (M+H)$^+$.

Step 2

(R)-5-((R)-2-amino-3-(4-chlorophenoxy)propanoyl)-3a-benzyl-2-methyl-4,5,6,7-tetrahydro-2H-pyrazolo[4,3-c]pyridin-3(3aH)-one The title compound was prepared in >99% yield (61 mg, colorless gum) from tert-butyl ((R)-1-((R)-3a-benzyl-2-methyl-3-oxo-3a,4,6,7-tetrahydro-2H-pyrazolo[4,3-c]pyridin-5(3H)-yl)-3-(4-chlorophenoxy)-1-oxopropan-2-yl)carbamate (70 mg, 0.13 mmol) in a similar manner to Step 2 of Example 1.

MS (ESI) m/z: 441 (M+H)$^+$.

Step 3: tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(4-chlorophenoxy)-1-oxopropan-2-yl)amino)-2-methyl-1-oxopropan-2-yl)carbamate The title compound was prepared in 94% yield (81 mg, colorless gum) from (R)-5-((R)-2-amino-3-(4-chlorophenoxy)propanoyl)-3a-benzyl-2-methyl-4,5,6,7-tetrahydro-2H-pyrazolo[4,3-c]pyridin-3(3aH)-one (61 mg, 0.14 mmol) and 2-((tert-butoxycarbonyl)amino)-2-methylpropanoic acid (35 mg, 0.17 mmol) in a similar manner to Step 3 of Example 1.

$^1$H-NMR (300 MHz, CDCl$_3$) delta 7.31-7.18 (5H, m), 7.09-7.08 (2H, m), 6.82 (2H, d, J=8.8 Hz), 5.46 (1H, q, J=7.1 Hz), 5.08 (1H, d, J=12.5 Hz), 4.86 (1H, s), 4.62-4.51 (1H, m), 4.31-4.20 (1H, m), 4.16-4.03 (1H, m), 3.19 (1H, d, J=13.9 Hz), 3.08-2.86 (7H, m), 2.65-2.53 (2H, m), 1.50 (3H, s), 1.49 (3H, s), 1.37 (9H, s).

MS (ESI) m/z: 626 (M+H)$^+$, 624 (M−H)$^−$.

Step 4

2-amino-N—((R)-1-((R)-3a-benzyl-2-methyl-3-oxo-3a,4,6,7-tetrahydro-2H-pyrazolo[4,3-c]pyridin-5(3H)-yl)-3-(4-chlorophenoxy)-1-oxopropan-2-yl)-2-methylpropanamide The title compound was prepared in 16% yield (11 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(4-chlorophenoxy)-1-oxopropan-2-yl)amino)-2-methyl-1-oxopropan-2-yl)carbamate (81 mg, 0.13 mmol) in a similar manner to Step 4 of Example 1.

Example 4

2-amino-N—((R)-1-((R)-3a-benzyl-2-methyl-3-oxo-3a,4,6,7-tetrahydro-2H-pyrazolo[4,3-c]pyridin-5(3H)-yl)-3-(3-chlorophenoxy)-1-oxopropan-2-yl)-2-methylpropanamide

Step 1: tert-butyl ((R)-1-((R)-3a-benzyl-2-methyl-3-oxo-3a,4,6,7-tetrahydro-2H-pyrazolo[4,3-c]pyridin-5(3H)-yl)-3-(3-chlorophenoxy)-1-oxopropan-2-yl)carbamate The title compound was prepared in 61% yield (105 mg, colorless gum) from (R)-3a-benzyl-2-methyl-4,5,6,7-tetrahydro-2H-pyrazolo[4,3-c]pyridin-3(3aH)-one (2R,3R)-2,3-dihydroxysuccinate (100 mg, 0.25 mmol) and (R)-2-((tert-butoxycarbonyl)amino)-3-(3-chlorophenoxy)propanoic acid (120 mg, 0.38 mmol, Step 3 of Intermediate 4) in a similar manner to Step 1 of Example 1.

MS (ESI) m/z: 541 (M+H)$^+$.

Step 2

(R)-5-((R)-2-amino-3-(3-chlorophenoxy)propanoyl)-3a-benzyl-2-methyl-4,5,6,7-tetrahydro-2H-pyrazolo[4,3-c]pyridin-3(3aH)-one The title compound was prepared in >99% yield (79 mg, colorless solid) from tert-butyl ((R)-1-((R)-3a-benzyl-2-methyl-3-oxo-3a,4,6,7-tetrahydro-2H-pyrazolo[4,3-c]pyridin-5(3H)-yl)-3-(3-chlorophenoxy)-1-oxopropan-2-yl)carbamate (95 mg, 0.18 mmol) in a similar manner to Step 2 of Example 1.

MS (ESI) m/z: 441 (M+H)$^+$.

Step 3: tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(3-chlorophenoxy)-1-oxopropan-2-yl)amino)-2-methyl-1-oxopropan-2-yl)carbamate The title compound was prepared in >99% yield (100 mg, colorless gum) from (R)-5-((R)-2-amino-3-(3-chlorophenoxy)propanoyl)-3a-benzyl-2-methyl-4,5,6,7-tetrahydro-2H-pyrazolo[4,3-c]pyridin-3(3aH)-one (68 mg, 0.15 mmol) and 2-((tert-butoxycarbonyl)amino)-2-methylpropanoic acid (39 mg, 0.19 mmol) in a similar manner to Step 3 of Example 1.
MS (ESI) m/z: 626 (M+H)⁺, 624 (M−H)⁻.

Step 4

2-amino-N—((R)-1-((R)-3a-benzyl-2-methyl-3-oxo-3a,4,6,7-tetrahydro-2H-pyrazolo[4,3-c]pyridin-5(3H)-yl)-3-(3-chlorophenoxy)-1-oxopropan-2-yl)-2-methylpropanamide The title compound was prepared in 14% yield (11 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(3-chlorophenoxy)-1-oxopropan-2-yl)amino)-2-methyl-1-oxopropan-2-yl)carbamate (92 mg, 0.15 mmol) in a similar manner to Step 4 of Example 1.

Example 5

2-amino-N—((R)-1-((R)-3a-benzyl-2-methyl-3-oxo-3a,4,6,7-tetrahydro-2H-pyrazolo[4,3-c]pyridin-5(3H)-yl)-3-(3,5-dichlorophenoxy)-1-oxopropan-2-yl)-2-methylpropanamide Step 1: tert-butyl ((R)-1-((R)-3a-benzyl-2-methyl-3-oxo-3a,4,6,7-tetrahydro-2H-pyrazolo[4,3-c]pyridin-5(3H)-yl)-3-(3,5-dichlorophenoxy)-1-oxopropan-2-yl)carbamate The title compound was prepared in 47% yield (86 mg, colorless gum) from (R)-3a-benzyl-2-methyl-4,5,6,7-tetrahydro-2H-pyrazolo[4,3-c]pyridin-3(3aH)-one (2R,3R)-2,3-dihydroxysuccinate (130 mg, 0.32 mmol) and (R)-2-((tert-butoxycarbonyl)amino)-3-(3,5-dichlorophenoxy)propanoic acid (130 mg, 0.38 mmol, Step 3 of Intermediate 5) in a similar manner to Step 1 of Example 1.
MS (ESI) m/z: 575 (M+H)⁺.

Step 2

(R)-5-((R)-2-amino-3-(3,5-dichlorophenoxy)propanoyl)-3a-benzyl-2-methyl-4,5,6,7-tetrahydro-2H-pyrazolo[4,3-c]pyridin-3(3aH)-one The title compound was prepared in >99% yield (70 mg, colorless gum) from tert-butyl ((R)-1-((R)-3a-benzyl-2-methyl-3-oxo-3a,4,6,7-tetrahydro-2H-pyrazolo[4,3-c]pyridin-5(3H)-yl)-3-(3,5-dichlorophenoxy)-1-oxopropan-2-yl)carbamate (76 mg, 0.13 mmol) in a similar manner to Step 2 of Example 1.
MS (ESI) m/z: 475 (M+H)⁺.

Step 3: tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(3,5-dichlorophenoxy)-1-oxopropan-2-yl)amino)-2-methyl-1-oxopropan-2-yl)carbamate The title compound was prepared in >99% yield (89 mg, colorless gum) from (R)-5-((R)-2-amino-3-(3,5-dichlorophenoxy)propanoyl)-3a-benzyl-2-methyl-4,5,6,7-tetrahydro-2H-pyrazolo[4,3-c]pyridin-3(3aH)-one (61 mg, 0.13 mmol) and 2-((tert-butoxycarbonyl)amino)-2-methylpropanoic acid (33 mg, 0.16 mmol) in a similar manner to Step 3 of Example 1.
MS (ESI) m/z: 660 (M+H)⁺, 658 (M−H)⁻.

Step 4

2-amino-N—((R)-1-((R)-3a-benzyl-2-methyl-3-oxo-3a,4,6,7-tetrahydro-2H-pyrazolo[4,3-c]pyridin-5(3H)-yl)-3-(3,5-dichlorophenoxy)-1-oxopropan-2-yl)-2-methylpropanamide The title compound was prepared in 18% yield (12 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(3,5-dichlorophenoxy)-1-oxopropan-2-yl)amino)-2-methyl-1-oxopropan-2-yl)carbamate (81 mg, 0.12 mmol) in a similar manner to Step 4 of Example 1.

Example 6

2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-3-(2-(trifluoromethyl)phenoxy)propan-2-yl)-2-methylpropanamide Step 1: tert-butyl ((R)-1-((R)-3a-benzyl-2-methyl-3-oxo-3a,4,6,7-tetrahydro-2H-pyrazolo[4,3-c]pyridin-5(3H)-yl)-1-oxo-3-(2-(trifluoromethyl)phenoxy)propan-2-yl)carbamate The title compound was prepared in 66% yield (77 mg, colorless gum) from (R)-3a-benzyl-2-methyl-4,5,6,7-tetrahydro-2H-pyrazolo[4,3-c]pyridin-3(3aH)-one (2R,3R)-2,3-dihydroxysuccinate (130 mg, 0.32 mmol) and (R)-2-((tert-butoxycarbonyl)amino)-3-(2-(trifluoromethyl)phenoxy)propanoic acid (85 mg, 0.24 mmol, Step 3 of Intermediate 6) in a similar manner to Step 1 of Example 1.
MS (ESI) m/z: 575 (M+H)⁺, 573 (M−H)⁻.

Step 2

(R)-5-((R)-2-amino-3-(2-(trifluoromethyl)phenoxy)propanoyl)-3a-benzyl-2-methyl-4,5,6,7-tetrahydro-2H-pyrazolo[4,3-c]pyridin-3(3aH)-one The title compound was prepared in 86% yield (45 mg) from tert-butyl ((R)-1-((R)-3a-benzyl-2-methyl-3-oxo-3a,4,6,7-tetrahydro-2H-pyrazolo[4,3-c]pyridin-5(3H)-yl)-1-oxo-3-(2-(trifluoromethyl)phenoxy)propan-2-yl)carbamate (64 mg, 0.11 mmol) in a similar manner to Step 2 of Example 1.

Step 3: tert-butyl (1-(((R)-1-((R)-3a-benzyl-2-methyl-3-oxo-3a,4,6,7-tetrahydro-2H-pyrazolo[4,3-c]pyridin-5(3H)-yl)-1-oxo-3-(2-(trifluoromethyl)phenoxy)propan-2-yl)amino)-2-methyl-1-oxopropan-2-yl)carbamate The title compound was prepared in >99% yield (79 mg, colorless gum) from (R)-5-((R)-2-amino-3-(2-(trifluoromethyl)phenoxy)propanoyl)-3a-benzyl-2-methyl-4,5,6,7-tetrahydro-2H-pyrazolo[4,3-c]pyridin-3(3aH)-one (45 mg, 0.095 mmol) and 2-((tert-butoxycarbonyl)amino)-2-methylpropanoic acid (23 mg, 0.11 mmol) in a similar manner to Step 3 of Example 1.
MS (ESI) m/z: 660 (M+H)$^+$, 658 (M−H)$^-$.

Step 4

2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-3-(2-(trifluoromethyl)phenoxy)propan-2-yl)-2-methylpropanamide The title compound was prepared in 22% yield (14 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-1-oxo-3-(2-(trifluoromethyl)phenoxy)propan-2-yl)amino)-2-methyl-1-oxopropan-2-yl)carbamate (75 mg, 0.11 mmol) in a similar manner to Step 4 of Example 1.

Example 7

2-amino-N—((R)-1-((R)-3a-benzyl-2-methyl-3-oxo-3a,4,6,7-tetrahydro-2H-pyrazolo[4,3-c]pyridin-5(3H)-yl)-3-(3,4-difluorophenoxy)-1-oxopropan-2-yl)-2-methylpropanamide Step 1: tert-butyl ((R)-1-((R)-3a-benzyl-2-methyl-3-oxo-3a,4,6,7-tetrahydro-2H-pyrazolo[4,3-c]pyridin-5(3H)-yl)-3-(3,4-difluorophenoxy)-1-oxopropan-2-yl)carbamate The title compound was prepared in 66% yield (73 mg, colorless gum) from (R)-3a-benzyl-2-methyl-4,5,6,7-tetrahydro-2H-pyrazolo[4,3-c]pyridin-3(3aH)-one (2R,3R)-2,3-dihydroxysuccinate (130 mg, 0.32 mmol) and (R)-2-((tert-butoxycarbonyl)amino)-3-(3,4-difluorophenoxy)propanoic acid (77 mg, 0.24 mmol, Step 3 of Intermediate 7) in a similar manner to Step 1 of Example 1.
MS (ESI) m/z: 543 (M+H)$^+$, 541 (M−H)$^-$.

Step 2

(R)-5-((R)-2-amino-3-(3,4-difluorophenoxy)propanoyl)-3a-benzyl-2-methyl-4,5,6,7-tetrahydro-2H-pyrazolo[4,3-c]pyridin-3(3aH)-one The title compound was prepared in 92% yield (54 mg) from tert-butyl ((R)-1-((R)-3a-benzyl-2-methyl-3-oxo-3a,4,6,7-tetrahydro-2H-pyrazolo[4,3-c]pyridin-5(3H)-yl)-3-(3,4-difluorophenoxy)-1-oxopropan-2-yl)carbamate (72 mg, 0.13 mmol) in a similar manner to Step 2 of Example 1.
MS (ESI) m/z: 443 (M+H)$^+$.

Step 3: tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(3,4-difluorophenoxy)-1-oxopropan-2-yl)amino)-2-methyl-1-oxopropan-2-yl)carbamate The title compound was prepared in >99% yield (91 mg, colorless gum) from (R)-5-((R)-2-amino-3-(3,4-difluorophenoxy)propanoyl)-3a-benzyl-2-methyl-4,5,6,7-tetrahydro-2H-pyrazolo[4,3-c]pyridin-3(3aH)-one (54 mg, 0.12 mmol) and 2-((tert-butoxycarbonyl)amino)-2-methylpropanoic acid (23 mg, 0.11 mmol) in a similar manner to Step 3 of Example 1.
MS (ESI) m/z: 628 (M+H)$^+$, 626 (M−H)$^-$.

Step 4

2-amino-N—((R)-1-((R)-3a-benzyl-2-methyl-3-oxo-3a,4,6,7-tetrahydro-2H-pyrazolo[4,3-c]pyridin-5(3H)-yl)-3-(3,4-difluorophenoxy)-1-oxopropan-2-yl)-2-methylpropanamide The title compound was prepared in 15% yield (12 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(3,4-difluorophenoxy)-1-oxopropan-2-yl)amino)-2-methyl-1-oxopropan-2-yl)carbamate (91 mg, 0.15 mmol) in a similar manner to Step 4 of Example 1.

Example 8

2-amino-N—((R)-1-((R)-3a-benzyl-2-methyl-3-oxo-3a,4,6,7-tetrahydro-2H-pyrazolo[4,3-c]pyridin-5(3H)-yl)-3-(2-chlorophenoxy)-1-oxopropan-2-yl)-2-methylpropanamide Step 1: tert-butyl ((R)-1-((R)-3a-benzyl-2-methyl-3-oxo-3a,4,6,7-tetrahydro-2H-pyrazolo[4,3-c]pyridin-5(3H)-yl)-3-(2-chlorophenoxy)-1-oxopropan-2-yl)carbamate The title compound was prepared in 60% yield (66 mg, colorless solid) from (R)-3a-benzyl-2-methyl-4,5,6,7-tetrahydro-2H-pyrazolo[4,3-c]pyridin-3(3aH)-one (2R,3R)-2,3-dihydroxysuccinate (80 mg, 0.20 mmol) and (R)-2-((tert-butoxycarbonyl)amino)-3-(2-chlorophenoxy)propanoic acid (77 mg, 0.24 mmol, Step 3 of Intermediate 8) in a similar manner to Step 1 of Example 1.
MS (ESI) m/z: 541 (M+H)$^+$, 539 (M−H)$^-$.

Step 2

(R)-5-((R)-2-amino-3-(2-chlorophenoxy)propanoyl)-3a-benzyl-2-methyl-4,5,6,7-tetrahydro-2H-pyrazolo[4,3-c]pyridin-3(3aH)-one The title compound was prepared in >99% yield (58 mg) from tert-butyl ((R)-1-((R)-3a-benzyl-2-methyl-3-oxo-3a,4,6,7-tetrahydro-2H-pyrazolo[4,3-c]pyridin-5(3H)-yl)-3-(2-chlorophenoxy)-1-oxopropan-2-yl)carbamate (61 mg, 0.11 mmol) in a similar manner to Step 2 of Example 1.
MS (ESI) m/z: 441 (M+H)$^+$.

Step 3: tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(2-chlorophenoxy)-1-oxopropan-2-yl)amino)-2-methyl-1-oxopropan-2-yl)carbamate The title compound was prepared in 96% yield (79 mg, colorless gum) from (R)-5-((R)-2-amino-3-(2-chlorophenoxy)propanoyl)-3a-benzyl-2-methyl-4,5,6,7-tetrahydro-2H-pyrazolo[4,3-c]pyridin-3(3aH)-one (58 mg, 0.13 mmol) and 2-((tert-butoxycarbonyl)amino)-2-methylpropanoic acid (32 mg, 0.16 mmol) in a similar manner to Step 3 of Example 1.

MS (ESI) m/z: 626 (M+H)$^+$, 624 (M−H)$^−$.

Step 4

2-amino-N—((R)-1-((R)-3a-benzyl-2-methyl-3-oxo-3a,4,6,7-tetrahydro-2H-pyrazolo[4,3-c]pyridin-5(3H)-yl)-3-(2-chlorophenoxy)-1-oxopropan-2-yl)-2-methylpropanamide The title compound was prepared in 22% yield (13 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(2-chlorophenoxy)-1-oxopropan-2-yl)amino)-2-methyl-1-oxopropan-2-yl)carbamate (69 mg, 0.11 mmol) in a similar manner to Step 4 of Example 1.

Example 9

2-amino-N—((R)-1-((R)-3a-benzyl-2-methyl-3-oxo-3a,4,6,7-tetrahydro-2H-pyrazolo[4,3-c]pyridin-5(3H)-yl)-3-(3,5-bis(trifluoromethyl)phenoxy)-1-oxopropan-2-yl)-2-methylpropanamide

Step 1: tert-butyl ((R)-1-((R)-3a-benzyl-2-methyl-3-oxo-3a,4,6,7-tetrahydro-2H-pyrazolo[4,3-c]pyridin-5(3H)-yl)-3-(3,5-bis(trifluoromethyl)phenoxy)-1-oxopropan-2-yl)carbamate The title compound was prepared in 43% yield (54 mg, colorless gum) from (R)-3a-benzyl-2-methyl-4,5,6,7-tetrahydro-2H-pyrazolo[4,3-c]pyridin-3(3aH)-one (2R,3R)-2,3-dihydroxysuccinate (80 mg, 0.20 mmol) and (R)-3-(3,5-bis(trifluoromethyl)phenoxy)-2-((tert-butoxycarbonyl)amino)propanoic acid (100 mg, 0.24 mmol, Step 3 of Intermediate 9) in a similar manner to Step 1 of Example 1.

MS (ESI) m/z: 643 (M+H)$^+$, 641 (M−H)$^−$.

Step 2

(R)-5-((R)-2-amino-3-(3,5-bis(trifluoromethyl)phenoxy)propanoyl)-3a-benzyl-2-methyl-4,5,6,7-tetrahydro-2H-pyrazolo[4,3-c]pyridin-3(3aH)-one The title compound was prepared in 91% yield (40 mg) from tert-butyl ((R)-1-((R)-3a-benzyl-2-methyl-3-oxo-3a,4,6,7-tetrahydro-2H-pyrazolo[4,3-c]pyridin-5(3H)-yl)-3-(3,5-bis(trifluoromethyl)phenoxy)-1-oxopropan-2-yl)carbamate (52 mg, 0.081 mmol) in a similar manner to Step 2 of Example 1.

MS (ESI) m/z: 543 (M+H)$^+$.

Step 3: tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(3,5-bis(trifluoromethyl)phenoxy)-1-oxopropan-2-yl)amino)-2-methyl-1-oxopropan-2-yl)carbamate The title compound was prepared in >99% yield (55 mg, colorless gum) from (R)-5-((R)-2-amino-3-(3,5-bis(trifluoromethyl)phenoxy)propanoyl)-3a-benzyl-2-methyl-4,5,6,7-tetrahydro-2H-pyrazolo[4,3-c]pyridin-3(3aH)-one (40 mg, 0.074 mmol) and 2-((tert-butoxycarbonyl)amino)-2-methylpropanoic acid (32 mg, 0.16 mmol) in a similar manner to Step 3 of Example 1.

MS (ESI) m/z: 728 (M+H)$^+$, 726 (M−H)$^−$.

Step 4

2-amino-N—((R)-1-((R)-3a-benzyl-2-methyl-3-oxo-3a,4,6,7-tetrahydro-2H-pyrazolo[4,3-c]pyridin-5(3H)-yl)-3-(3,5-bis(trifluoromethyl)phenoxy)-1-oxopropan-2-yl)-2-methylpropanamide The title compound was prepared in 32% yield (14 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(3,5-bis(trifluoromethyl)phenoxy)-1-oxopropan-2-yl)amino)-2-methyl-1-oxopropan-2-yl)carbamate (50 mg, 0.069 mmol) in a similar manner to Step 4 of Example 1.

Example 10

2-amino-N—((R)-1-((R)-3a-benzyl-2-methyl-3-oxo-3a,4,6,7-tetrahydro-2H-pyrazolo[4,3-c]pyridin-5(3H)-yl)-3-(3-fluorophenoxy)-1-oxopropan-2-yl)-2-methylpropanamide

Step 1: tert-butyl ((R)-1-((R)-3a-benzyl-2-methyl-3-oxo-3a,4,6,7-tetrahydro-2H-pyrazolo[4,3-c]pyridin-5(3H)-yl)-3-(3-fluorophenoxy)-1-oxopropan-2-yl)carbamate The title compound was prepared in 45% yield (48 mg, colorless gum) from (R)-3a-benzyl-2-methyl-4,5,6,7-tetrahydro-2H-pyrazolo[4,3-c]pyridin-3(3aH)-one (2R,3R)-2,3-dihydroxysuccinate (80 mg, 0.20 mmol) and (R)-2-((tert-butoxycarbonyl)amino)-3-(3-fluorophenoxy)propanoic acid (79 mg, 0.26 mmol, Step 3 of Intermediate 10) in a similar manner to Step 1 of Example 1.

MS (ESI) m/z: 525 (M+H)$^+$, 523 (M−H)$^−$.

Step 2: tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(3-fluorophenoxy)-1-oxopropan-2-yl)amino)-2-methyl-1-oxopropan-2-yl)carbamate To a stirred solution of tert-butyl ((R)-1-((R)-3a-benzyl-2-methyl-3-oxo-3a,4,6,7-tetrahydro-2H-pyrazolo[4,3-c]pyridin-5(3H)-yl)-3-(3-fluorophenoxy)-1-oxopropan-2-yl)carbamate (30 mg, 0.057 mmol) in DCM (2 mL) was added trifluoroacetic acid (2 mL) in one portion at 0° C., and stirring was continued for 2 hrs at the same temperature. The mixture was concentrated in vacuo to give yellow syrup. The residue was dissolved in DCM (4 mL). The mixture was added triethylamine (0.017 mL, 0.23 mmol), and O-(benzotriazol-1-yl)-N,N,N',N'-tetramethyluronium hexafluorophosphate (HBTU, 27 mg, 0.072 mmol) at room temperature. After stirring for 1 hr, the mixture was concentrated in vacuo. The residue was passed through a short column chromatography (amino-gel, eluted with EtOAc) to give the title compound as a white solid (51 mg, >99% yield).

MS (ESI) m/z: 610 (M+H)⁺, 608 (M−H)⁻.

Step 3

2-amino-N—((R)-1-((R)-3a-benzyl-2-methyl-3-oxo-3a,4,6,7-tetrahydro-2H-pyrazolo[4,3-c]pyridin-5(3H)-yl)-3-(3-fluorophenoxy)-1-oxopropan-2-yl)-2-methylpropanamide The title compound was prepared in 32% yield (13 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(3-fluorophenoxy)-1-oxopropan-2-yl)amino)-2-methyl-1-oxopropan-2-yl)carbamate (48 mg, 0.079 mmol) in a similar manner to Step 4 of Example 1.

Example 11

2-amino-N—((R)-1-((R)-3a-benzyl-2-methyl-3-oxo-3a,4,6,7-tetrahydro-2H-pyrazolo[4,3-c]pyridin-5(3H)-yl)-3-(3-methoxyphenoxy)-1-oxopropan-2-yl)-2-methylpropanamide Step 1: tert-butyl ((R)-1-((R)-3a-benzyl-2-methyl-3-oxo-3a,4,6,7-tetrahydro-2H-pyrazolo[4,3-c]pyridin-5(3H)-yl)-3-(3-methoxyphenoxy)-1-oxopropan-2-yl)carbamate The title compound was prepared in 62% yield (85 mg, colorless gum) from (R)-3a-benzyl-2-methyl-4,5,6,7-tetrahydro-2H-pyrazolo[4,3-c]pyridin-3(3aH)-one (2R,3R)-2,3-dihydroxysuccinate (80 mg, 0.20 mmol) and (R)-2-((tert-butoxycarbonyl)amino)-3-(3-methoxyphenoxy)propanoic acid (103 mg, 0.33 mmol, Step 3 of Intermediate 11) in a similar manner to Step 1 of Example 1.

MS (ESI) m/z: 537 (M+H)⁺, 535 (M−H)⁻.

Step 2: tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(3-methoxyphenoxy)-1-oxopropan-2-yl)amino)-2-methyl-1-oxopropan-2-yl)carbamate The title compound was prepared in 96% yield (78 mg, white solid) from tert-butyl ((R)-1-((R)-3a-benzyl-2-methyl-3-oxo-3a,4,6,7-tetrahydro-2H-pyrazolo[4,3-c]pyridin-5(3H)-yl)-3-(3-methoxyphenoxy)-1-oxopropan-2-yl)carbamate (70 mg, 0.13 mmol) in a similar manner to Step 2 of Example 10.

MS (ESI) m/z: 622 (M+H)⁺, 620 (M−H)⁻.

Step 3

2-amino-N—((R)-1-((R)-3a-benzyl-2-methyl-3-oxo-3a,4,6,7-tetrahydro-2H-pyrazolo[4,3-c]pyridin-5(3H)-yl)-3-(3-methoxyphenoxy)-1-oxopropan-2-yl)-2-methylpropanamide The title compound was prepared in 18% yield (9 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(3-methoxyphenoxy)-1-oxopropan-2-yl)amino)-2-methyl-1-oxopropan-2-yl)carbamate (60 mg, 0.097 mmol) in a similar manner to Step 4 of Example 1.

Example 12

2-amino-N—((R)-1-((R)-3a-benzyl-2-methyl-3-oxo-3a,4,6,7-tetrahydro-2H-pyrazolo[4,3-c]pyridin-5(3H)-yl)-3-(2-fluorophenoxy)-1-oxopropan-2-yl)-2-methylpropanamide Step 1: tert-butyl ((R)-1-((R)-3a-benzyl-2-methyl-3-oxo-3a,4,6,7-tetrahydro-2H-pyrazolo[4,3-c]pyridin-5(3H)-yl)-3-(2-fluorophenoxy)-1-oxopropan-2-yl)carbamate The title compound was prepared in 57% yield (76 mg, colorless gum) from (R)-3a-benzyl-2-methyl-4,5,6,7-tetrahydro-2H-pyrazolo[4,3-c]pyridin-3(3aH)-one (2R,3R)-2,3-dihydroxysuccinate (100 mg, 0.25 mmol) and (R)-2-((tert-butoxycarbonyl)amino)-3-(2-fluorophenoxy)propanoic acid (114 mg, 0.38 mmol, Step 3 of Intermediate 12) in a similar manner to Step 1 of Example 1.

MS (ESI) m/z: 525 (M+H)⁺, 523 (M−H)⁻.

Step 2: tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(2-fluorophenoxy)-1-oxopropan-2-yl)amino)-2-methyl-1-oxopropan-2-yl)carbamate The title compound was prepared in >99% yield (74 mg, colorless gum) from tert-butyl ((R)-1-((R)-3a-benzyl-2-methyl-3-oxo-3a,4,6,7-tetrahydro-2H-pyrazolo[4,3-c]pyridin-5(3H)-yl)-3-(2-fluorophenoxy)-1-oxopropan-2-yl)carbamate (60 mg, 0.11 mmol) in a similar manner to Step 2 of Example 10.

MS (ESI) m/z: 610 (M+H)⁺, 608 (M−H)⁻.

Step 3

2-amino-N—((R)-1-((R)-3a-benzyl-2-methyl-3-oxo-3a,4,6,7-tetrahydro-2H-pyrazolo[4,3-c]pyridin-5(3H)-yl)-3-(2-fluorophenoxy)-1-oxopropan-2-yl)-2-methylpropanamide The title compound was prepared in 22% yield (11 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(2-fluorophenoxy)-1-oxopropan-2-yl)amino)-2-methyl-1- oxopropan-2-yl)carbamate (60 mg, 0.098 mmol) in a similar manner to Step 4 of Example 1.

Example 13

2-amino-N—((R)-1-((R)-3a-benzyl-2-methyl-3-oxo-3a,4,6,7-tetrahydro-2H-pyrazolo[4,3-c]pyridin-5(3H)-yl)-3-(naphthalen-2-yloxy)-1-oxopropan-2-yl)-2-methylpropanamide Step 1: tert-butyl ((R)-1-((R)-3a-benzyl-2-methyl-3-oxo-3a,4,6,7-tetrahydro-2H-pyrazolo[4,3-c]pyridin-5(3H)-yl)-3-(naphthalen-2-yloxy)-1-oxopropan-2-yl)carbamate The title compound was prepared in 45% yield (90 mg, white solid) from (R)-3a-benzyl-2-methyl-4,5,6,7-tetrahydro-2H-pyrazolo[4,3-c]pyridin-3(3aH)-one (2R,3R)-2,3-dihydroxysuccinate (140 mg, 0.36 mmol) and (R)-2-((tert-butoxycarbonyl)amino)-3-(naphthalen-2-yloxy)propanoic acid (130 mg, 0.39 mmol, Step 3 of Intermediate 14) in a similar manner to Step 1 of Example 1.
MS (ESI) m/z: 557 (M+H)$^+$, 555 (M−H)$^-$.

Step 2: tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(naphthalen-2-yloxy)-1-oxopropan-2-yl)amino)-2-methyl-1-oxopropan-2-yl)carbamate The title compound was prepared in >99% yield (100 mg, colorless gum) from tert-butyl ((R)-1-((R)-3a-benzyl-2-methyl-3-oxo-3a,4,6,7-tetrahydro-2H-pyrazolo[4,3-c]pyridin-5(3H)-yl)-3-(naphthalen-2-yloxy)-1-oxopropan-2-yl)carbamate (87 mg, 0.15 mmol) in a similar manner to Step 2 of Example 10.
MS (ESI) m/z: 642 (M+H)$^+$, 640 (M−H)$^-$.

Step 3

2-amino-N—((R)-1-((R)-3a-benzyl-2-methyl-3-oxo-3a,4,6,7-tetrahydro-2H-pyrazolo[4,3-c]pyridin-5(3H)-yl)-3-(naphthalen-2-yloxy)-1-oxopropan-2-yl)-2-methylpropanamide The title compound was prepared in 14% yield (13 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(naphthalen-2-yloxy)-1-oxopropan-2-yl)amino)-2-methyl-1-oxopropan-2-yl)carbamate (100 mg, 0.16 mmol) in a similar manner to Step 4 of Example 1.

Example 14

2-amino-N—((R)-1-((R)-3a-benzyl-2-methyl-3-oxo-3a,4,6,7-tetrahydro-2H-pyrazolo[4,3-c]pyridin-5(3H)-yl)-3-(naphthalen-1-yloxy)-1-oxopropan-2-yl)-2-methylpropanamide Step 1: tert-butyl ((R)-1-((R)-3a-benzyl-2-methyl-3-oxo-3a,4,6,7-tetrahydro-2H-pyrazolo[4,3-c]pyridin-5(3H)-yl)-3-(naphthalen-1-yloxy)-1-oxopropan-2-yl)carbamate The title compound was prepared in 67% yield (140 mg, colorless gum) from (R)-3a-benzyl-2-methyl-4,5,6,7-tetrahydro-2H-pyrazolo[4,3-c]pyridin-3(3aH)-one (2R,3R)-2,3-dihydroxysuccinate (150 mg, 0.38 mmol) and (R)-2-((tert-butoxycarbonyl)amino)-3-(naphthalen-1-yloxy)propanoic acid (150 mg, 0.46 mmol, Step 3 of Intermediate 15) in a similar manner to Step 1 of Example 1.
MS (ESI) m/z: 557 (M+H)$^+$, 555 (M−H)$^-$.

Step 2: tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(naphthalen-1-yloxy)-1-oxopropan-2-yl)amino)-2-methyl-1-oxopropan-2-yl)carbamate The title compound was prepared in 82% yield (120 mg, colorless gum) from tert-butyl ((R)-1-((R)-3a-benzyl-2-methyl-3-oxo-3a,4,6,7-tetrahydro-2H-pyrazolo[4,3-c]pyridin-5(3H)-yl)-3-(naphthalen-1-yloxy)-1-oxopropan-2-yl)carbamate (130 mg, 0.23 mmol) in a similar manner to Step 2 of Example 10.
MS (ESI) m/z: 642 (M+H)$^+$, 640 (M−H)$^-$.

Step 3

2-amino-N—((R)-1-((R)-3a-benzyl-2-methyl-3-oxo-3a,4,6,7-tetrahydro-2H-pyrazolo[4,3-c]pyridin-5(3H)-yl)-3-(naphthalen-1-yloxy)-1-oxopropan-2-yl)-2-methylpropanamide The title compound was prepared in 14% yield (13 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(naphthalen-1-yloxy)-1-oxopropan-2-yl)amino)-2-methyl-1-oxopropan-2-yl)carbamate (110 mg, 0.17 mmol) in a similar manner to Step 4 of Example 1.

Example 15

2-amino-N—((R)-1-((R)-3a-benzyl-2-methyl-3-oxo-3a,4,6,7-tetrahydro-2H-pyrazolo[4,3-c]pyridin-5(3H)-yl)-3-((5-chloropyridin-3-yl)oxy)-1-oxopropan-2-yl)-2-methylpropanamide Step 1: tert-butyl ((R)-1-((R)-3a-benzyl-2-methyl-3-oxo-3a,4,6,7-tetrahydro-2H-pyrazolo[4,3-c]pyridin-5(3H)-yl)-3-((5-chloropyridin-3-yl)oxy)-1-oxopropan-2-yl)carbamate The title compound was prepared in 53% yield (170 mg, colorless gum) from (R)-3a-benzyl-2-methyl-4,5,6,7-tetrahydro-2H-pyrazolo[4,3-c]pyridin-3(3aH)-one (2R,3R)-2,3-dihydroxysuccinate (250 mg, 0.64 mmol) and (R)-2-((tert-butoxycarbonyl)amino)-3-((5-chloropyridin-3-yl)oxy)propanoic acid (180 mg, 0.58 mmol, Step 2 of Intermediate 16) in a similar manner to Step 1 of Example 1.
MS (ESI) m/z: 542 (M+H)$^+$, 540 (M−H)$^-$.

Step 2: tert-butyl (1-(((R)-1-((R)-3a-benzyl-2-methyl-3-oxo-3a,4,6,7-tetrahydro-2H-pyrazolo[4,3-c]pyridin-5(3H)-yl)-3-((5-chloropyridin-3-yl)oxy)-1-oxopropan-2-yl)amino)-2-methyl-1-oxopropan-2-yl)carbamate The title compound was prepared in 86% yield (170 mg, white solid) from tert-butyl ((R)-1-((R)-3a-benzyl-2- methyl-3-oxo-3a,4,6,7-tetrahydro-2H-pyrazolo[4,3-c]pyridin-5(3H)-yl)-3-((5-chloropyridin-3-yl)oxy)-1-oxopropan-2-yl)carbamate (160 mg, 0.30 mmol) in a similar manner to Step 1 of Example 10.

MS (ESI) m/z: 627 (M+H)$^+$, 625 (M−H)$^−$.

Step 3

2-amino-N—((R)-1-((R)-3a-benzyl-2-methyl-3-oxo-3a,4,6,7-tetrahydro-2H-pyrazolo[4,3-c]pyridin-5(3H)-yl)-3-((5-chloropyridin-3-yl)oxy)-1-oxopropan-2-yl)-2-methylpropanamide The title compound was prepared in 11% yield (16 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-3-((5-chloropyridin-3-yl)oxy)-1-oxopropan-2-yl)amino)-2-methyl-1-oxopropan-2-yl)carbamate (170 mg, 0.27 mmol) in a similar manner to Step 4 of Example 1.

Example 16

2-amino-N—((R)-1-((R)-3a-benzyl-2-methyl-3-oxo-3a,4,6,7-tetrahydro-2H-pyrazolo[4,3-c]pyridin-5(3H)-yl)-3-(3-cyanophenoxy)-1-oxopropan-2-yl)-2-methylpropanamide Step 1: tert-butyl ((R)-1-((R)-3a-benzyl-2-methyl-3-oxo-3a,4,6,7-tetrahydro-2H-pyrazolo[4,3-c]pyridin-5(3H)-yl)-3-(3-cyanophenoxy)-1-oxopropan-2-yl)carbamate The title compound was prepared in 42% yield (110 mg, colorless gum) from (R)-3a-benzyl-2-methyl-4,5,6,7-tetrahydro-2H-pyrazolo[4,3-c]pyridin-3(3aH)-one (2R,3R)-2,3-dihydroxysuccinate (190 mg, 0.48 mmol) and (R)-2-((tert-butoxycarbonyl)amino)-3-(3-cyanophenoxy)propanoic acid (150 mg, 0.48 mmol, Step 3 of Intermediate 17) in a similar manner to Step 1 of Example 1.

MS (ESI) m/z: 532 (M+H)$^+$, 530 (M−H)$^−$.

Step 2: tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(3-cyanophenoxy)-1-oxopropan-2-yl)amino)-2-methyl-1-oxopropan-2-yl)carbamate The title compound was prepared in >99% yield (113 mg, colorless gum) from tert-butyl ((R)-1-((R)-3a-benzyl-2-methyl-3-oxo-3a,4,6,7-tetrahydro-2H-pyrazolo[4,3-c]pyridin-5(3H)-yl)-3-(3-cyanophenoxy)-1-oxopropan-2-yl)carbamate (86 mg, 0.16 mmol) in a similar manner to Step 2 of Example 10.

MS (ESI) m/z: 617 (M+H)$^+$, 615 (M−H)$^−$.

Step 3

2-amino-N—((R)-1-((R)-3a-benzyl-2-methyl-3-oxo-3a,4,6,7-tetrahydro-2H-pyrazolo[4,3-c]pyridin-5(3H)-yl)-3-(3-cyanophenoxy)-1-oxopropan-2-yl)-2-methylpropanamide The title compound was prepared in 14% yield (12 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(3-cyanophenoxy)-1-oxopropan-2-yl)amino)-2-methyl-1-oxopropan-2-yl)carbamate (100 mg, 0.17 mmol, Step X of Example X) in a similar manner to Step 4 of Example 1.

Example 17

2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-3-(pyridin-2-yloxy)propan-2-yl)-2-methylpropanamide Step 1: tert-butyl ((R)-1-((R)-3a-benzyl-2-methyl-3-oxo-3a,4,6,7-tetrahydro-2H-pyrazolo[4,3-c]pyridin-5(3H)-yl)-1-oxo-3-(pyridin-2-yloxy)propan-2-yl)carbamate The title compound was prepared in 68% yield (140 mg, colorless gum) from (R)-3a-benzyl-2-methyl-4,5,6,7-tetrahydro-2H-pyrazolo[4,3-c]pyridin-3(3aH)-one (2R,3R)-2,3-dihydroxysuccinate (160 mg, 0.41 mmol) and (R)-2-((tert-butoxycarbonyl)amino)-3-(pyridin-2-yloxy)propanoic acid (140 mg, 0.49 mmol, Step 2 of Intermediate 18) in a similar manner to Step 1 of Example 1.

MS (ESI) m/z: 508 (M+H)$^+$, 506 (M−H)$^−$.

Step 2: tert-butyl (1-(((R)-1-((R)-3a-benzyl-2-methyl-3-oxo-3a,4,6,7-tetrahydro-2H-pyrazolo[4,3-c]pyridin-5(3H)-yl)-1-oxo-3-(pyridin-2-yloxy)propan-2-yl)amino)-2-methyl-1-oxopropan-2-yl)carbamate The title compound was prepared in 86% yield (130 mg, colorless solid) from tert-butyl ((R)-1-((R)-3a-benzyl-2-methyl-3-oxo-3a,4,6,7-tetrahydro-2H-pyrazolo[4,3-c]pyridin-5(3H)-yl)-1-oxo-3-(pyridin-2-yloxy)propan-2-yl)carbamate (130 mg, 0.25 mmol) in a similar manner to Step 2 of Example 10.

MS (ESI) m/z: 593 (M+H)$^+$, 591 (M−H)$^−$.

Step 3

2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-3-(pyridin-2-yloxy)propan-2-yl)-2-methylpropanamide The title compound was prepared in 12% yield (12 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-1-oxo-3-(pyridin-2-yloxy)propan-2-yl)amino)-2-methyl-1-oxopropan-2-yl)carbamate (120 mg, 0.20 mmol) in a similar manner to Step 4 of Example 1.

Example 18

2-amino-N—((R)-1-((R)-3a-benzyl-2-methyl-3-oxo-3a,4,6,7-tetrahydro-2H-pyrazolo[4,3-c]pyridin-5(3H)-yl)-3-((5-fluoropyridin-3-yl)oxy)-1-oxopropan-2-yl)-2-methylpropanamide Step 1: tert-butyl ((R)-1-((R)-3a-benzyl-2-methyl-3-oxo-3a,4,6,7-tetrahydro-2H-pyrazolo[4,3-c]pyridin-5(3H)-yl)-3-((5-fluoropyridin-3-yl)oxy)-1-oxopropan-2-yl)carbamate The title compound was prepared in 58% yield (120 mg, colorless solid) from (R)-3a-benzyl-2-methyl-4,5,6,7-tetrahydro-2H-pyrazolo[4,3-c]pyridin-3(3aH)-one (2R,3R)-2,3-dihydroxysuccinate (150 mg, 0.38 mmol) and (R)-2-((tert-butoxycarbonyl)amino)-3-((5-fluoropyridin-3-yl)oxy) propanoic acid (130 mg, 0.42 mmol, Step 2 of Intermediate 19) in a similar manner to Step 1 of Example 1.

MS (ESI) m/z: 526 (M+H)⁺, 524 (M–H)⁻

Step 2: tert-butyl (1-(((R)-1-((R)-3a-benzyl-2-methyl-3-oxo-3a,4,6,7-tetrahydro-2H-pyrazolo[4,3-c]pyridin-5(3H)-yl)-3-((5-fluoropyridin-3-yl)oxy)-1-oxopropan-2-yl) amino)-2-methyl-1-oxopropan-2-yl)carbamate The title compound was prepared in 95% yield (120 mg, colorless gum) from tert-butyl ((R)-1-((R)-3a-benzyl-2-methyl-3-oxo-3a,4,6,7-tetrahydro-2H-pyrazolo[4,3-c]pyridin-5(3H)-yl)-3-((5-fluoropyridin-3-yl)oxy)-1-oxopropan-2-yl)carbamate (110 mg, 0.20 mmol) in a similar manner to Step 2 of Example 10.

MS (ESI) m/z: 611 (M+H)⁺, 609 (M–H)⁻.

Step 3

2-amino-N—((R)-1-((R)-3a-benzyl-2-methyl-3-oxo-3a,4,6,7-tetrahydro-2H-pyrazolo[4,3-c]pyridin-5(3H)-yl)-3-((5-fluoropyridin-3-yl)oxy)-1-oxopropan-2-yl)-2-methylpropanamide The title compound was prepared in 15% yield (13 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-3-((5-fluoropyridin-3-yl)oxy)-1-oxopropan-2-yl)amino)-2-methyl-1-oxopropan-2-yl)carbamate (110 mg, 0.17 mmol) in a similar manner to Step 4 of Example 1.

Example 19

2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-3-((6-(trifluoromethyl)pyridin-2-yl)oxy)propan-2-yl)-2-methylpropanamide Step 1: tert-butyl ((R)-1-((R)-3a-benzyl-2-methyl-3-oxo-3a,4,6,7-tetrahydro-2H-pyrazolo[4,3-c]pyridin-5(3H)-yl)-1-oxo-3-((6-(trifluoromethyl)pyridin-2-yl)oxy)propan-2-yl) carbamate The title compound was prepared in 78% yield (170 mg, colorless solid) from (R)-3a-benzyl-2-methyl-4,5,6,7-tetrahydro-2H-pyrazolo[4,3-c]pyridin-3(3aH)-one (2R,3R)-2,3-dihydroxysuccinate (150 mg, 0.38 mmol) and (R)-2-((tert-butoxycarbonyl)amino)-3-((6-(trifluoromethyl)pyridin-2-yl)oxy)propanoic acid (150 mg, 0.42 mmol, Step 2 of Intermediate 20) in a similar manner to Step 1 of Example 1.

MS (ESI) m/z: 576 (M+H)⁺, 574 (M–H)⁻

Step 2: tert-butyl (1-(((R)-1-((R)-3a-benzyl-2-methyl-3-oxo-3a,4,6,7-tetrahydro-2H-pyrazolo[4,3-c]pyridin-5(3H)-yl)-1-oxo-34(6-(trifluoromethyl)pyridin-2-yl)oxy)propan-2-yl)amino)-2-methyl-1-oxopropan-2-yl)carbamate The title compound was prepared in 98% yield (180 mg, colorless gum) from tert-butyl ((R)-1-((R)-3a-benzyl-2-methyl-3-oxo-3a,4,6,7-tetrahydro-2H-pyrazolo[4,3-c]pyridin-5(3H)-yl)-1-oxo-3-((6-(trifluoromethyl)pyridin-2-yl)oxy)propan-2-yl)carbamate (160 mg, 0.28 mmol) in a similar manner to Step 2 of Example 10.

MS (ESI) m/z: 661 (M+H)⁺, 659 (M–H)⁻.

Step 3

2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-3-((6-(trifluoromethyl)pyridin-2-yl)oxy)propan-2-yl)-2-methylpropanamide The title compound was prepared in 8% yield (12 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-1-oxo-34(6-(trifluoromethyl)pyridin-2-yl)oxy)propan-2-yl)amino)-2-methyl-1-oxopropan-2-yl)carbamate (170 mg, 0.26 mmol) in a similar manner to Step 4 of Example 1.

Example 20

2-amino-N—((R)-1-((R)-3a-benzyl-2-methyl-3-oxo-3a,4,6,7-tetrahydro-2H-pyrazolo[4,3-c]pyridin-5(3H)-yl)-3-(4-cyanophenoxy)-1-oxopropan-2-yl)-2-methylpropanamide Step 1: tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(4-cyanophenoxy)-1-oxopropan-2-yl)amino)-2-methyl-1-oxopropan-2-yl)carbamate The title compound was prepared in 36% yield (29 mg, white solid) from (R)-3a-benzyl-2-methyl-4,5,6,7-tetrahydro-2H-pyrazolo[4,3-c]pyridin-3(3aH)-one (2R,3R)-2,3-dihydroxysuccinate (51 mg, 0.13 mmol) and (R)-2-(2-((tert-butoxycarbonyl)amino)-2-methylpropanamido)-3-(4-cyanophenoxy)propanoic acid (51 mg, 0.13 mmol, Step 3 of Intermediate 13) in a similar manner to Step 1 of Example 1.

MS (ESI) m/z: 617 (M+H)⁺, 617 (M–H)⁻

Step 2

2-amino-N—((R)-1-((R)-3a-benzyl-2-methyl-3-oxo-3a,4,6,7-tetrahydro-2H-pyrazolo[4,3-c]pyridin-5(3H)-yl)-3-(4-cyanophenoxy)-1-oxopropan-2-yl)-2-methylpropanamide The title compound was prepared in 54% yield (13 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(4-cyanophenoxy)-1-oxopropan-2-yl)amino)-2-methyl-1-oxopropan-2-yl)carbamate (29 mg, 0.047 mmol) in a similar manner to Step 4 of Example 1.

Example 21

2-amino-N—((R)-1-((R)-3a-benzyl-2-(2,2-difluoroethyl)-3-oxo-3a,4,6,7-tetrahydro-2H-pyrazolo[4,3-c]pyridin-5(3H)-yl)-1-oxo-3-phenoxypropan-2-yl)-2-methylpropanamide

Step 1: tert-butyl ((2R)-1-(3a-benzyl-2-(2,2-difluoroethyl)-3-oxo-3a,4,6,7-tetrahydro-2H-pyrazolo[4,3-c]pyridin-5(3H)-yl)-1-oxo-3-phenoxypropan-2-yl)carbamate (Diastereomer Mixture)

The title compound was prepared in 84% yield (120 mg, colorless gum) from 3a-benzyl-2-(2,2-difluoroethyl)-4,5,6,7-tetrahydro-2H-pyrazolo[4,3-c]pyridin-3(3aH)-one 2,2,2-trifluoroacetate (100 mg, 0.26 mmol, Step 2 of Nucleus 1) and (R)-2-((tert-butoxycarbonyl)amino)-3-phenoxypropanoic acid (86 mg, 0.31 mmol, Step 3 of Intermediate 2) in a similar manner to Step 1 of Example 1.
MS (ESI) m/z: 557 (M+H)$^+$, 555 (M−H)

Step 2: tert-butyl (1-(((2R)-1-(3a-benzyl-2-(2,2-difluoroethyl)-3-oxo-3a,4,6,7-tetrahydro-2H-pyrazolo[4,3-c]pyridin-5(3H)-yl)-1-oxo-3-phenoxypropan-2-yl)amino)-2-methyl-1-oxopropan-2-yl)carbamate (Diastereomer Mixture)

The title compound was prepared in >99% yield (200 mg, white solid) from tert-butyl ((2R)-1-(3a-benzyl-2-(2,2-difluoroethyl)-3-oxo-3a,4,6,7-tetrahydro-2H-pyrazolo[4,3-c]pyridin-5(3H)-yl)-1-oxo-3-phenoxypropan-2-yl)carbamate (120 mg, 0.22 mmol) in a similar manner to Step 2 of Example 10.
MS (ESI) m/z: 642 (M+H)$^+$, 640 (M−H)$^−$.

Step 3

2-amino-N—((R)-1-((R)-3a-benzyl-2-(2,2-difluoroethyl)-3-oxo-3a,4,6,7-tetrahydro-2H-pyrazolo[4,3-c]pyridin-5(3H)-yl)-1-oxo-3-phenoxypropan-2-yl)-2-methylpropanamide The title compound was prepared in 6% yield (10 mg) from tert-butyl (1-(((2R)-1-(3a-benzyl-2-(2,2-difluoroethyl)-3-oxo-3a,4,6,7-tetrahydro-2H-pyrazolo[4,3-c]pyridin-5(3H)-yl)-1-oxo-3-phenoxypropan-2-yl)amino)-2-methyl-1-oxopropan-2-yl)carbamate (200 mg, 0.31 mmol) in a similar manner to Step 4 of Example 1.
In this case, the desired diastereomer was collected as a more polar one under the preparative LC-MS condition.

Example 22

2-amino-N—((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-1-oxo-3-phenoxypropan-2-yl)-2-methylpropanamide

Step 1: tert-butyl ((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-1-oxo-3-phenoxypropan-2-yl)carbamate The title compound was prepared in 40% yield (50 mg, colorless gum) from (R)-2-(2,2-difluoroethyl)-3a-(pyridin-2-ylmethyl)-4,5,6,7-tetrahydro-2H-pyrazolo[4,3-c]pyridin-3(3aH)-one (2S,3S)-2,3-dihydroxysuccinate (100 mg, 0.23 mmol, Step 3 of Nucleus 2) and (R)-2-((tert-butoxycarbonyl)amino)-3-phenoxypropanoic acid (76 mg, 0.27 mmol, Step 3 of Intermediate 2) in a similar manner to Step 1 of Example 1.
MS (ESI) m/z: 558 (M+H)$^+$, 556 (M−H)$^−$.

Step 2

(R)-5-((R)-2-amino-3-phenoxypropanoyl)-2-(2,2-difluoroethyl)-3a-(pyridin-2-ylmethyl)-4,5,6,7-tetrahydro-2H-pyrazolo[4,3-c]pyridin-3(3aH)-one To a stirred solution of tert-butyl ((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-1-oxo-3-phenoxypropan-2-yl)carbamate (50 mg, 0.090 mmol) in DCM (1 mL) was added trifluoroacetic acid (5 mL) at room temperature, and the mixture was stirred for 30 min at the same temperature. The mixture was concentrated in vacuo. The residue was purified by a strong cation exchange cartridge (Isolute (registered trademark) SCX, 1 g/6 mL, Biotage) to give the title compound as a clear colorless gum (35 mg, 84% yield).
MS (ESI) m/z: 458 (M+H)$^+$.

Step 3

2-amino-N—((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-1-oxo-3-phenoxypropan-2-yl)-2-methylpropanamide A solution of (R)-5-((R)-2-amino-3-phenoxypropanoyl)-2-(2,2-difluoroethyl)-3a-(pyridin-2-ylmethyl)-4,5,6,7-tetrahydro-2H-pyrazolo[4,3-c]pyridin-3(3aH)-one (34 mg, 0.074 mmol) and 2-((tert-butoxycarbonyl)amino)-2-methylpropanoic acid (18 mg, 0.089 mmol) in EtOAc (2 mL) cooled to 0° C. To the mixture, triethylamine (0.031 mL, 0.22 mmol) and 2,4,6-tripropyl-1,3,5,2,4,6-trioxatriphosphinane 2,4,6-trioxide (0.087 mL, 0.15 mmol; 1.7 M solution in EtOAc) were added successively, and the resulting mixture was stirred for 1 hr at the same temperature. The mixture was concentrated in vacuo. Then, trifluoroacetic acid (2 mL) was added to the residue and the mixture was stirred for 30 min at room temperature. The mixture was concentrated in vacuo. The residue was purified by strong cation exchange cartridge (BondElute (registered trademark) SCX, 1 g/6 mL, Varian Inc.), and then further purified by preparative LC-MS to give 10 mg (25% yield) of the title compound.

Example 23

2-amino-N—((R)-3-(2-chlorophenoxy)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-1-oxopropan-2-yl)-2-methylpropanamide

Step 1: tert-butyl ((R)-3-(2-chlorophenoxy)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-1-oxopropan-2-yl)carbamate The title compound was prepared in 30% yield (40 mg, colorless gum) from (R)-2-(2,2-difluoroethyl)-3a-(pyridin- 2-ylmethyl)-4,5,6,7-tetrahydro-2H-pyrazolo[4,3-c]pyridin-3(3aH)-one (2S,3S)-2,3-dihydroxysuccinate (100 mg, 0.23 mmol, Step 3 of Nucleus 2) and (R)-2-((tert-butoxycarbonyl)amino)-3-(2-chlorophenoxy)propanoic acid (85 mg, 0.27 mmol, Step 3 of Intermediate 8) in a similar manner to Step 1 of Example 1.

MS (ESI) m/z: 592 (M+H)⁺, 590 (M−H)⁻.

Step 2

(R)-5-((R)-2-amino-3-(2-chlorophenoxy)propanoyl)-2-(2,2-difluoroethyl)-3a-(pyridin-2-ylmethyl)-4,5,6,7-tetrahydro-2H-pyrazolo[4,3-c]pyridin-3(3aH)-one The title compound was prepared in 89% yield (33 mg, colorless oil) from tert-butyl ((R)-3-(2-chlorophenoxy)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-1-oxopropan-2-yl)carbamate (40 mg, 0.068 mmol) in a similar manner to Step 2 of Example 22.

MS (ESI) m/z: 492 (M+H)⁺.

Step 3

2-amino-N—((R)-3-(2-chlorophenoxy)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-1-oxopropan-2-yl)-2-methylpropanamide The title compound was prepared in 28% yield (10 mg) from (R)-5-((R)-2-amino-3-(2-chlorophenoxy)propanoyl)-2-(2,2-difluoroethyl)-3a-(pyridin-2-ylmethyl)-4,5,6,7-tetrahydro-2H-pyrazolo[4,3-c]pyridin-3(3aH)-one (30 mg, 0.060 mmol) in a similar manner to Step 3 of Example 22.

Example 24

2-amino-N—((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-3-(2-fluorophenoxy)-1-oxopropan-2-yl)-2-methylpropanamide Step 1: tert-butyl ((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-3-(2-fluorophenoxy)-1-oxopropan-2-yl)carbamate The title compound was prepared in 31% yield (41 mg, colorless gum) from (R)-2-(2,2-difluoroethyl)-3a-(pyridin-2-ylmethyl)-4,5,6,7-tetrahydro-2H-pyrazolo[4,3-c]pyridin-3(3aH)-one (2S,3S)-2,3-dihydroxysuccinate (100 mg, 0.23 mmol, Step 3 of Nucleus 2) and (R)-2-((tert-butoxycarbonyl)amino)-3-(2-fluorophenoxy)propanoic acid (81 mg, 0.27 mmol, Step 3 of Intermediate 12) in a similar manner to Step 1 of Example 1.

MS (ESI) m/z: 576 (M+H)⁺, 574 (M−H)⁻.

Step 2

(R)-5-((R)-2-amino-3-(2-fluorophenoxy)propanoyl)-2-(2,2-difluoroethyl)-3a-(pyridin-2-ylmethyl)-4,5,6,7-tetrahydro-2H-pyrazolo[4,3-c]pyridin-3(3aH)-one The title compound was prepared in 92% yield (31 mg, colorless oil) from tert-butyl ((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-3-(2-fluorophenoxy)-1-oxopropan-2-yl)carbamate (41 mg, 0.071 mmol) in a similar manner to Step 2 of Example 22.

MS (ESI) m/z: 476 (M+H)⁺.

Step 3

2-amino-N—((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-3-(2-fluorophenoxy)-1-oxopropan-2-yl)-2-methylpropanamide The title compound was prepared in 30% yield (11 mg) from (R)-5-((R)-2-amino-3-(2-fluorophenoxy)propanoyl)-2-(2,2-difluoroethyl)-3a-(pyridin-2-ylmethyl)-4,5,6,7-tetrahydro-2H-pyrazolo[4,3-c]pyridin-3(3aH)-one (31 mg, 0.065 mmol) in a similar manner to Step 3 of Example 22.

Example 25

2-amino-N—((R)-3-(3-chlorophenoxy)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-1-oxopropan-2-yl)-2-methylpropanamide Step 1: tert-butyl ((R)-3-(3-chlorophenoxy)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-1-oxopropan-2-yl)carbamate The title compound was prepared in 37% yield (49 mg, colorless gum) from (R)-2-(2,2-difluoroethyl)-3a-(pyridin-2-ylmethyl)-4,5,6,7-tetrahydro-2H-pyrazolo[4,3-c]pyridin-3(3aH)-one (2S,3S)-2,3-dihydroxysuccinate (100 mg, 0.23 mmol, Step 3 of Nucleus 2) and (R)-2-((tert-butoxycarbonyl)amino)-3-(3-chlorophenoxy)propanoic acid (85 mg, 0.27 mmol, Step 3 of Intermediate 4) in a similar manner to Step 1 of Example 1.

MS (ESI) m/z: 592 (M+H)⁺, 590 (M−H)⁻.

Step 2

(R)-5-((R)-2-amino-3-(3-chlorophenoxy)propanoyl)-2-(2,2-difluoroethyl)-3a-(pyridin-2-ylmethyl)-4,5,6,7-tetrahydro-2H-pyrazolo[4,3-c]pyridin-3(3aH)-one The title compound was prepared in 87% yield (36 mg, colorless oil) from tert-butyl ((R)-3-(3-chlorophenoxy)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-1-oxopropan-2-yl)carbamate (49 mg, 0.083 mmol) in a similar manner to Step 2 of Example 22.

MS (ESI) m/z: 492 (M+H)⁺.

Step 3

2-amino-N—((R)-3-(3-chlorophenoxy)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-1-oxopropan-2-yl)-2-methylpropanamide The title compound was prepared in 22% yield (9 mg) from (R)-5-((R)-2-amino-3-(3-chlorophenoxy)propanoyl)-2-(2,2-difluoroethyl)-3a-(pyridin-2-ylmethyl)-4,5,6,7-tetrahydro-2H-pyrazolo[4,3-c]pyridin-3(3aH)-one (36 mg, 0.072 mmol, Step 3 of Example 22) in a similar manner to Step 3 of Example 22.

Example 26

2-amino-N—((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-3-(3-methoxyphenoxy)-1-oxopropan-2-yl)-2-methylpropanamide Step 1: tert-butyl (R)-1-((R)-2-(2,2-difluoroethyl)-3-oxo-3a-(pyridin-2-ylmethyl)-3a,4,6,7-tetrahydro-2H-pyrazolo[4,3-c]pyridin-5 (3H)-yl)-3-(3-methoxyphenoxy)-1-oxopropan-2-yl)carbamate The title compound was prepared in 48% yield (64 mg, colorless gum) from (R)-2-(2,2-difluoroethyl)-3a-(pyridin-2-ylmethyl)-4,5,6,7-tetrahydro-2H-pyrazolo[4,3-c]pyridin-3(3aH)-one (2S,3S)-2,3-dihydroxysuccinate (100 mg, 0.23 mmol, Step 3 of Nucleus 2) and (R)-2-((tert-butoxycarbonyl)amino)-3-(3-methoxyphenoxy)propanoic acid (84 mg, 0.27 mmol, Step 3 of Intermediate 11) in a similar manner to Step 1 of Example 1. MS (ESI) m/z: 588 (M+H)$^+$, 586 (M−H)$^−$.

Step 2

(R)-5-((R)-2-amino-3-(3-methoxyphenoxy)propanoyl)-2-(2,2-difluoroethyl)-3a-(pyridin-2-ylmethyl)-4,5,6,7-tetrahydro-2H-pyrazolo[4,3-c]pyridin-3(3aH)-one The title compound was prepared in 82% yield (43 mg, colorless oil) from tert-butyl ((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-3-(3-methoxyphenoxy)-1-oxopropan-2-yl)carbamate (64 mg, 0.11 mmol) in a similar manner to Step 2 of Example 22.
MS (ESI) m/z: 488 (M+H)$^+$.

Step 3

2-amino-N—((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-3-(3-methoxyphenoxy)-1-oxopropan-2-yl)-2-methylpropanamide The title compound was prepared in 24% yield (12 mg) from (R)-5-((R)-2-amino-3-(3-methoxyphenoxy)propanoyl)-2-(2,2-difluoroethyl)-3a-(pyridin-2-ylmethyl)-4,5,6,7-tetrahydro-2H-pyrazolo[4,3-c]pyridin-3(3aH)-one (43 mg, 0.089 mmol) in a similar manner to Step 3 of Example 22.

Example 27

2-amino-N—((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-3-(3-fluorophenoxy)-1-oxopropan-2-yl)-2-methylpropanamide Step 1: tert-butyl ((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-3-(3-fluorophenoxy)-1-oxopropan-2-yl)carbamate The title compound was prepared in 36% yield (47 mg, colorless gum) from (R)-2-(2,2-difluoroethyl)-3a-(pyridin-2-ylmethyl)-4,5,6,7-tetrahydro-2H-pyrazolo[4,3-c]pyridin-3(3aH)-one (2S,3S)-2,3-dihydroxysuccinate (100 mg, 0.23 mmol, Step 3 of Nucleus 2) and (R)-2-((tert-butoxycarbonyl)amino)-3-(3-fluorophenoxy)propanoic acid (100 mg, 0.34 mmol, Step 3 of Intermediate 10) in a similar manner to Step 1 of Example 1.
MS (ESI) m/z: 576 (M+H)$^+$, 574 (M−H)$^−$.

Step 2

(R)-5-((R)-2-amino-3-(3-fluorophenoxy)propanoyl)-2-(2,2-difluoroethyl)-3a-(pyridin-2-ylmethyl)-4,5,6,7-tetrahydro-2H-pyrazolo[4,3-c]pyridin-3(3aH)-one The title compound was prepared in 91% yield (35 mg, colorless oil) from tert-butyl ((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-3-(3-fluorophenoxy)-1-oxopropan-2-yl)carbamate (47 mg, 0.082 mmol) in a similar manner to Step 2 of Example 22.
MS (ESI) m/z: 476 (M+H)$^+$.

Step 3

2-amino-N—((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-3-(3-fluorophenoxy)-1-oxopropan-2-yl)-2-methylpropanamide The title compound was prepared in 36% yield (15 mg) from (R)-5-((R)-2-amino-3-(3-fluorophenoxy)propanoyl)-2-(2,2-difluoroethyl)-3a-(pyridin-2-ylmethyl)-4,5,6,7-tetrahydro-2H-pyrazolo[4,3-c]pyridin-3(3aH)-one (35 mg, 0.074 mmol) in a similar manner to Step 3 of Example 22.

Example 28

2-amino-N—((R)-1-((R)-3a-benzyl-2-methyl-3-oxo-3a,4,6,7-tetrahydro-2H-pyrazolo[4,3-c]pyridin-5(3H)-yl)-3-(4-fluorophenoxy)-1-oxopropan-2-yl)-2-methylpropanamide Step 1: tert-butyl ((R)-1-((R)-3a-benzyl-2-methyl-3-oxo-3a,4,6,7-tetrahydro-2H-pyrazolo[4,3-c]pyridin-5(3H)-yl)-3-(4-fluorophenoxy)-1-oxopropan-2-yl)carbamate The title compound was prepared in 56% yield (45 mg, white solid) from (R)-3a-benzyl-2-methyl-4,5,6,7-tetrahydro-2H-pyrazolo[4,3-c]pyridin-3(3aH)-one (2R,3R)-2,3- dihydroxysuccinate (60 mg, 0.15 mmol) and (R)-2-((tert-butoxycarbonyl)amino)-3-(4-fluorophenoxy)propanoic acid (45 mg, 0.15 mmol, Step 2 of Intermediate 16) in a similar manner to Step 1 of Example 1.

MS (ESI) m/z: 525 (M+H)⁺, 523 (M−H)⁻.

Step 2

(R)-5-((R)-2-amino-3-(4-fluorophenoxy)propanoyl)-3a-benzyl-2-methyl-4,5,6,7-tetrahydro-2H-pyrazolo[4,3-c]pyridin-3(3aH)-one The title compound was prepared in quantitative yield (37 mg, colorless oil) from tert-butyl ((R)-1-((R)-3a-benzyl-2-methyl-3-oxo-3a,4,6,7-tetrahydro-2H-pyrazolo[4,3-c]pyridin-5(3H)-yl)-3-(4-fluorophenoxy)-1-oxopropan-2-yl)carbamate (45 mg, 0.086 mmol) in a similar manner to Step 2 of Example 1.

Step 3: tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(4-fluorophenoxy)-1-oxopropan-2-yl)amino)-2-methyl-1-oxopropan-2-yl)carbamate The title compound was prepared in 96% yield (50 mg, colorless oil) from (R)-5-((R)-2-amino-3-(4-fluorophenoxy)propanoyl)-3a-benzyl-2-methyl-4,5,6,7-tetrahydro-2H-pyrazolo[4,3-c]pyridin-3(3aH)-one (37 mg, 0.86 mmol) and 2-((tert-butoxycarbonyl)amino)-2-methylpropanoic acid (26 mg, 1.3 mmol) in a similar manner to Step 3 of Example 1.

MS (ESI) m/z: 610 (M+H)⁺.

Step 4

2-amino-N-((R)-1-((R)-3a-benzyl-2-methyl-3-oxo-3a,4,6,7-tetrahydro-2H-pyrazolo[4,3-c]pyridin-5(3H)-yl)-3-(4-fluorophenoxy)-1-oxopropan-2-yl)-2-methylpropanamide The title compound was prepared in 22% yield (11 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-3-(4-fluorophenoxy)-1-oxopropan-2-yl)amino)-2-methyl-1-oxopropan-2-yl)carbamate (45 mg, 0.074 mmol) in a similar manner to Step 4 of Example 1.

Condition for the preparative LC-MS and quality check (QC) method are shown in Table 5.

TABLE 5

| Example | Name | Structure | tR (min) | m/z | Ion mode | Condition | Method |
|---|---|---|---|---|---|---|---|
| 1 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(2,4-difluorophenoxy)-1-oxopropan-2-yl)-2-methylpropanamide | 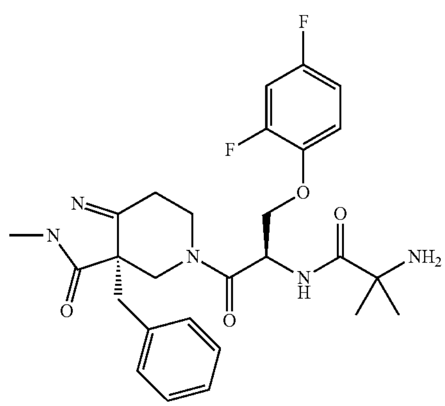 [SMILES: CNC(=O)[C@]1(Cc2ccccc2)CN(C(=O)[C@@H](COc2ccc(F)cc2F)NC(=O)C(C)(C)N)CCC1=N] | 1.49 | 528.3 | (M + H)⁺ | A | QC1 |
| 2 | 2-amino-N-((R)-1-((R)-3a-benzyl-2-methyl-3-oxo-3a,4,6,7-tetrahydro-2H-pyrazolo[4,3-c]pyridin-5(3H)-yl)-1-oxo-3-phenoxypropan-2-yl)-2-methylpropanamide | 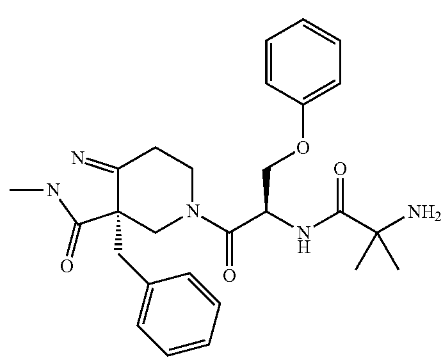 [SMILES: CNC(=O)[C@]1(Cc2ccccc2)CN(C(=O)[C@@H](COc2ccccc2)NC(=O)C(C)(C)N)CCC1=N] | 1.44 | 492.3 | (M + H)⁺ | A | QC1 |

TABLE 5-continued

| Example | Name | Structure | tR (min) | m/z | Ion mode | Condition | Method |
|---|---|---|---|---|---|---|---|
| 3 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(4-chlorophenoxy)-1-oxo-propan-2-yl)-2-methyl-propanamide | 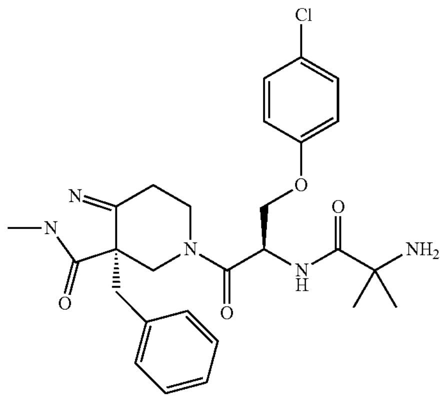 [SMILES: CNC(=O)[C@]1(Cc2ccccc2)CN(C(=O)[C@@H](COc2ccc(Cl)cc2)NC(=O)C(C)(C)N)CCC1=N] | 1.55 | 526.3 | (M + H)+ | A | QC1 |
| 4 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(3-chlorophenoxy)-1-oxo-propan-2-yl)-2-methyl-propanamide | 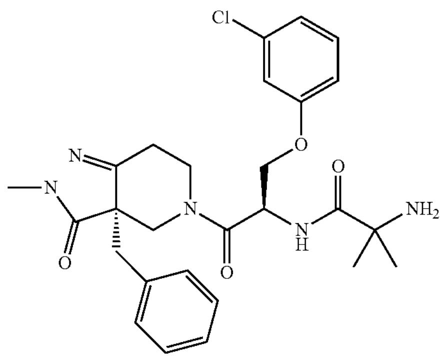 [SMILES: CNC(=O)[C@]1(Cc2ccccc2)CN(C(=O)[C@@H](COc2cccc(Cl)c2)NC(=O)C(C)(C)N)CCC1=N] | 1.56 | 526.2 | (M + H)+ | A | QC1 |
| 5 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(3,5-dichlorophenoxy)-1-oxopropan-2-yl)-2-methylpropanamide | 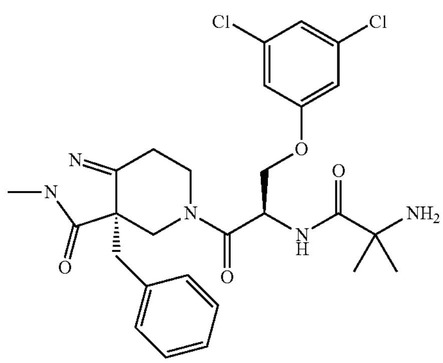 [SMILES: CNC(=O)[C@]1(Cc2ccccc2)CN(C(=O)[C@@H](COc2cc(Cl)cc(Cl)c2)NC(=O)C(C)(C)N)CCC1=N] | 1.69 | 560.2 | (M + H)+ | A | QC1 |
| 6 | 2-amino-N-((R)-1-((R)-3a-benzyl-2-methyl-3-oxo-3a,4,6,7-tetrahydro-2H-pyrazolo[4,3-c]pyridin-5(3H)-yl)-1-oxo-3-(2-trifluoromethyl)phenoxy)propan-2-yl)-2-methylpropanamide | 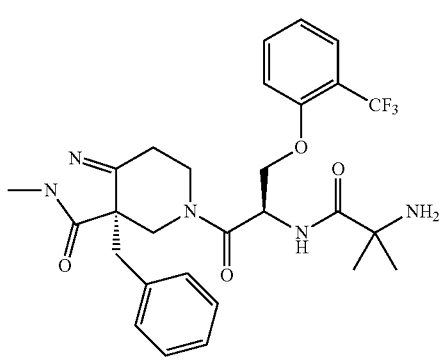 [SMILES: CNC(=O)[C@]1(Cc2ccccc2)CN(C(=O)[C@@H](COc2ccccc2C(F)(F)F)NC(=O)C(C)(C)N)CCC1=N] | 2.16 | 558.2 | (M − H) | A | QC2 |

TABLE 5-continued

| Example | Name | Structure | tR (min) | m/z | Ion mode | Condition | Method |
|---|---|---|---|---|---|---|---|
| 7 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(3,4-difluorophenoxy)-1-oxopropan-2-yl)-2-methylpropanamide | 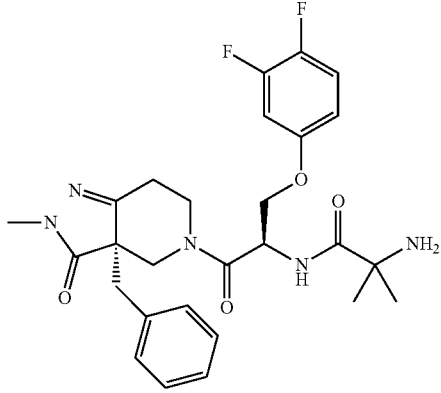 [SMILES: CNC(=O)[C@]1(Cc2ccccc2)CN(C(=O)[C@@H](COc2ccc(F)c(F)c2)NC(=O)C(C)(C)N)CCC1=N] | 2.04 | 526.1 | (M − H)⁻ | A | QC2 |
| 8 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(2-chlorophenoxy)-1-oxopropan-2-yl)-2-methylpropanamide | 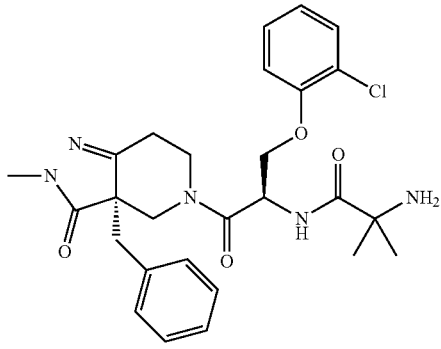 [SMILES: CNC(=O)[C@]1(Cc2ccccc2)CN(C(=O)[C@@H](COc2ccccc2Cl)NC(=O)C(C)(C)N)CCC1=N] | 2.08 | 524.2 | (M − H)⁻ | A | QC2 |
| 9 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(3,5-bis(trifluoromethyl)phenoxy)-1-oxopropan-2-yl)-2-methylpropanamide | 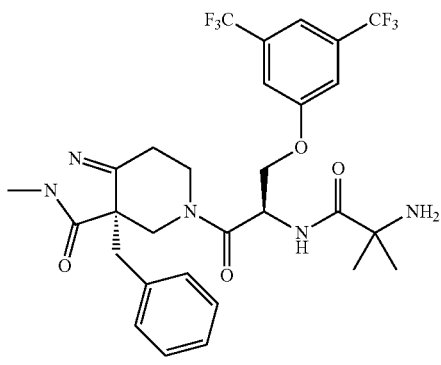 [SMILES: CNC(=O)[C@]1(Cc2ccccc2)CN(C(=O)[C@@H](COc2cc(C(F)(F)F)cc(C(F)(F)F)c2)NC(=O)C(C)(C)N)CCC1=N] | 2.46 | 626.2 | (M − H)⁻ | A | QC2 |
| 10 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(3-fluorophenoxy)-1-oxopropan-2-yl)-2-methylpropanamide | 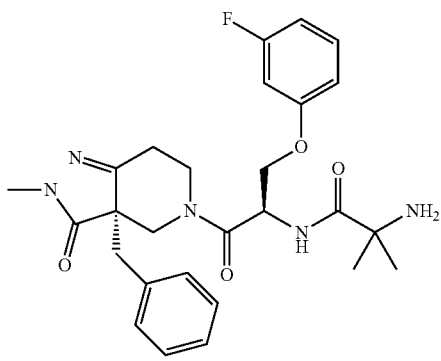 | 1.46 | 508.3 | (M + H)⁺ | A | QC1 |

TABLE 5-continued

| Example | Name | Structure | tR (min) | m/z | Ion mode | Condition | Method |
|---|---|---|---|---|---|---|---|
| 11 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(3-methoxyphenoxy)-1-oxo-propan-2-yl)-2-methyl-propanamide | 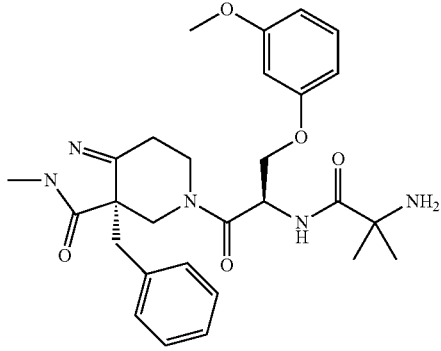 [SMILES: CNC(=O)[C@]1(Cc2ccccc2)CN(C(=O)[C@@H](COc2cccc(OC)c2)NC(=O)C(C)(C)N)CCC1=N] | 1.44 | 520.3 | (M − H)⁻ | A | QC1 |
| 12 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(2-fluorophenoxy)-1-oxo-propan-2-yl)-2-methyl-propanamide | 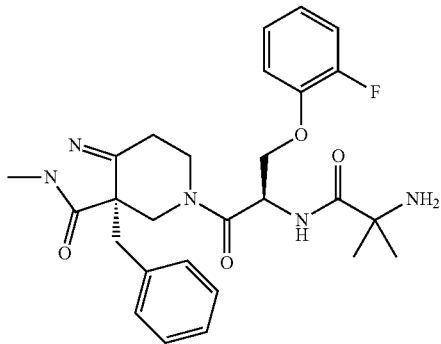 [SMILES: CNC(=O)[C@]1(Cc2ccccc2)CN(C(=O)[C@@H](COc2ccccc2F)NC(=O)C(C)(C)N)CCC1=N] | 1.44 | 508.3 | (M − H)⁻ | A | QC1 |
| 13 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(naphthalen-2-yloxy)-1-oxopropan-2-yl)-2-methylpropanamide | 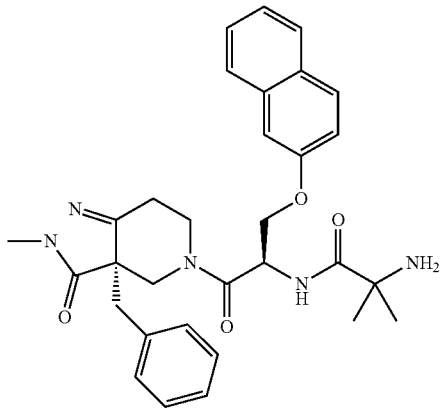 [SMILES: CNC(=O)[C@]1(Cc2ccccc2)CN(C(=O)[C@@H](COc2ccc3ccccc3c2)NC(=O)C(C)(C)N)CCC1=N] | 1.60 | 542.2 | (M + H)⁺ | A | QC1 |
| 14 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(naphthalen-1-yloxy)-1-oxopropan-2-yl)-2-methylpropanamide | 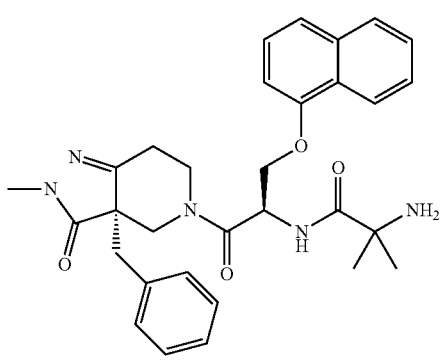 [SMILES: CNC(=O)[C@]1(Cc2ccccc2)CN(C(=O)[C@@H](COc2cccc3ccccc23)NC(=O)C(C)(C)N)CCC1=N] | 1.60 | 542.3 | (M + H)⁺ | A | QC1 |

TABLE 5-continued

| Example | Name | Structure | tR (min) | m/z | Ion mode | Condition | Method |
|---|---|---|---|---|---|---|---|
| 15 | 2-amino-N-((R)-1-((R)-3a-benzyl-2-methyl-3-oxo-3a,4,6,7-tetrahydro-2H-pyrazolo[4,3-c]pyridin-5(3H)-yl)-3-((5-chloropyridin-3-yl)oxy)-1-oxopropan-2-yl)-2-methylpropanamide | 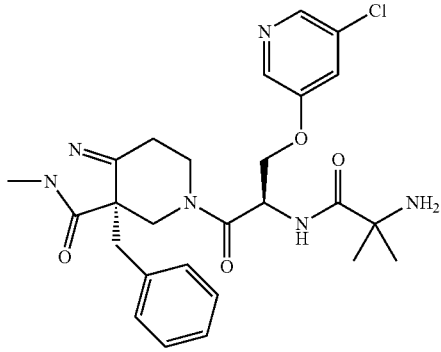 [SMILES: CNC(=O)[C@]1(Cc2ccccc2)CN(C(=O)[C@@H](COc2cncc(Cl)c2)NC(=O)C(C)(C)N)CCC1=N] | 1.35 | 527.1 | (M + H)+ | A | QC1 |
| 16 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(3-cyanophenoxy)-1-oxopropan-2-yl)-2-methyl-propanamide | 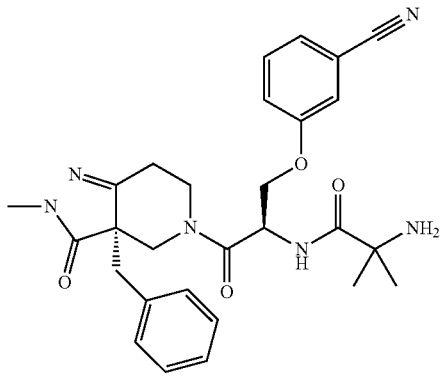 [SMILES: CNC(=O)[C@]1(Cc2ccccc2)CN(C(=O)[C@@H](COc2cccc(C#N)c2)NC(=O)C(C)(C)N)CCC1=N] | 1.39 | 517.2 | (M + H)+ | A | QC1 |
| 17 | 2-amino-N-((R)-1-((R)-3a-benzyl-2-methyl-3-oxo-3a,4,6,7-tetrahydro-2H-pyrazolo[4,3-c]pyridin-5(3H)-yl)-3-oxo-3-(pyridin-2-yloxy)propan-2-yl)-2-methyl-propanamide | 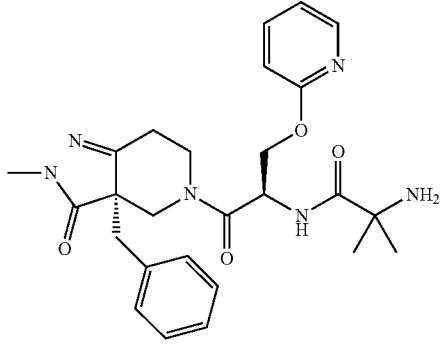 [SMILES: CNC(=O)[C@]1(Cc2ccccc2)CN(C(=O)[C@@H](COc2ccccn2)NC(=O)C(C)(C)N)CCC1=N] | 1.31 | 493.2 | (M + H)+ | A | QC1 |
| 18 | 2-amino-N-((R)-1-((R)-3a-benzyl-2-methyl-3-oxo-3a,4,6,7-tetrahydro-2H-pyrazolo[4,3-c]pyridin-5(3H)-yl)-3-((5-fluoropyridin-3-yl)oxy-1-oxopropan-2-yl)-2-methylpropanamide | 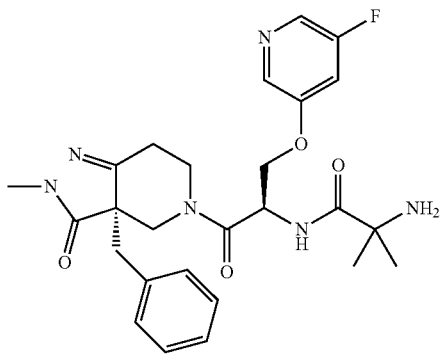 [SMILES: CNC(=O)[C@]1(Cc2ccccc2)CN(C(=O)[C@@H](COc2cncc(F)c2)NC(=O)C(C)(C)N)CCC1=N] | 1.26 | 511.2 | (M + H)+ | A | QC1 |

TABLE 5-continued

| Example | Name | Structure | tR (min) | m/z | Ion mode | Condition | Method |
|---|---|---|---|---|---|---|---|
| 19 | 2-amino-N-((R)-1-((R)-3a-benzyl-2-methyl-3-oxo-3a,4,6,7-tetrahydro-2H-pyrazolo[4,3-c]pyridin-5(3H)-yl)-1-oxo-3-((6-(trifluoromethyl)pyridin-2-yl)oxy)propan-2-yl)-2-methylpropanamide | 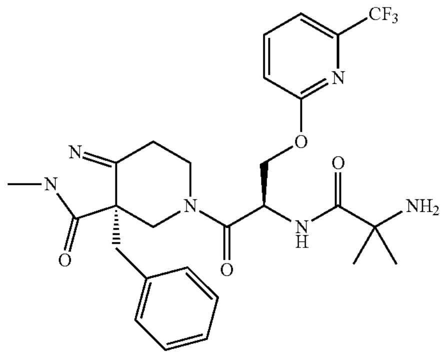 [SMILES: CNC(=O)[C@]1(Cc2ccccc2)CN(C(=O)[C@@H](COc2cccc(C(F)(F)F)n2)NC(=O)C(C)(C)N)CCC1=N] | 1.54 | 561.2 | (M + H)+ | A | QC1 |
| 20 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(4-cyanophenoxy)-1-oxo-propan-2-yl)-2-methyl-propanamide | 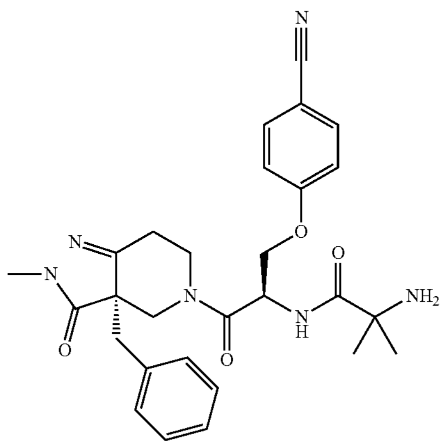 [SMILES: CNC(=O)[C@]1(Cc2ccccc2)CN(C(=O)[C@@H](COc2ccc(C#N)cc2)NC(=O)C(C)(C)N)CCC1=N] | 1.37 | 517.2 | (M + H)+ | A | QC1 |
| 21 | 2-amino-N-((R)-1-((R)-3a-benzyl-2-methyl-3-oxo-3a,4,6,7-tetrahydro-2H-pyrazolo[4,3-c]pyridin-5(3H)-yl)-1-oxo-3-phenoxypropan-2-yl)-2-methylpropanamide | 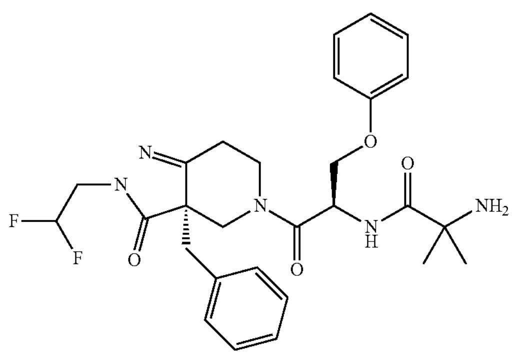 [SMILES: CC(C)(N)C(=O)N[C@H](COc1ccccc1)C(=O)N1CCC(=N)[C@](Cc2ccccc2)(C(=O)NCC(F)F)C1] | 1.54 | 542.3 | (M + H)+ | A | QC1 |
| 22 | 2-amino-N-((R)-1-((R)-3a-benzyl-2-methyl-3-oxo-3a,4,6,7-tetrahydro-2H-pyrazolo[4,3-c]pyridin-5(3H)-yl)-1-oxo-3-phenoxypropan-2-yl)-2-methylpropanamide | 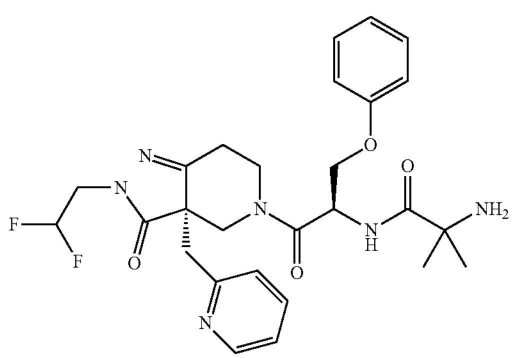 [SMILES: CC(C)(N)C(=O)N[C@H](COc1ccccc1)C(=O)N1CCC(=N)[C@](Cc2ccccn2)(C(=O)NCC(F)F)C1] | 1.38 | 541.2 | (M − H)− | A | QC1 |

TABLE 5-continued

| Example | Name | Structure | tR (min) | m/z | Ion mode | Condition | Method |
|---|---|---|---|---|---|---|---|
| 23 | 2-amino-N-((R)-3-(2-chlorophenoxy)-1-((R)-2-(2,2-difluoroethyl)-3-oxo-3a-(pyridin-2-yl-methyl)-3a,4,6,7-tetrahydro-2H-pyrazolo[4,3-c]pyridin-5(3H)-yl)-1-oxopropan-2-yl)-2-methylpropanamide | 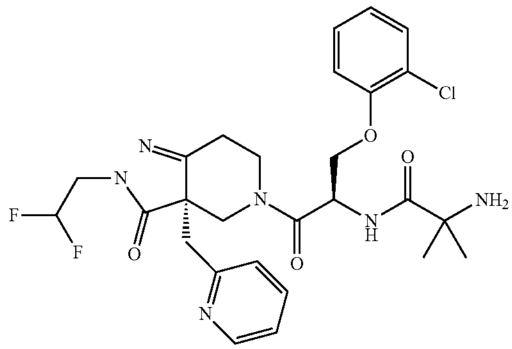 [SMILES: CC(C)(N)C(=O)N[C@H](COc1ccccc1Cl)C(=O)N1CCC(=N)[C@](Cc2ccccn2)(C(=O)NCC(F)F)C1] | 1.46 | 577 | (M + H)+ | A | QC1 |
| 24 | 2-amino-N-((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-3-(2-fluorophenoxy)-1-oxopropan-2-yl)-2-methylpropanamide | 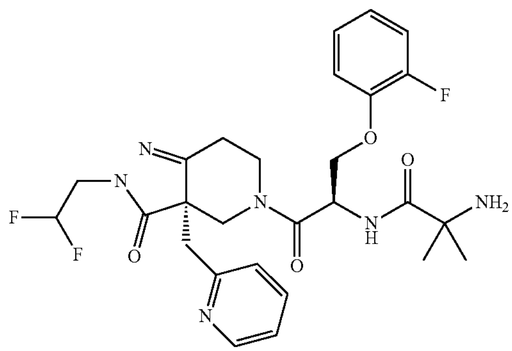 [SMILES: CC(C)(N)C(=O)N[C@H](COc1ccccc1F)C(=O)N1CCC(=N)[C@](Cc2ccccn2)(C(=O)NCC(F)F)C1] | 1.39 | 559.2 | (M − H)− | A | QC1 |
| 25 | 2-amino-N-((R)-3-(3-chlorophenoxy)-1-((R)-2-(2,2-difluoroethyl)-3-oxo-3a-(pyridin-2-yl-methyl)-3a,4,6,7-tetrahydro-2H-pyrazolo[4,3-c]pyridin-5(3H)-yl)-1-oxopropan-2-yl)-2-methylpropanamide | 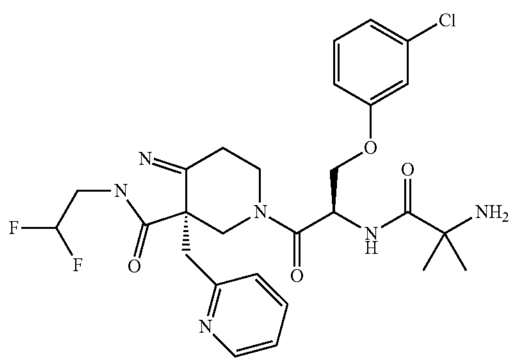 | 1.50 | 577 | (M + H)+ | A | QC1 |
| 26 | 2-amino-N-((R)-1-((R)-2-(2,2-difluoroethyl)-3-oxo-3a-(pyridin-2-yl-methyl)-3a,4,6,7-tetrahydro-2H-pyrazolo[4,3-c]pyridin-5(3H)-yl)-3-(3-methoxyphenoxy)-1-oxopropan-2-yl)-2-methylpropanamide | 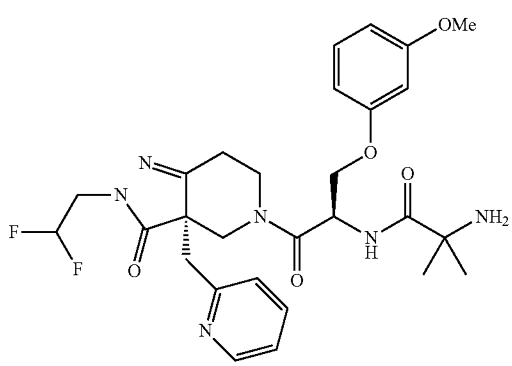 [SMILES: COc1cccc(OC[C@@H](NC(=O)C(C)(C)N)C(=O)N2CCC(=N)[C@](Cc3ccccn3)(C(=O)NCC(F)F)C2)c1] | 1.39 | 573.1 | (M + H)+ | A | QC1 |

TABLE 5-continued

| Example | Name | Structure | tR (min) | m/z | Ion mode | Condition | Method |
|---|---|---|---|---|---|---|---|
| 27 | 2-amino-N-((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-3-(3-fluorophenoxy)-1-oxo-propan-2-yl)-2-methylpropanamide | 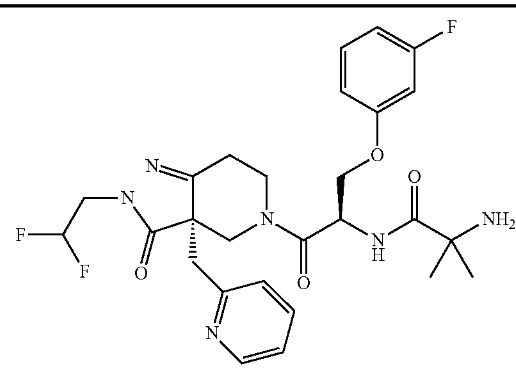 | 1.41 | 559.4 | (M − H)− | A | QC1 |
| 28 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(4-fluorophenoxy)-1-oxo-propan-2-yl)-2-methylpropanamide | 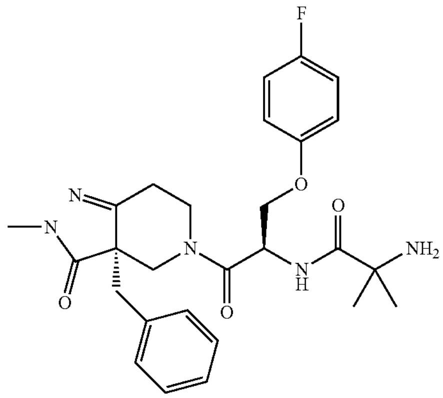 [SMILES: CNC(=O)[C@]1(Cc2ccccc2)CN(C(=O)[C@@H](COc2ccc(F)cc2)NC(=O)C(C)(C)N)CCC1=N] | 1.44 | 510.8 | (M + H)+ | A | QC1 |

Comparison Example 1

2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-4-phenoxybutan-2-yl)-2-methylpropanamide

Step 1: tert-butyl ((R)-1-((R)-3a-benzyl-2-methyl-3-oxo-3a,4,6,7-tetrahydro-2H-pyrazolo[4,3-c]pyridin-5(3H)-yl)-4-hydroxy-1-oxobutan-2-yl)carbamate A suspension of (R)-3a-benzyl-2-methyl-4,5,6,7-tetrahydro-2H-pyrazolo[4,3-c]pyridin-3(3aH)-one (2R,3R)-2,3-dihydroxysuccinate (1500 mg, 3.81 mmol) in EtOAc (30 mL) was cooled to −50° C. under nitrogen atmosphere, and triethylamine (1.06 mL, 7.62 mmol) was added dropwise at same temperature to allow freebasing of (R)-3a-benzyl-2-methyl-4,5,6,7-tetrahydro-2H-pyrazolo[4,3-c]pyridin-3(3aH)-one (2R,3R)-2,3-dihydroxysuccinate and salt formation of triethylammonium tartrate. After the mixture was stirred for 15 min, additional amount of triethylamine (1.59 mL, 11.4 mmol) was added dropwise to the mixture and the mixture was stirred at −50° C. for 10 min. To the mixture were added triethylammonium (R)-2-((tert-butoxycarbonyl)amino)-4-hydroxybutanoate dissolved in EtOAc (20 mL) over a period of 15 min and 2,4,6-tripropyl-1,3,5,2,4,6-trioxatriphosphinane 2,4,6-trioxide (4.49 mL, 7.63 mmol, 1.7 M solution in EtOAc) over a period of 10 min. After the mixture was stirred for another 2 hrs at −50° C., the reaction was quenched by the addition of a saturated aqueous NaHCO3 solution (50 mL) at the same temperature. The mixture was warmed to room temperature, diluted with water (50 mL) and extracted with EtOAc (50 mL×3). The combined organic layers were washed with brine, and was dried over Na2SO4. After filtration, the filtrate was concentrated in vacuo. The residue was purified by column chromatography (silica gel, eluted with 5% MeOH in EtOAc) to give the title compound as a colorless solid (1170 mg, 69% yield).

MS (ESI) m/z: 445 (M+H)+.

Step 2: tert-butyl ((R)-1-((R)-3a-benzyl-2-methyl-3-oxo-3a,4,6,7-tetrahydro-2H-pyrazolo[4,3-c]pyridin-5(3H)-yl)-1-oxo-4-phenoxybutan-2-yl)carbamate To a solution of tert-butyl ((R)-1-((R)-3a-benzyl-2-methyl-3-oxo-3a,4,6,7-tetrahydro-2H-pyrazolo[4,3-c]pyridin-5(3H)-yl)-4-hydroxy-1-oxobutan-2-yl)carbamate (200 mg, 0.45 mmol), phenol (64 mg, 0.68 mmol) and triphenylphosphine (236 mg, 0.90 mmol) in THF (8 mL) was added a solution of bis(2-methoxyethyl) azodicarboxylate (211 mg, 0.90 mmol) in THF (1 mL) dropwise at 0° C. After stirring at room temperature overnight, the mixture was diluted with water and extracted with EtOAc. The extract was washed with a saturated aqueous NaHCO3 solution and brine, and was dried over Na2SO4. After filtration, the filtrate was concentrated in vacuo. The residue was purified by column chromatography (silica gel, 15% to 50% EtOAc in hexane) to give the title compound (194 mg, 83% yield) as a white solid.

MS (ESI) m/z: 521 (M+H)+.

Step 3

(R)-5-((R)-2-amino-4-phenoxybutanoyl)-3a-benzyl-2-methyl-4,5,6,7-tetrahydro-2H-pyrazolo[4,3-c]pyridin-3 (3 aH)-one To a solution of tert-butyl ((R)-1-((R)-3a-benzyl-2-methyl-3-oxo-3a,4,6,7-tetrahydro-2H-pyrazolo[4,3-c]pyridin-5 (3H)-yl)-1-oxo-4-phenoxybutan-2-yl)carbamate (194 mg, 0.37 mmol) in DCM (5 mL) was added trifluoroacetic acid (2 mL) at 0° C. and the mixture was stirred at the same temperature for 30 min. Then, the mixture was concentrated in vacuo, and the residue was diluted DCM and the mixture was washed with a saturated aqueous NaHCO$_3$ solution and then brine, and was dried over Na$_2$SO$_4$. After filtration, the filtrate was concentrated in vacuo. The residue was purified by column chromatography (silica gel, eluted with 10% to 50% EtOAc in hexane) to give the title compound as a colorless gum (104 mg, 67% yield).

MS (ESI) m/z: 421 (M+H)$^+$.

Step 4: tert-butyl

(1-(((R)-1-((R)-3a-benzyl-2-methyl-3-oxo-3a,4,6,7-tetrahydro-2H-pyrazolo[4,3-c]pyridin-5 (3H)-yl)-1-oxo-4-phenoxybutan-2-yl)amino)-2-methyl-1-oxopropan-2-yl)carbamate To a suspension of (R)-5-((R)-2-amino-4-phenoxybutanoyl)-3a-benzyl-2-methyl-4,5,6,7-tetrahydro-2H-pyrazolo[4,3-c]pyridin-3(3aH)-one (100 mg, 0.24 mmol), 2-((tert-butoxycarbonyl)amino)-2-methylpropanoic acid (73 mg, 0.36 mmol) and triethylamine (0.13 mL, 0.95 mmol) in DCM (6 mL) was added O-(benzotriazol-1-yl)-N,N,N',N'-tetramethyluronium hexafluorophosphate (HBTU, 48 mg, 0.36 mmol) at room temperature. After stirring at the same temperature overnight, the mixture was concentrated in vacuo. The residue was passed through a short column chromatography (silica-gel, eluted with 2% to 20% EtOAc in hexane) to give the title compound as a colorless solid (131 mg, 91% yield).

MS (ESI) m/z: 506 (M−Boc+H)$^+$.

Step 5

2-amino-N—((R)-1-((R)-3a-benzyl-2-methyl-3-oxo-3a,4,6,7-tetrahydro-2H-pyrazolo[4,3-c]pyridin-5 (3H)-yl)-1-oxo-4-phenoxybutan-2-yl)-2-methylpropanamide To a solution of tert-butyl (1-(((R)-1-((R)-3a-benzyl-2-methyl-3-oxo-3a,4,6,7-tetrahydro-2H-pyrazolo[4,3-c]pyridin-5(3H)-yl)-1-oxo-4-phenoxybutan-2-yl)amino)-2-methyl-1-oxopropan-2-yl)carbamate (130 mg, 0.22 mmol) in DCM (4 mL) was added trifluoroacetic acid (2 mL) at 0° C. After stirring for 2 hrs at the same temperature, the mixture was concentrated in vacuo. The residue was diluted with DCM and the mixture was washed with a saturated aqueous NaHCO$_3$ solution and brine, and was dried over Na$_2$SO$_4$. After filtration, the filtered solvent and volatiles were removed. The residue was purified by preparative LC-MS to give 9.4 mg (9% yield) of the title compound as a pale brown solid.

Condition for the preparative LC-MS and quality check (QC) method are shown in Table 6.

Comparison Example 2

2-amino-N—((R)-1-((R)-3a-benzyl-2-methyl-3-oxo-3a,4,6,7-tetrahydro-2H-pyrazolo[4,3-c]pyridin-5 (3H)-yl)-4-(3,4-difluorophenoxy)-1-oxobutan-2-yl)-2-methylpropanamide

Step 1: tert-butyl

((R)-1-((R)-3a-benzyl-2-methyl-3-oxo-3a,4,6,7-tetrahydro-2H-pyrazolo[4,3-c]pyridin-5(3H)-yl)-4-(3,4-difluorophenoxy)-1-oxobutan-2-yl)carbamate The title compound was prepared in >99% yield (187 mg, oil) from tert-butyl ((R)-1-((R)-3a-benzyl-2-methyl-3-oxo-3a,4,6,7-tetrahydro-2H-pyrazolo[4,3-c]pyridin-5(3H)-yl)-4-hydroxy-1-oxobutan-2-yl)carbamate (150 mg, 0.34 mmol) and 3,4-difluorophenol (132 mg, 1.0 mmol) in a similar manner to Step 2 of Example 1.

MS (ESI) m/z: 557 (M+H)$^+$, 555 (M−H)$^-$.

Step 2

(R)-5-((R)-2-amino-4-(3,4-difluorophenoxy)butanoyl)-3a-benzyl-2-methyl-4,5,6,7-tetrahydro-2H-pyrazolo[4,3-c]pyridin-3(3aH)-one The title compound was prepared in 41% yield (62 mg, yellow solid) from tert-butyl ((R)-1-((R)-3a-benzyl-2-methyl-3-oxo-3a,4,6,7-tetrahydro-2H-pyrazolo[4,3-c]pyridin-5(3H)-yl)-4-(3,4-difluorophenoxy)-1-oxobutan-2-yl)carbamate (187 mg, 0.34 mmol) in a similar manner to Step 3 of Example 1.

MS (ESI) m/z: 457 (M+H)$^+$.

Step 3: tert-butyl

(1-(((R)-1-((R)-3a-benzyl-2-methyl-3-oxo-3a,4,6,7-tetrahydro-2H-pyrazolo[4,3-c]pyridin-5(3H)-yl)-4-(3,4-difluorophenoxy)-1-oxobutan-2-yl)amino)-2-methyl-1-oxopropan-2-yl)carbamate The title compound was prepared in >99% yield (84 mg, colorless solid) from (R)-5-((R)-2-amino-4-(3,4-difluorophenoxy)butanoyl)-3a-benzyl-2-methyl-4,5,6,7-tetrahydro-2H-pyrazolo[4,3-c]pyridin-3(3aH)-one (60 mg, 0.13 mmol) in a similar manner to Step 4 of Example 1.

MS (ESI) m/z: 542 (M−Boc+H)$^+$.

Step 4

2-amino-N—((R)-1-((R)-3a-benzyl-2-methyl-3-oxo-3a,4,6,7-tetrahydro-2H-pyrazolo[4,3-c]pyridin-5 (3H)-yl)-4-(3,4-difluorophenoxy)-1-oxobutan-2-yl)-2-methylpropanamide The title compound was prepared in 12% yield (9.3 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-4-(3,4-difluorophenoxy)-1-oxobutan-2-yl)amino)-2-methyl-1-oxopropan-2-yl)carbamate (84 mg, 0.13 mmol) in a similar manner to Step 5 of Example 1.

Comparison Example 3

2-amino-N—((R)-1-((R)-3a-benzyl-2-methyl-3-oxo-3a,4,6,7-tetrahydro-2H-pyrazolo[4,3-c]pyridin-5(3H)-yl)-4-(3,5-bis(trifluoromethyl)phenoxy)-1-oxobutan-2-yl)-2-methylpropanamide

Step 1: tert-butyl

((R)-1-((R)-3a-benzyl-2-methyl-3-oxo-3a,4,6,7-tetrahydro-2H-pyrazolo[4,3-c]pyridin-5(3H)-yl)-4-(3,5-bis(trifluoromethyl)phenoxy)-1-oxobutan-2-yl)carbamate The title compound was prepared in 45% yield (213 mg, white solid) from tert-butyl ((R)-1-((R)-3a-benzyl-2-methyl-3-oxo-3a,4,6,7-tetrahydro-2H-pyrazolo[4,3-c]pyridin-5(3H)-yl)-4-hydroxy-1-oxobutan-2-yl)carbamate (130 mg, 0.29 mmol) and 3,5-bis(trifluoromethyl)phenol (202 mg, 0.88 mmol) in a similar manner to Step 2 of Example 1.

MS (ESI) m/z: 601 (M-tBu+H)$^+$.

Step 2

(R)-5-((R)-2-amino-4-(3,5-bis(trifluoromethyl)phenoxy)butanoyl)-3a-benzyl-2-methyl-4,5,6,7-tetrahydro-2H-pyrazolo[4,3-c]pyridin-3(3aH)-one The title compound was prepared in 62% yield (50 mg, brown solid) from tert-butyl ((R)-1-((R)-3a-benzyl-2-methyl-3-oxo-3a,4,6,7-tetrahydro-2H-pyrazolo[4,3-c]pyridin-5(3H)-yl)-4-(3,5-bis(trifluoromethyl)phenoxy)-1-oxobutan-2-yl)carbamate (213 mg, 0.15 mmol) in a similar manner to Step 3 of Example 1.

MS (ESI) m/z: 557 (M+H)$^+$.

Step 3: tert-butyl

(1-(((R)-1-((R)-3a-benzyl-2-methyl-3-oxo-3a,4,6,7-tetrahydro-2H-pyrazolo[4,3-c]pyridin-5(3H)-yl)-4-(3,5-bis(trifluoromethyl)phenoxy)-1-oxobutan-2-yl)amino)-2-methyl-1-oxopropan-2-yl)carbamate The title compound was prepared in >99% yield (67 mg, white solid) from (R)-5-((R)-2-amino-4-(3,5-bis(trifluoromethyl)phenoxy)butanoyl)-3a-benzyl-2-methyl-4,5,6,7-tetrahydro-2H-pyrazolo[4,3-c]pyridin-3(3aH)-one (50 mg, 0.090 mmol) in a similar manner to Step 4 of Example 1.

MS (ESI) m/z: 742 (M+H)$^+$.

Step 4

2-amino-N—((R)-1-((R)-3a-benzyl-2-methyl-3-oxo-3a,4,6,7-tetrahydro-2H-pyrazolo[4,3-c]pyridin-5(3H)-yl)-4-(3,5-bis(trifluoromethyl)phenoxy)-1-oxobutan-2-yl)-2-methylpropanamide The title compound was prepared in 23% yield (12 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-4-(3,5-bis(trifluoromethyl)phenoxy)-1-oxobutan-2-yl)amino)-2-methyl-1-oxopropan-2-yl)carbamate (59 mg, 0.080 mmol) in a similar manner to Step 5 of Example 1.

Comparison Example 4

2-amino-N—((R)-1-((R)-3a-benzyl-2-methyl-3-oxo-3a,4,6,7-tetrahydro-2H-pyrazolo[4,3-c]pyridin-5(3H)-yl)-4-(4-fluorophenoxy)-1-oxobutan-2-yl)-2-methylpropanamide

Step 1: tert-butyl

((R)-1-((R)-3a-benzyl-2-methyl-3-oxo-3a,4,6,7-tetrahydro-2H-pyrazolo[4,3-c]pyridin-5(3H)-yl)-4-(4-fluorophenoxy)-1-oxobutan-2-yl)carbamate The title compound was prepared in 45% yield (213 mg, white solid) from tert-butyl ((R)-1-((R)-3a-benzyl-2-methyl-3-oxo-3a,4,6,7-tetrahydro-2H-pyrazolo[4,3-c]pyridin-5(3H)-yl)-4-hydroxy-1-oxobutan-2-yl)carbamate (60 mg, 0.14 mmol) and 4-fluorophenol (30 mg, 0.27 mmol) in a similar manner to Step 2 of Example 1.

MS (ESI) m/z: 601 (M−$^t$Bu+H)$^+$.

Step 2

(R)-5-((R)-2-amino-4-(4-fluorophenoxy)butanoyl)-3a-benzyl-2-methyl-4,5,6,7-tetrahydro-2H-pyrazolo[4,3-c]pyridin-3(3aH)-one The title compound was prepared in 13% yield (24 mg, brown gum) from tert-butyl ((R)-1-((R)-3a-benzyl-2-methyl-3-oxo-3a,4,6,7-tetrahydro-2H-pyrazolo[4,3-c]pyridin-5(3H)-yl)-4-(4-fluorophenoxy)-1-oxobutan-2-yl)carbamate (191 mg, 0.43 mmol) in a similar manner to Step 3 of Example 1.

MS (ESI) m/z: 439 (M+H)$^+$.

Step 3: tert-butyl

(1-(((R)-1-((R)-3a-benzyl-2-methyl-3-oxo-3a,4,6,7-tetrahydro-2H-pyrazolo[4,3-c]pyridin-5(3H)-yl)-4-(4-fluorophenoxy)-1-oxobutan-2-yl)amino)-2-methyl-1-oxopropan-2-yl)carbamate The title compound was prepared in 82% yield (28 mg, colorless gum) from (R)-5-((R)-2-amino-4-(4-fluorophenoxy)butanoyl)-3a-benzyl-2-methyl-4,5,6,7-tetrahydro-2H-pyrazolo[4,3-c]pyridin-3(3aH)-one (24 mg, 0.055 mmol) in a similar manner to Step 4 of Example 1.

MS (ESI) m/z: 624 (M+H)$^+$, 622 (M−H)$^−$.

Step 4

2-amino-N—((R)-1-((R)-3a-benzyl-2-methyl-3-oxo-3a,4,6,7-tetrahydro-2H-pyrazolo[4,3-c]pyridin-5(3H)-yl)-4-(4-fluorophenoxy)-1-oxobutan-2-yl)-2-methylpropanamide The title compound was prepared in 42% yield (9.8 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-4-(4-fluorophenoxy)-1-oxobutan-2-yl)amino)-2-methyl-1-oxopropan-2-yl)carbamate (28 mg, 0.045 mmol) in a similar manner to Step 5 of Example 1.

Comparison Example 5

2-amino-N—((R)-1-((R)-3a-benzyl-2-methyl-3-oxo-3a,4,6,7-tetrahydro-2H-pyrazolo[4,3-c]pyridin-5(3H)-yl)-4-((5-fluoropyridin-3-yl)oxy)-1-oxobutan-2-yl)-2-methylpropanamide

Step 1: tert-butyl ((R)-1-((R)-3a-benzyl-2-methyl-3-oxo-3a,4,6,7-tetrahydro-2H-pyrazolo[4,3-c]pyridin-5(3H)-yl)-4-((5-fluoropyridin-3-yl)oxy)-1-oxobutan-2-yl)carbamate The title compound was prepared in >99% yield (182 mg, pale brown gum) from tert-butyl ((R)-1-((R)-3a-benzyl-2-methyl-3-oxo-3a,4,6,7-tetrahydro-2H-pyrazolo[4,3-c]pyridin-5(3H)-yl)-4-hydroxy-1-oxobutan-2-yl)carbamate (150 mg, 0.34 mmol) and 5-fluoropyridine-3-ol (57 mg, 0.51 mmol) in a similar manner to Step 2 of Example 1.

MS (ESI) m/z: 540 (M+H)$^+$.

Step 2

(R)-5-((R)-2-amino-4-((5-fluoropyridin-3-yl)oxy)butanoyl)-3a-benzyl-2-methyl-4,5,6,7-tetrahydro-2H-pyrazolo[4,3-c]pyridin-3(3aH)-one The title compound was prepared in 21% yield (32 mg, pale brown solid) from tert-butyl ((R)-1-((R)-3a-benzyl-2-methyl-3-oxo-3a,4,6,7-tetrahydro-2H-pyrazolo[4,3-c]pyridin-5(3H)-yl)-4-((5-fluoropyridin-3-yl)oxy)-1-oxobutan-2-yl)carbamate (182 mg, 0.34 mmol) in a similar manner to Step 3 of Example 1.

MS (ESI) m/z: 440 (M+H)$^+$.

Step 3: tert-butyl (1-(((R)-1-((R)-3a-benzyl-2-methyl-3-oxo-3a,4,6,7-tetrahydro-2H-pyrazolo[4,3-c]pyridin-5(3H)-yl)-4-((5-fluoropyridin-3-yl)oxy)-1-oxobutan-2-yl)amino)-2-methyl-1-oxopropan-2-yl)carbamate The title compound was prepared in 89% yield (38 mg, pale brown solid) from (R)-5-((R)-2-amino-4-((5-fluoropyridin-3-yl)oxy)butanoyl)-3a-benzyl-2-methyl-4,5,6,7-tetrahydro-2H-pyrazolo[4,3-c]pyridin-3(3aH)-one (30 mg, 0.068 mmol) in a similar manner to Step 4 of Example 1.

MS (ESI) m/z: 625 (M+H)$^+$, 623 (M−H)$^-$.

Step 4

2-amino-N—((R)-1-((R)-3a-benzyl-2-methyl-3-oxo-3a,4,6,7-tetrahydro-2H-pyrazolo[4,3-c]pyridin-5(3H)-yl)-4-((5-fluoropyridin-3-yl)oxy)-1-oxobutan-2-yl)-2-methylpropanamide The title compound was prepared in 32% yield (9.7 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-4-((5-fluoropyridin-3-yl)oxy)-1-oxobutan-2-yl)amino)-2-methyl-1-oxopropan-2-yl)carbamate (38 mg, 0.061 mmol) in a similar manner to Step 5 of Example 1.

Comparison Example 6

2-amino-N—((R)-1-((R)-3a-benzyl-2-methyl-3-oxo-3a,4,6,7-tetrahydro-2H-pyrazolo[4,3-c]pyridin-5(3H)-yl)-4-(3-cyanophenoxy)-1-oxobutan-2-yl)-2-methylpropanamide

Step 1 tert-butyl((R)-1-((R)-3a-benzyl-2-methyl-3-oxo-3a,4,6,7-tetrahydro-2H-pyrazolo[4,3-c]pyridin-5(3H)-yl)-4-(3-cyanophenoxy)-1-oxobutan-2-yl)carbamate To a solution of tert-butyl ((R)-1-((R)-3a-benzyl-2-methyl-3-oxo-3a,4,6,7-tetrahydro-2H-pyrazolo[4,3-c]pyridin-5(3H)-yl)-4-hydroxy-1-oxobutan-2-yl)carbamate (150 mg, 0.34 mmol), 3-hydroxybenzonitrile (60 mg, 0.51 mmol), and tributylphosphine (0.17 mL, 0.38 mmol) in THF (2 mL) was added a solution of 1,1'-(azocarbonyl)-dipiperidine (170 mg, 0.65 mmol) in THF (4 mL) dropwise at 0° C. After stirring at room temperature for 3 days, the mixture was diluted with a saturated aqueous NaHCO$_3$ solution and EtOAc to separate. The organic layer was dried over Na$_2$SO$_4$. After filtration, the filtrate was concentrated in vacuo. The residue was purified by column chromatography (silica gel, 50% to 75% EtOAc in hexane) to give the title compound as a colorless gum (105 mg, 57% yield).

MS (ESI) m/z: 546 (M+H)$^+$, 544 (M−H)$^-$.

Step 2

3-((R)-3-amino-4-((R)-3a-benzyl-2-methyl-3-oxo-3a,4,6,7-tetrahydro-2H-pyrazolo[4,3-c]pyridin-5(3H)-yl)-4-oxobutoxy)benzonitrile The title compound was prepared in >99% yield (74 mg, pale brown oil) from butyl ((R)-1-((R)-3a-benzyl-2-methyl-3-oxo-3a,4,6,7-tetrahydro-2H-pyrazolo[4,3-c]pyridin-5(3H)-yl)-4-(3-cyanophenoxy)-1-oxobutan-2-yl)carbamate (91 mg, 0.17 mmol) in a similar manner to Step 3 of Example 1.

MS (ESI) m/z: 446 (M+H)$^+$.

Step 3: tert-butyl (1-(((R)-1-((R)-3a-benzyl-2-methyl-3-oxo-3a,4,6,7-tetrahydro-2H-pyrazolo[4,3-c]pyridin-5(3H)-yl)-4-(3-cyanophenoxy)-1-oxobutan-2-yl)amino)-2-methyl-1-oxopropan-2-yl)carbamate The title compound was prepared in >99% yield (105 mg, yellow gum) from 3-((R)-3-amino-4-((R)-3a-benzyl-2-methyl-3-oxo-3a,4,6,7-tetrahydro-2H-pyrazolo[4,3-c]pyridin-5(3H)-yl)-4-oxobutoxy)benzonitrile (74 mg, 0.17 mmol) in a similar manner to Step 4 of Example 1.

MS (ESI) m/z: 631 (M+H)$^+$, 629 (M−H)$^-$.

Step 4

2-amino-N—((R)-1-((R)-3a-benzyl-2-methyl-3-oxo-3a,4,6,7-tetrahydro-2H-pyrazolo[4,3-c]pyridin-5(3H)-yl)-4-(3-cyanophenoxy)-1-oxobutan-2-yl)-2-methylpropanamide The title compound was prepared in 19% yield (17 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-4-(3-cyanophenoxy)-1-oxobutan-2-yl)amino)-2-methyl-1-oxopropan-2-yl)carbamate (105 mg, 0.17 mmol) in a similar manner to Step 5 of Example 1.

TABLE 6

| Example | Name | Structure | tR (min) | m/z | Ion mode | Condition | Method |
|---|---|---|---|---|---|---|---|
| 1 | 2-amino-N-((R)-1-((R)-3a-benzyl-2-methyl-3-oxo-3a,4,6,7-tetrahydro-2H-pyrazolo[4,3-c]pyridin-5(3H)-yl)-1-oxo-4-phenoxybutan-2-yl)-2-methylpropanamide | 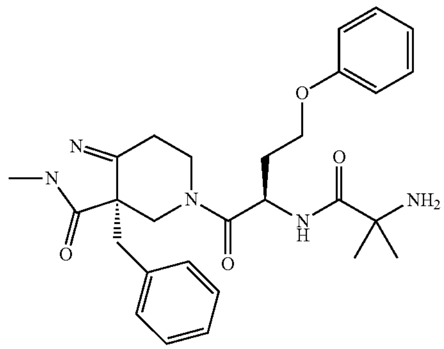 [SMILES: CNC(=O)[C@]1(Cc2ccccc2)CN(C(=O)[C@@H](CCOc2ccccc2)NC(=O)C(C)(C)N)CCC1=N] | 1.47 | 506.3 | (M + H)+ | A | QC1 |
| 2 | 2-amino-N-((R)-1-((R)-3a-benzyl-2-methyl-3-oxo-3a,4,6,7-tetrahydro-2H-pyrazolo[4,3-c]pyridin-5(3H)-yl)-4-(3,4-difluorophenoxy)-1-oxobutan-2-yl)-2-methylpropanamide | 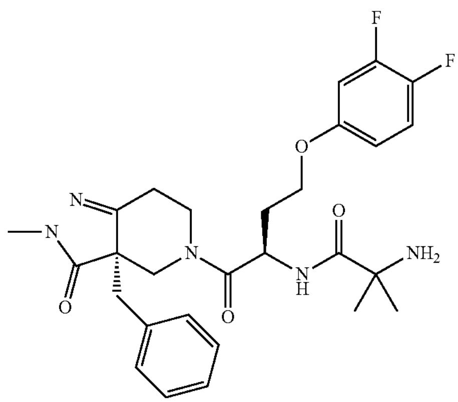 [SMILES: CNC(=O)[C@]1(Cc2ccccc2)CN(C(=O)[C@@H](CCOc2ccc(F)c(F)c2)NC(=O)C(C)(C)N)CCC1=N] | 1.54 | 542.2 | (M + H)+ | B | QC1 |
| 3 | 2-amino-N-((R)-1-((R)-3a-benzyl-2-methyl-3-oxo-3a,4,6,7-tetrahydro-2H-pyrazolo[4,3-c]pyridin-5(3H)-yl)-4-(3,5-bis(trifluoromethyl)phenoxy)-1-oxobutan-2-yl)-2-methylpropanamide | 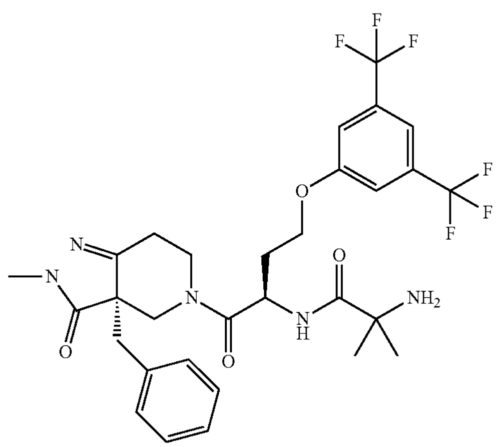 [SMILES: CNC(=O)[C@]1(Cc2ccccc2)CN(C(=O)[C@@H](CCOc2cc(C(F)(F)F)cc(C(F)(F)F)c2)NC(=O)C(C)(C)N)CCC1=N] | 1.80 | 642.3 | (M + H)+ | B | QC1 |
| 4 | 2-amino-N-((R)-1-((R)-3a-benzyl-2-methyl-3-oxo-3a,4,6,7-tetrahydro-2H-pyrazolo[4,3-c]pyridin-5(3H)-yl)-4-(4-fluorophenoxy)-1-oxobutan-2-yl)-2-methylpropanamide | 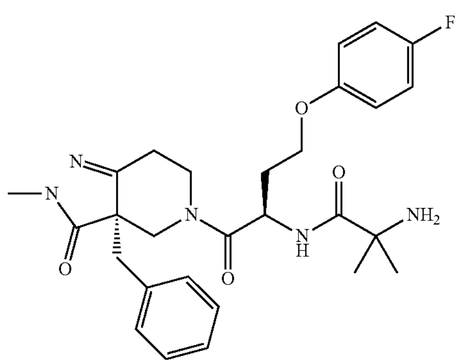 [SMILES: CNC(=O)[C@]1(Cc2ccccc2)CN(C(=O)[C@@H](CCOc2ccc(F)cc2)NC(=O)C(C)(C)N)CCC1=N] | 1.50 | 524.3 | (M + H)+ | B | QC1 |

TABLE 6-continued

| Example | Name | Structure | tR (min) | m/z | Ion mode | Condition | Method |
|---|---|---|---|---|---|---|---|
| 5 | 2-amino-N-((R)-1-((R)-3a-benzyl-2-methyl-3-oxo-3a,4,6,7-tetrahydro-2H-pyrazolo[4,3-c]pyridin-5(3H)-yl)-4-((5-fluoro-pyridin-3-yl)oxy)-1-oxobutan-2-yl)-2-methyl-propanamide | 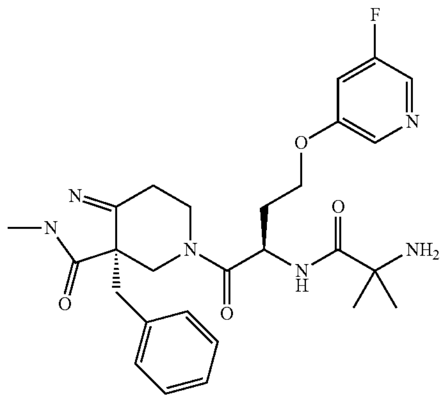 [SMILES: CNC(=O)[C@]1(Cc2ccccc2)CN(C(=O)[C@@H](CCOc2cncc(F)c2)NC(=O)C(C)(C)N)CCC1=N] | 1.28 | 523.3 | (M − H)⁻ | B | QC1 |
| 6 | 2-amino-N-((R)-1-((R)-3a-benzyl-2-methyl-3-oxo-3a,4,6,7-tetrahydro-2H-pyrazolo[4,3-c]pyridin-5(3H)-yl)-4-(3-cyano-phenoxy)-1-oxobutan-2-yl)-2-methylpropanamide | 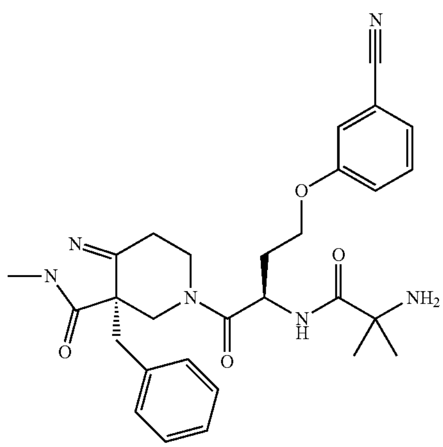 [SMILES: CNC(=O)[C@]1(Cc2ccccc2)CN(C(=O)[C@@H](CCOc2cccc(C#N)c2)NC(=O)C(C)(C)N)CCC1=N] | 1.43 | 528.4 | (M − H)⁻ | A | QC1 |

In Vitro Pharmacological Assays

Measurement of the Ghrelin Receptor Agonistic Activity Induced $Ca^{2+}$ Influx in HEK293 Cells Stably Expressing Human Ghrelin Receptor HEK293 cells stably expressing human ghrelin receptor were maintained in Dulbecco's modified Eagle medium (high glucose) supplemented with 10% fetal bovine serum, 100 units/ml penicillin, 100 microg/ml streptomycin and 500 microg/ml G418 at 37° C. in a humidified incubator with 5% $CO_2$ and grown to 60-80% confluence. The day before the assay, the cells were seeded on poly-D-lysine coated 384-well plates (BD FALCON) at a density of 10,000 cells per well, and incubated overnight in incubator.

On the day of the assay, the cells were washed three times with assay buffer (Hanks' balanced salt solution with 20 mM HEPES, pH7.4), and were incubated for 1 hour at room temperature to load 0.5 microM Fluo-4 AM reagent (Invitrogen).

After removing Fluo-4, and washing with assay buffer, the cells were added with various concentrations of the compounds. The changes in intracellular calcium concentration were monitored with the fluorescence imaging plate reader, FDSS6000 (Hamamatsu Photonics).

The $EC_{50}$ values for compounds of the present invention were determined from 11-point dose-response studies. Curves were generated using the average of duplicate wells for each data point. Finally, the $EC_{50}$ values were calculated using the best-fit dose curve determined by XLfit (ID Business Solutions Ltd).

All tested compounds show less than about 500 nanoM of $EC_{50}$ in the above assays. Preferable compounds show less than about 50 nanoM of $EC_{50}$ in the above assays.

More preferable compounds show less than about 10 nanoM of $EC_{50}$ in the above assays.

Preferable compounds are:

Examples 1-8, 10-14, 16, and 21-27.

More preferable compounds are:

Examples 9, 17, 18, and 20.

TABLE 7

Ratio of hGhrelin EC$_{50}$ between serine derivative and homoserine derivative

| serine derivative | homoserine derivative | ratio of hGhrelin EC50 (homoserine deriv./serine deriv.) |
|---|---|---|
| Example 2 | Comparison Example 1 | 10.5 |
| Example 7 | Comparison Example 2 | 10.6 |
| Example 9 | Comparison Example 3 | 8.7 |

TABLE 7-continued

Ratio of hGhrelin EC₅₀ between serine derivative and homoserine derivative

| serine derivative | homoserine derivative | ratio of hGhrelin EC50 (homoserine deriv./serine deriv.) |
|---|---|---|
| Example 28 | Comparison Example 4 | 25.9 |
| Example 16 | Comparison Example 5 | 9.1 |
| Example 18 | Comparison Example 6 | 12.6 |

In Vivo Pharmacological Assays

Growth Hormone (GH) Response in Conscious Mice

Female BALB/c mice (7 weeks old) were purchased from Charles River Japan and housed four or five animals per cage. After overnight fasting, test compounds were administered orally. Blood samples were collected at 5, 10, 30 minutes after drug administration. Two or three animals were used at each time point. Plasma concentration of mouse GH was measured using EIA kit (Rat Growth Hormone EIA KIT, SPI-Bio, France).

The compounds of the present invention show more than equal to 15 ng/ml of plasma concentration of mouse GH in the above assay.

In general, anesthetized rats have been used for investigating ghrelin compounds (Conventional method referred: Endocrinol Japan 31 (1984) 539-547, Journal of Endocrinology 171 (2001) 481-489, Gastroenterology 123 (2002) 1120-1128, Peptides 32 (2011)1001-1007). As the conventional assays require intravenous administration of the test compounds, they are not suitable for exploratory research of oral drugs. However the assay described above can be applied for oral administration in the fasted state, which is useful for evaluating growth hormone release of the test compounds in drug discovery. This is the first example of assay process for Growth hormone (GH) response in conscious fasting mice evaluating growth hormone release.

Effect on Cisplatin-Induced Cachexia/Anorexia in Rats

Male Wistar rats (7-8 weeks old) were purchased from Japan SLC, Inc. and housed individually in a room with controlled temperature and humidity under a 12-h light, 12-h dark cycle (lights on at 8 o'clock in the morning). Rats were adapted to the experimental environment for at least 5 days and handled twice. Food and water were given ad libitum. Rats were divided into two groups, namely sham controls and cisplatin-treated groups. From day 0 to day 2, cisplatin (0.6 mg/kg/day, Wako Pure Chemical) was administered intraperitoneally at the end of light phase. Sham rats were given saline only. Test compounds were administered orally for 3 days (from day 0 to day 2) immediately before the administration of cisplatin. To prevent cisplatin-induced nephrotoxicity, 2-3 mL of saline was injected subcutaneously immediately after saline or cisplatin administration. Body weight and food consumption were assessed daily from day 0 to day 4.

The statistically significant decrease of the body weight and food consumption in the rat treated with cisplatin is observed. Oral administration of compounds significantly increased body weight and food intake in the cisplatin-treated rats.

There are some reports that ghrelin shows an effect on reducing food intake in the short period (Conventional method referred: Endocrinology 149 (2008) 455-460, Endocrinology 151 (2010) 3773-3782, Neurogastroenterol Motil 25 (2013) 373-e292, Peptides 46 (2013) 13-19, Vitamins and Hormones 92 (2013) 301-317). There is no report that ghrelin agonists show the suppression of sustainable weight loss, and suppression of reducing food intake as much as 5 days study. When the conventional assay methods were applied for as much as 5 days, they resulted in failure because of cisplatin-induced nephrotoxicity in rats. Great efforts have made on working out the issue. Finally changing condition: 1) administration in the evening, 2) using well-handled rat adapted to the experimental environment for at least 5 days and handled at least twice and 3) saline loading, surprisingly, leads to successful results, which is useful for evaluating cachexia/anorexia in drug discovery. This is the first example of assay process for cisplatin-induced cachexia/anorexia in rats.

Effect on Cachexia in Rats Bearing the AH-130 Cells

Male Wistar rats (4 weeks old) were purchased from Japan SLC, Inc. and housed individually in a room with controlled temperature and humidity under a 12-h light, 12-h dark cycle (lights on at 8 o'clock in the morning). Rats were adapted to the experimental environment for at least 5 days and handled twice. Food and water were given ad libitum. Rats were divided into two groups, namely sham controls and tumor bearers. The latter was injected intraperitoneally with more than $1 \times 10^8$ AH-130 ascites hepatoma cells (Tohoku University, Sendai, Japan) on day 0. Sham rats were given PBS only. Tumor bearers group was further divided into treated and untreated, the former being administered test compounds orally for 9 days (from day 0 to day 8) at the end of light phase. Body weight was measured twice a week. At the end of the experiment, rats were sacrificed with $CO_2$ and greater pectoral muscle tissue was dissected and weighted.

Body weight is markedly reduced 5 days after inoculation of AH-130 ascites hepatoma cells compared with sham group. In rats administered compounds of the present invention, body weight and greater pectoral muscle weight at day 9 is significantly greater compared with control group.

There are no reports that ghrelin agonists suppress the sustainable weight loss. Great efforts have made on working out the issue. Finally changing condition: 1) using immature rats instead of mature rats, 2) increase of the cell number (more than $1 \times 10^8$ AH-130 ascites hepatoma cells) and 3) administration in the evening, surprisingly, leads to successful results. The assay process above is useful for evaluating cachexia in drug discovery. This is the first successful example of assay process for cachexia (weight loss and muscle wasting) in rats bearing the AH-130 cells.

The invention claimed is:
1. A compound of the following formula (I):

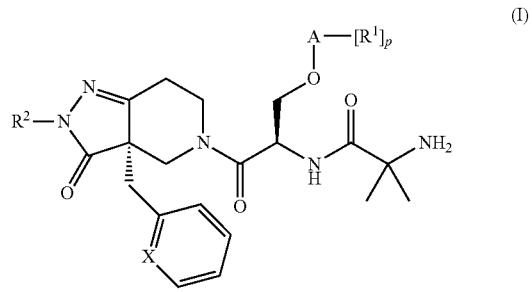

wherein:
A is aryl;
X is CH or N;
$R^1$ is independently selected from the group consisting of (1) hydrogen, (2) halogen, (3) $C_{1-6}$ alkyl, where the alkyl is unsubstituted or substituted with one or more substituents independently selected from the group consisting of halogen, hydroxy, —O—$C_{1-6}$ alkyl, amino, $C_{1-6}$ alkylamino, and ($C_{1-6}$ alkyl)($C_{1-6}$ alkyl)N—, (4) —O—$C_{1-6}$ alkyl, where the alkyl is unsubstituted or substituted with one or more substituents independently selected from the group consisting of halogen, hydroxy, —O—$C_{1-6}$ alkyl, amino, $C_{1-6}$ alkylamino, and ($C_{1-6}$ alkyl)($C_{1-6}$ alkyl)N—, (5) —CN and (6) —$SO_2C_{1-6}$ alkyl;
$R^2$ is hydrogen or $C_{1-6}$ alkyl, where the alkyl is unsubstituted or substituted with one or more substituents independently selected from the group consisting of halogen, hydroxy, —O—$C_{1-6}$ alkyl, amino, $C_{1-6}$ alkylamino, and ($C_{1-6}$ alkyl)($C_{1-6}$ alkyl)N—;
p is 1, 2, 3, or 4; and when p is two or more than two, $R^1$ may be the same or different;
or a pharmaceutically acceptable salt thereof.
2. The compound according to claim 1,
wherein:
A is phenyl, naphtyl, or pyridyl;
or a pharmaceutically acceptable salt thereof.

3. The compound according to claim 1,
wherein:
A is phenyl, naphtyl, or pyridyl;
R² is hydrogen or C₁-C₆ alkyl, where the alkyl is unsubstituted or substituted with one to three substituents independently selected from halogen;
or a pharmaceutically acceptable salt thereof.

4. The compound according to claim 1,
wherein:
A is phenyl, naphtyl, or pyridyl;
R¹ is independently selected from the group consisting of (1) hydrogen, (2) halogen, (3) trifluoromethyl, (4) trifluoromethoxy, (5) —CN and (6) —SO₂C₁₋₆ alkyl;
R² is C₁₋₆ alkyl, where the alkyl is unsubstituted or substituted with one to three substituents independently selected from halogen;
or a pharmaceutically acceptable salt thereof.

5. The compound according to claim 1,
wherein:
A is phenyl, naphtyl, or pyridyl;
R¹ is independently selected from the group consisting of;
(1) hydrogen, (2) —F, (3) —Cl (4) trifluoromethyl, (5) trifluoromethoxy and (6) —CN;
R² is methyl or difluoroethyl;
or a pharmaceutically acceptable salt thereof.

6. The compound according to claim 1,
wherein:
A is phenyl, 2-pyridyl or 3-pyridyl;
R¹ is independently selected from the group consisting of (1) hydrogen, (2) —F, (3) —Cl (4) trifluoromethyl, (5) trifluoromethoxy and (6) —CN;
R² is methyl or 2,2-difluoroethyl;
or a pharmaceutically acceptable salt thereof.

7. The compound according to claim 1, which is selected from the group consisting of:
2-amino-N—((R)-1-((R)-3a-benzyl-2-methyl-3-oxo-3a,4,6,7-tetrahydro-2H-pyrazolo[4,3-c]pyridin-5(3H)-yl)-3-(2,4-difluorophenoxy)-1-oxopropan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5 (3H)-yl)-1-oxo-3-phenoxypropan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5(3H)-yl)-3-(4-chlorophenoxy)-1-oxopropan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5(3H)-yl)-3-(3-chlorophenoxy)-1-oxopropan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5(3H)-yl)-3-(3,5-dichlorophenoxy)-1-oxopropan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5 (3H)-yl)-1-oxo-3-(2-(trifluoromethyl)phenoxy)propan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5(3H)-yl)-3-(3,4-difluorophenoxy)-1-oxopropan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5(3H)-yl)-3-(2-chlorophenoxy)-1-oxopropan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5(3H)-yl)-3-(3,5-bis(trifluoromethyl)phenoxy)-1-oxopropan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5 (3H)-yl)-3-(3-fluorophenoxy)-1-oxopropan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5(3H)-yl)-3-(3-methoxyphenoxy)-1-oxopropan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5(3H)-yl)-3-(2-fluorophenoxy)-1-oxopropan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5(3H)-yl)-3-(naphthalen-2-yloxy)-1-oxopropan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5(3H)-yl)-3-(naphthalen-1-yloxy)-1-oxopropan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5 (3H)-yl)-3-((5-chloropyridin-3-yl)oxy)-1-oxopropan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5 (3H)-yl)-3-(3-cyanophenoxy)-1-oxopropan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5 (3H)-yl)-1-oxo-3-(pyridin-2-yloxy)propan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5 (3H)-yl)-3-((5-fluoropyridin-3-yl)oxy)-1-oxopropan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-3-((6-(trifluoromethyl)pyridin-2-yl)oxy)propan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5 (3H)-yl)-3-(4-cyanophenoxy)-1-oxopropan-2-yl)-2-methylpropanamide;
2-amino-N—((R)-1-((R)-3a-benzyl-2-(2,2-difluoroethyl)-3-oxo-3a,4,6,7-tetrahydro-2H-pyrazolo[4,3-c]pyridin-5 (3H)-yl)-1-oxo-3-phenoxypropan-2-yl)-2-methylpropanamide;
2-amino-N—((R)-1-((R)-2-(2,2-difluoroethyl)-3-oxo-3a-(pyridin-2-ylmethyl)-3a,4,6,7-tetrahydro-2H-pyrazolo[4,3-c]pyridin-5 (3H)-yl)-1-oxo-3-phenoxypropan-2-yl)-2-methylpropanamide;
2-amino-N—((R)-3-(2-chlorophenoxy)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-1-oxopropan-2-yl)-2-methylpropanamide;
2-amino-N—((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-3-(2-fluorophenoxy)-1-oxopropan-2-yl)-2-methylpropanamide;
2-amino-N—((R)-3-(3-chlorophenoxy)-1-((R)-2-(2,2-difluoroethyl)-3-oxo-3a-(pyridin-2-ylmethyl)-3a,4,6,7- tetrahydro-2H-pyrazolo[4,3-c]pyridin-5(3H)-yl)-1-oxopropan-2-yl)-2-methylpropanamide;

2-amino-N—((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-3-(3-methoxyphenoxy)-1-oxopropan-2-yl)-2-methylpropanamide;

2-amino-N—((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-3-(3-fluorophenoxy)-1-oxopropan-2-yl)-2-methylpropanamide; and 2-amino-N—((R)-1-((R)-3a-benzyl-2-methyl-3-oxo-3a,4,6,7-tetrahydro-2H-pyrazolo[4,3-c]pyridin-5(3H)-yl)-3-(4-fluorophenoxy)-1-oxopropan-2-yl)-2-methylpropanamide;

or a pharmaceutically acceptable salt thereof.

8. The compound according to claim 1, which is selected from the group consisting of:

2-amino-N—((R)-1-((R)-3a-benzyl-2-methyl-3-oxo-3a,4,6,7-tetrahydro-2H-pyrazolo[4,3-c]pyridin-5(3H)-yl)-3-(2,4-difluorophenoxy)-1-oxopropan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5 (3H)-yl)-1-oxo-3-phenoxypropan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-3-(3,4-difluorophenoxy)-1-oxopropan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5 (3H)-yl)-3-(3-fluorophenoxy)-1-oxopropan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-3-(3-methoxyphenoxy)-1-oxopropan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-3-(2-fluorophenoxy)-1-oxopropan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5 (3H)-yl)-3-(3-cyanophenoxy)-1-oxopropan-2-yl)-2-methylpropanamide;

2-amino-N—((R)-1-((R)-2-(2,2-difluoroethyl)-3-oxo-3a-(pyridin-2-ylmethyl)-3a,4,6,7-tetrahydro-2H-pyrazolo[4,3-c]pyridin-5 (3H)-yl)-1-oxo-3-phenoxypropan-2-yl)-2-methylpropanamide;

2-amino-N—((R)-3-(2-chlorophenoxy)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-1-oxopropan-2-yl)-2-methylpropanamide;

2-amino-N—((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-3-(2-fluorophenoxy)-1-oxopropan-2-yl)-2-methylpropanamide;

2-amino-N—((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-3-(3-methoxyphenoxy)-1-oxopropan-2-yl)-2-methylpropanamide;

2-amino-N—((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-3-(3-fluorophenoxy)-1-oxopropan-2-yl)-2-methylpropanamide; and 2-amino-N—((R)-1-((R)-3a-benzyl-2-methyl-3-oxo-3a,4,6,7-tetrahydro-2H-pyrazolo[4,3-c]pyridin-5(3H)-yl)-3-(4-fluorophenoxy)-1-oxopropan-2-yl)-2-methylpropanamide;

or a pharmaceutically acceptable salt thereof.

9. A pharmaceutical composition comprising a compound or a pharmaceutically acceptable salt thereof, according to claim 1, and a pharmaceutically acceptable carrier, diluent or excipient.

10. The pharmaceutical composition according to claim 9, further comprising another pharmacologically active agent.

11. A method of treating an animal or human suffering from a condition or disorder mediated by the ghrelin receptor, which comprises administering to the human or animal an effective amount of a compound according to claim 1 or a pharmaceutically acceptable salt thereof, wherein the condition or disorder is at least one selected from the group consisting of: cancer anorexia/cachexia, cachexia and anorexia by an anti-cancer drug, hyperalgesia by an anti-cancer drug, chronic obstructive pulmonary disease (COPD)/COPD cachexia, sarcopenia, an eating disorder, a neurological eating disorder, weight loss suppression, early postoperative recovery of a cancer patient, chronic respiratory tract infection, inflammation, inflammatory bowel disease (IBD), functional-dyspepsia (FD), constipation, diabetic gastroparesis and gastroparesis, heart failure, myocardial infarction, diabetic neuropathy, Parkinson's disease, multiple sclerosis, diagnosis and treatment of growth hormone deficiency, elderly quality of life (QOL) improvement, bowel movement disturbance of a spinal cord injury patient, postoperative ileus, and morphine induced ileus.

12. A process for preparing a pharmaceutical composition for the treatment of an animal or human suffering from a condition or disorder mediated by the ghrelin receptor, comprising mixing a compound according to claim 1 or a pharmaceutically acceptable salt thereof with a pharmaceutically acceptable carrier, diluent or excipient, wherein the condition or disorder is at least one selected from the group consisting of: cancer anorexia/cachexia, cachexia and anorexia by an anti-cancer drug, hyperalgesia by an anti-cancer drug, chronic obstructive pulmonary disease (COPD)/COPD cachexia, sarcopenia, an eating disorder, a neurological eating disorder, weight loss suppression, early postoperative recovery of a cancer patient, chronic respiratory tract infection, inflammation, inflammatory bowel disease (IBD), functional-dyspepsia (FD), constipation, diabetic gastroparesis and gastroparesis, heart failure, myocardial infarction, diabetic neuropathy, Parkinson's disease, multiple sclerosis, diagnosis and treatment of growth hormone deficiency, elderly quality of life (QOL) improvement, bowel movement disturbance of a spinal cord injury patient, postoperative ileus, and morphine induced ileus.

13. A process for detecting a Growth hormone (GH) response in a conscious fasting mouse comprising oral administering a compound according to claim 1, or a pharmaceutically acceptable salt thereof, to a BALB/c mouse and detecting the GH response in the mouse.

14. A process for detecting cisplatin-induced cachexia/anorexia in a rat comprising administering a compound according to claim 1, or a pharmaceutically acceptable salt thereof, and cisplatin in the evening to a well-handled rat and detecting the cisplatin-induced cachexia/anorexia in the rat.

15. A process for detecting cachexia (weight loss and muscle wasting) in a rat bearing AH-130 cells comprising oral administering a compound according to claim 1, or a pharmaceutically acceptable salt thereof, to an immature male rat injected intraperitoneally with more than 1×10⁸ AH-130 ascites hepatoma cells and detecting the cachexia in the rat.

16. The compound according to claim 1, which is selected from the group consisting of:
- 2-amino-N—((R)-1-((R)-3a-benzyl-2-methyl-3-oxo-3a,4,6,7-tetrahydro-2H-pyrazolo[4,3-c]pyridin-5 (3H)-yl)-1-oxo-3-phenoxypropan-2-yl)-2-methylpropanamide;
- 2-amino-N—((R)-1-((R)-3a-benzyl-2-methyl-3-oxo-3a,4,6,7-tetrahydro-2H-pyrazolo[4,3-c]pyridin-5(3H)-yl)-3-(3,4-difluorophenoxy)-1-oxopropan-2-yl)-2-methylpropanamide;
- 2-amino-N—((R)-1-((R)-3a-benzyl-2-methyl-3-oxo-3a,4,6,7-tetrahydro-2H-pyrazolo[4,3-c]pyridin-5 (3H)-yl)-3-(3-cyanophenoxy)-1-oxopropan-2-yl)-2-methylpropanamide; and
- 2-amino-N—((R)-1-((R)-3a-benzyl-2-methyl-3-oxo-3a,4,6,7-tetrahydro-2H-pyrazolo[4,3-c]pyridin-5(3H)-yl)-3-(4-fluorophenoxy)-1-oxopropan-2-yl)-2-methylpropanamide;

or a pharmaceutically acceptable salt thereof.

* * * * *

UNITED STATES PATENT AND TRADEMARK OFFICE
CERTIFICATE OF CORRECTION

PATENT NO. : 9,873,695 B2
APPLICATION NO. : 15/316543
DATED : January 23, 2018
INVENTOR(S) : Iwata et al.

Page 1 of 16

It is certified that error appears in the above-identified patent and that said Letters Patent is hereby corrected as shown below:

In the Specification

In Column 23, Line 2, " " should read

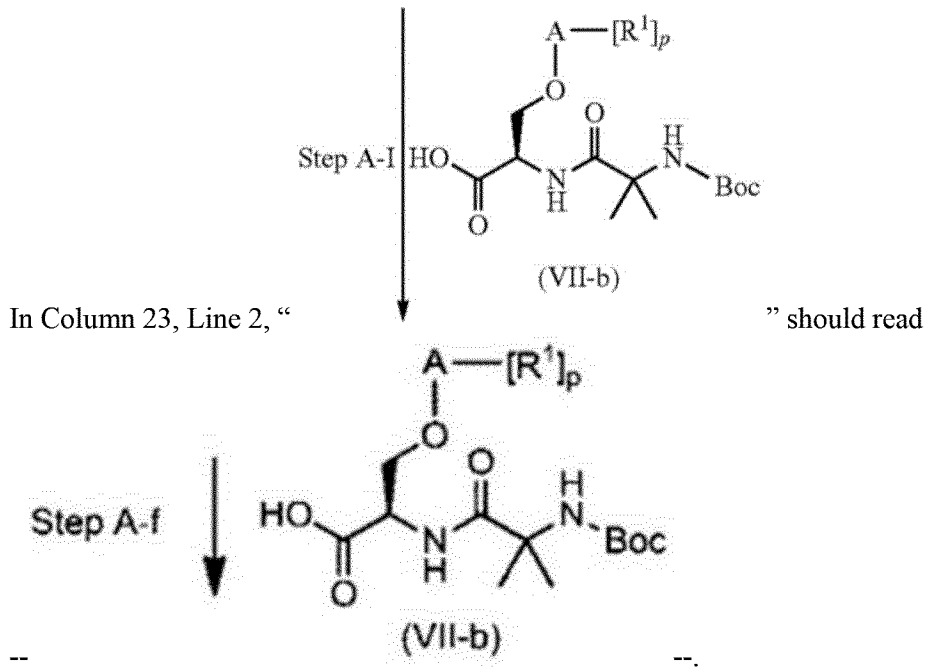

-- --.

Signed and Sealed this
Ninth Day of July, 2019

Andrei Iancu
*Director of the United States Patent and Trademark Office*

In Column 30, Lines 1-25, TABLE 3, "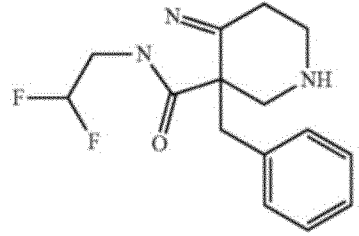"
TABLE 3
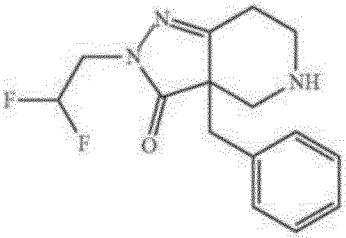
should read -- 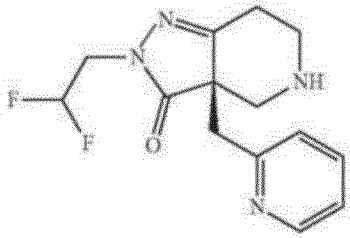 --.

In Column 77, Line 1 to Column 92, Line 35, Table 5,

| Example | Name | Structure | tR (min) | m/z | Ion mode | Condition | Method |
|---|---|---|---|---|---|---|---|
| 1 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(2,4-difluoro-phenoxy)-1-oxopropan-2-yl)-2-methylpropanamide | 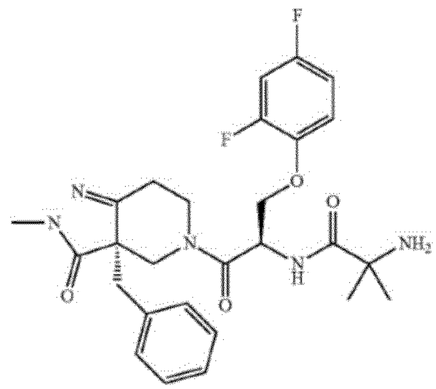 | 1.49 | 528.3 | (M + H)+ | A | QC1 |
| 2 | 2-amino-N-((R)-1-((R)-3a-benzyl-2-methyl-3-oxo-3a,4,6,7-tetrahydro-2H-pyrazolo[4,3-c]pyridin-5(3H)-yl)-1-oxo-3-phenoxypropan-2-yl)-2-methylpropanamide | 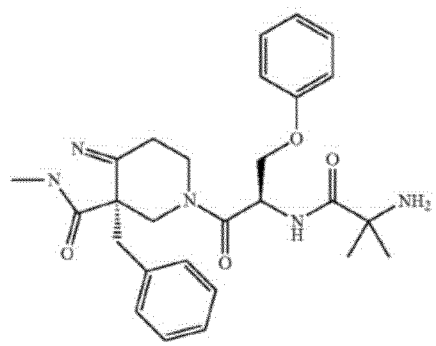 | 1.44 | 492.3 | (M + H)+ | A | QC1 |

"

| Example | Name | Structure | tR (min) | m/z | Ion mode | Condition | Meth |
|---|---|---|---|---|---|---|---|
| 3 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(4-chlorophenoxy)-1-oxo-propan-2-yl)-2-methyl-propanamide | 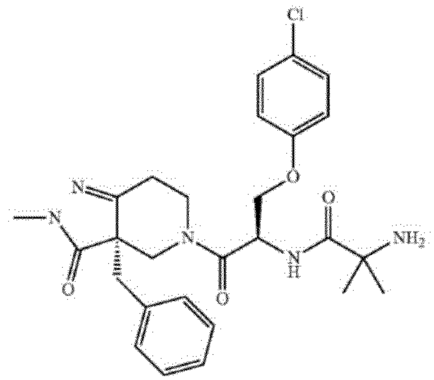 | 1.55 | 526.3 | (M + H)⁺ | A | QC |
| 4 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(3-chlorophenoxy)-1-oxo-propan-2-yl)-2-methyl-propanamide | 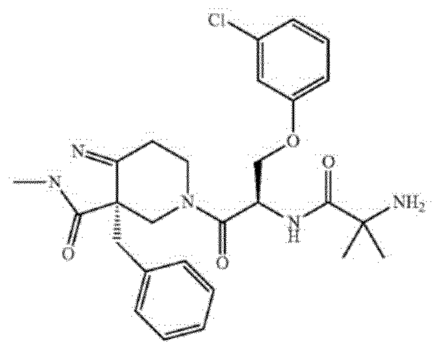 | 1.56 | 526.2 | (M + H)⁺ | A | QC |
| 5 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(3,5-dichlorophenoxy)-1-oxopropan-2-yl)-2-methylpropanamide | 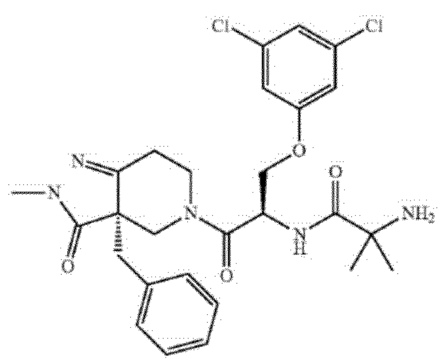 | 1.69 | 560.2 | (M + H)⁺ | A | QC1 |
| 6 | 2-amino-N-((R)-1-((R)-3a-benzyl-2-methyl-3-oxo-3a,4,6,7-tetrahydro-2H-pyrazolo[4,3-c]pyridin-5(3H)-yl)-1-oxo-3-(2-trifluoro-methyl)phenoxy)propan-2-yl)-2-methylpropanamide | 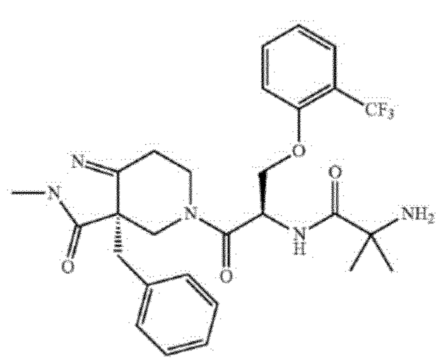 | 2.16 | 558.2 | (M − H) | A | QC2 |

| Example | Name | Structure | tR (min) | m/z | Ion mode | Condition | Method |
|---|---|---|---|---|---|---|---|
| 7 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(3,4-difluorophenoxy)-1-oxopropan-2-yl)-2-methylpropanamide | 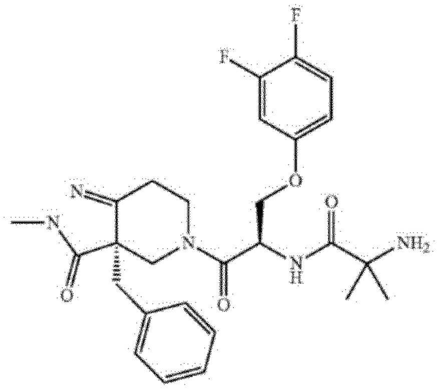 | 2.04 | 526.1 | (M − H)⁻ | A | QC2 |
| 8 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(2-chlorophenoxy)-1-oxopropan-2-yl)-2-methylpropanamide | 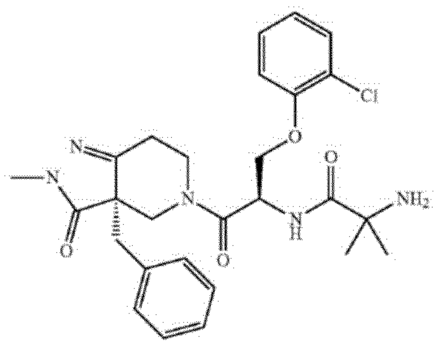 | 2.08 | 524.2 | (M − H)⁻ | A | QC2 |
| 9 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(3,5-bis(trifluoromethyl)phenoxy)-1-oxopropan-2-yl)-2-methylpropanamide | 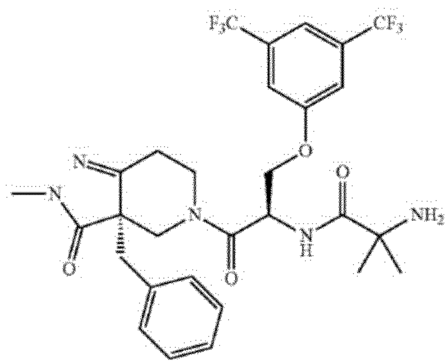 | 2.46 | 626.2 | (M − H)⁻ | A | QC2 |
| 10 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(3-fluorophenoxy)-1-oxopropan-2-yl)-2-methylpropanamide | 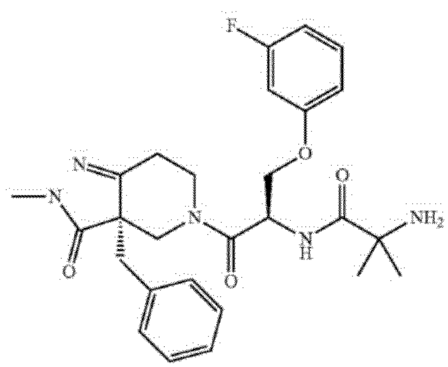 | 1.46 | 508.3 | (M + H)⁺ | A | QC1 |

| Example | Name | Structure | tR (min) | m/z | Ion mode | Condition | Method |
|---|---|---|---|---|---|---|---|
| 11 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(3-methoxyphenoxy)-1-oxopropan-2-yl)-2-methylpropanamide | 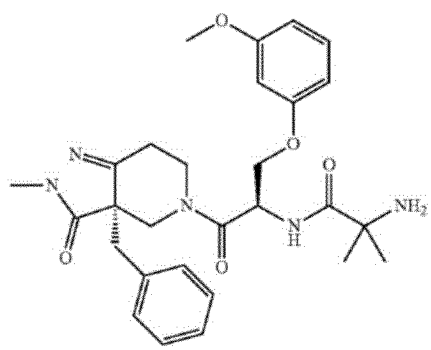 | 1.44 | 520.3 | (M − H)⁻ | A | QC1 |
| 12 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(2-fluorophenoxy)-1-oxopropan-2-yl)-2-methylpropanamide | 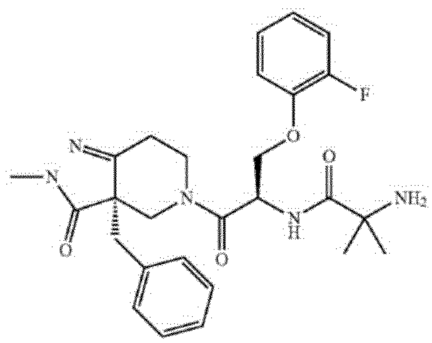 | 1.44 | 508.3 | (M − H)⁻ | A | QC1 |
| 13 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(naphthalen-2-yloxy)-1-oxopropan-2-yl)-2-methylpropanamide | 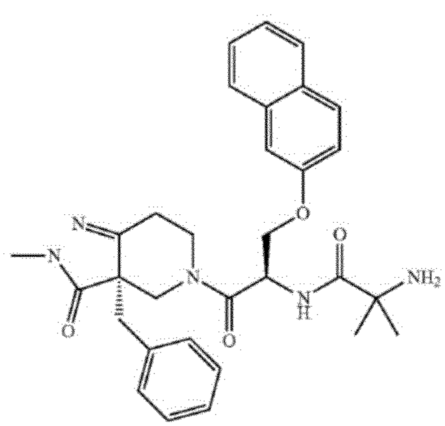 | 1.60 | 542.2 | (M + H)⁺ | A | QC1 |
| 14 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(naphthalen-1-yloxy)-1-oxopropan-2-yl)-2-methylpropanamide | 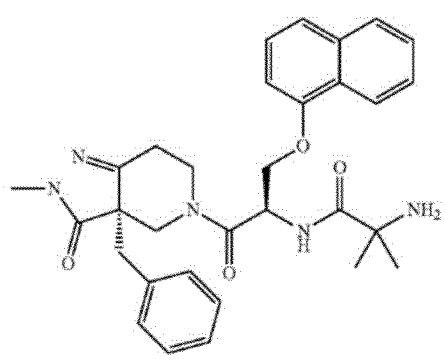 | 1.60 | 542.3 | (M + H)⁺ | A | QC1 |

| Example | Name | Structure | tR (min) | m/z | Ion mode | Condition | Method |
|---|---|---|---|---|---|---|---|
| 15 | 2-amino-N-((R)-1-((R)-3a-benzyl-2-methyl-3-oxo-3a,4,6,7-tetrahydro-2H-pyrazolo[4,3-c]pyridin-5(3H)-yl)-3-((5-chloropyridin-3-yl)oxy)-1-oxopropan-2-yl)-2-methylpropanamide | 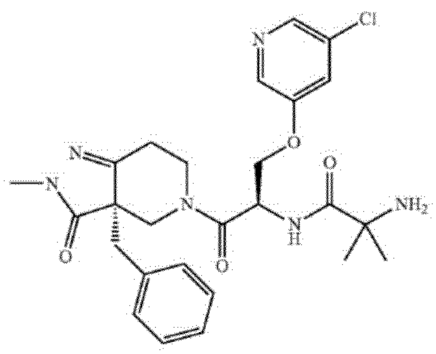 | 1.35 | 527.1 | (M + H)+ | A | QC1 |
| 16 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(3-cyanophenoxy)-1-oxo-propan-2-yl)-2-methyl-propanamide | 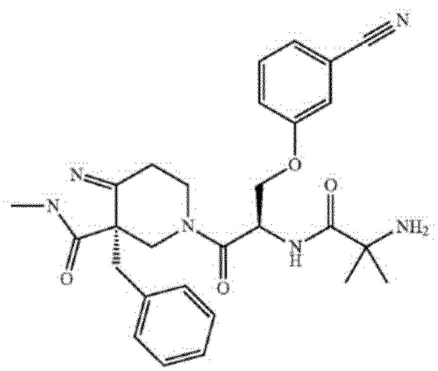 | 1.39 | 517.2 | (M + H)+ | A | QC1 |
| 17 | 2-amino-N-((R)-1-((R)-3a-benzyl-2-methyl-3-oxo-3a,4,6,7-tetrahydro-2H-pyrazolo[4,3-c]pyridin-5(3H)-yl)-3-oxo-3-(pyridin-2-yloxy)propan-2-yl)-2-methyl-propanamide | 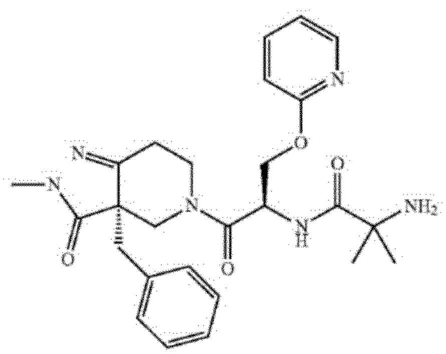 | 1.31 | 493.2 | (M + H)+ | A | QC1 |
| 18 | 2-amino-N-((R)-1-((R)-3a-benzyl-2-methyl-3-oxo-3a,4,6,7-tetrahydro-2H-pyrazolo[4,3-c]pyridin-5(3H)-yl)-3-((5-fluoropyridin-3-yl)oxy-1-oxopropan-2-yl)-2-methylpropanamide | 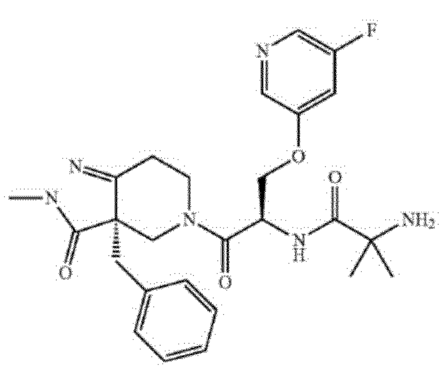 | 1.26 | 511.2 | (M + H)+ | A | QC1 |

| Example | Name | Structure | tR (min) | m/z | Ion mode | Condition | Method |
|---|---|---|---|---|---|---|---|
| 19 | 2-amino-N-((R)-1-((R)-3a-benzyl-2-methyl-3-oxo-3a,4,6,7-tetrahydro-2H-pyrazolo[4,3-c]pyridin-5(3H)-yl)-1-oxo-3-((6-(trifluoromethyl)pyridin-2-yl)oxy)propan-2-yl)-2-methylpropanamide | 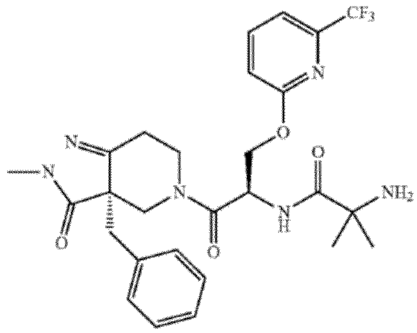 | 1.54 | 561.2 | (M + H)+ | A | QC1 |
| 20 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(4-cyanophenoxy)-1-oxopropan-2-yl)-2-methylpropanamide | 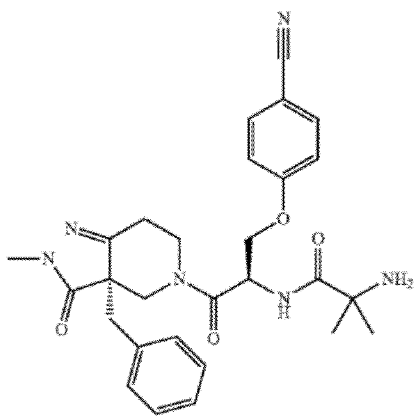 | 1.37 | 517.2 | (M + H)+ | A | QC1 |
| 21 | 2-amino-N-((R)-1-((R)-3a-benzyl-2-methyl-3-oxo-3a,4,6,7-tetrahydro-2H-pyrazolo[4,3-c]pyridin-5(3H)-yl)-1-oxo-3-phenoxypropan-2-yl)-2-methylpropanamide | 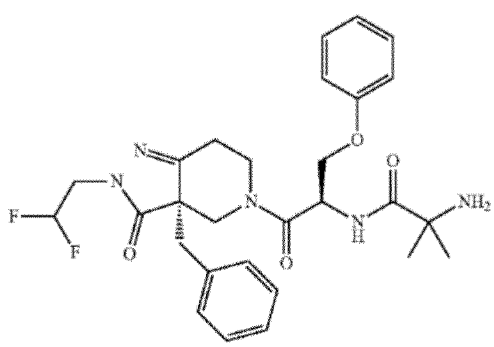 | 1.54 | 542.3 | (M + H)+ | A | QC1 |
| 22 | 2-amino-N-((R)-1-((R)-3a-benzyl-2-methyl-3-oxo-3a,4,6,7-tetrahydro-2H-pyrazolo[4,3-c]pyridin-5(3H)-yl)-1-oxo-3-phenoxypropan-2-yl)-2-methylpropanamide | 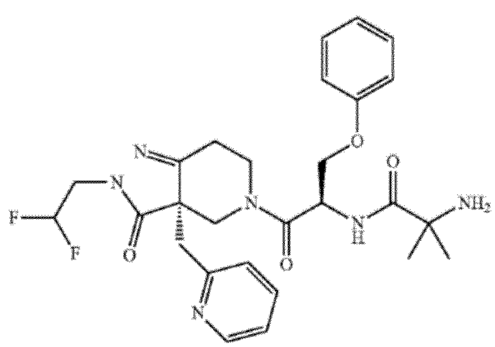 | 1.38 | 541.2 | (M − H)− | A | QC1 |

| Example | Name | Structure | tR (min) | m/z | Ion mode | Condition | Method |
|---|---|---|---|---|---|---|---|
| 23 | 2-amino-N-((R)-3-(2-chlorophenoxy)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-1-oxopropan-2-yl)-2-methylpropanamide | 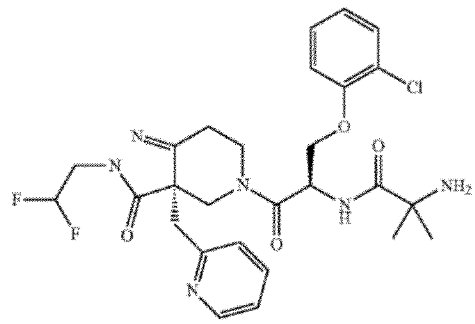 | 1.46 | 577 | (M + H)⁺ | A | QC1 |
| 24 | 2-amino-N-((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-3-(2-fluorophenoxy)-1-oxopropan-2-yl)-2-methylpropanamide | 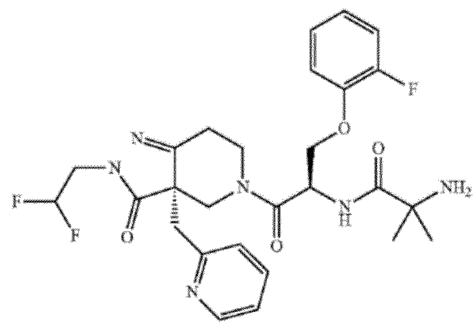 | 1.39 | 559.2 | (M − H)⁻ | A | QC1 |
| 25 | 2-amino-N-((R)-3-(3-chlorophenoxy)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-1-oxopropan-2-yl)-2-methylpropanamide | 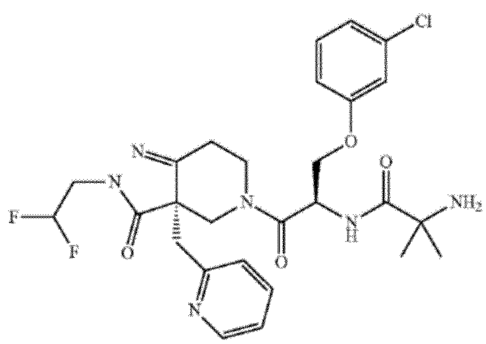 | 1.50 | 577 | (M + H)⁺ | A | QC1 |
| 26 | 2-amino-N-((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-3-(3-methoxyphenoxy)-1-oxopropan-2-yl)-2-methylpropanamide | 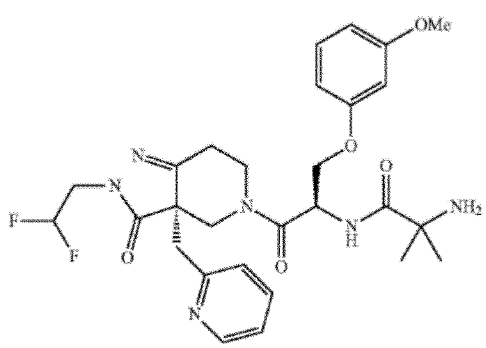 | 1.39 | 573.1 | (M + H)⁺ | A | QC1 |

CERTIFICATE OF CORRECTION (continued)
U.S. Pat. No. 9,873,695 B2

Page 10 of 16

| Example | Name | Structure | tR (min) | m/z | Ion mode | Condition | Method |
|---|---|---|---|---|---|---|---|
| 27 | 2-amino-N-((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-3-(3-fluorophenoxy)-1-oxopropan-2-yl)-2-methylpropanamide | 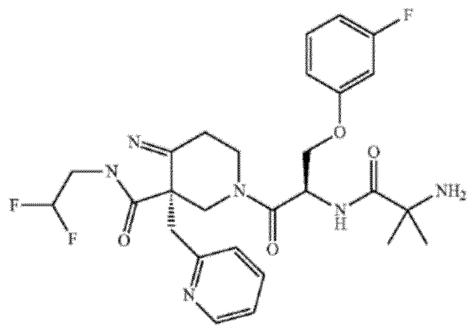 | 1.41 | 559.4 | (M − H)⁻ | A | QC1 |
| 28 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(4-fluorophenoxy)-1-oxopropan-2-yl)-2-methylpropanamide | 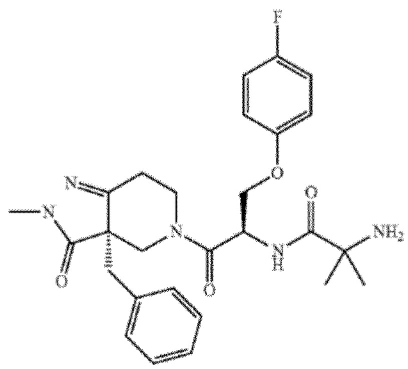 | 1.44 | 510.8 | (M + H)⁺ | A | QC1 |

"

should read

TABLE 5

| Example | Name | Structure | tR (min) | m/z | Ion mode | Condition | Method |
|---|---|---|---|---|---|---|---|
| 1 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(2,4-difluorophenoxy)-1-oxopropan-2-yl)-2-methylpropanamide | 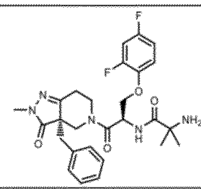 | 1.49 | 528.3 | (M+H)+ | A | QC1 |
| 2 | 2-amino-N-((R)-1-((R)-3a-benzyl-2-methyl-3-oxo-3a,4,6,7-tetrahydro-2H-pyrazolo[4,3-c]pyridin-5(3H)-yl)-1-oxo-3-phenoxypropan-2-yl)-2-methylpropanamide | 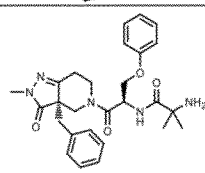 | 1.44 | 492.3 | (M+H)+ | A | QC1 |
| 3 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(4-chlorophenoxy)-1-oxopropan-2-yl)-2-methylpropanamide | 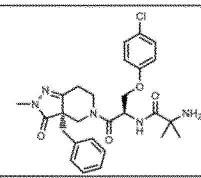 | 1.55 | 526.3 | (M+H)+ | A | QC1 |
| 4 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(3-chlorophenoxy)-1-oxopropan-2-yl)-2-methylpropanamide | 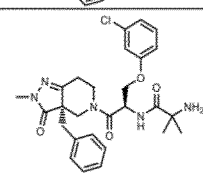 | 1.56 | 526.2 | (M+H)+ | A | QC1 |
| 5 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(3,5-dichlorophenoxy)-1-oxopropan-2-yl)-2-methylpropanamide | 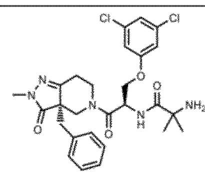 | 1.69 | 560.2 | (M+H)+ | A | QC1 |
| 6 | 2-amino-N-((R)-1-((R)-3a-benzyl-2-methyl-3-oxo-3a,4,6,7-tetrahydro-2H-pyrazolo[4,3-c]pyridin-5(3H)-yl)-1-oxo-3-(2-(trifluoromethyl)phenoxy)propan-2-yl)-2-methylpropanamide | 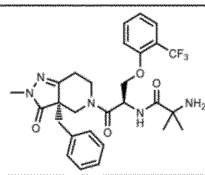 | 2.16 | 558.2 | (M-H)- | A | QC2 |
| 7 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(3,4-difluorophenoxy)-1-oxopropan-2-yl)-2-methylpropanamide | 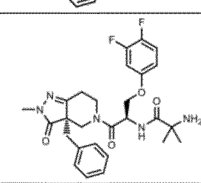 | 2.04 | 526.1 | (M-H)- | A | QC2 |
| 8 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(2-chlorophenoxy)-1-oxopropan-2-yl)-2-methylpropanamide | 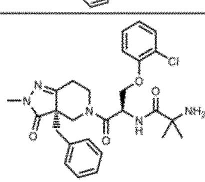 | 2.08 | 524.2 | (M-H)- | A | QC2 |
| 9 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(3,5-bis(trifluoromethyl)phenoxy)-1-oxopropan-2-yl)-2-methylpropanamide | 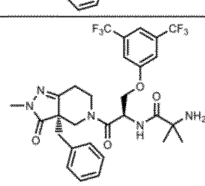 | 2.46 | 626.2 | (M-H)- | A | QC2 |

| # | Name | Structure | RT | MS | Ion | | |
|---|------|-----------|-----|------|-----|---|---|
| 10 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(3-fluorophenoxy)-1-oxopropan-2-yl)-2-methylpropanamide | | 1.46 | 508.3 | (M-H)⁻ | A | QC1 |
| 11 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(3-methoxyphenoxy)-1-oxopropan-2-yl)-2-methylpropanamide | | 1.44 | 520.3 | (M-H)⁻ | A | QC1 |
| 12 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(2-fluorophenoxy)-1-oxopropan-2-yl)-2-methylpropanamide | | 1.44 | 508.3 | (M-H)⁻ | A | QC1 |
| 13 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(naphthalen-2-yloxy)-1-oxopropan-2-yl)-2-methylpropanamide | | 1.60 | 542.2 | (M+H)⁺ | A | QC1 |
| 14 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(naphthalen-1-yloxy)-1-oxopropan-2-yl)-2-methylpropanamide | | 1.60 | 542.3 | (M+H)⁺ | A | QC1 |
| 15 | 2-amino-N-((R)-1-((R)-3a-benzyl-2-methyl-3-oxo-3a,4,6,7-tetrahydro-2H-pyrazolo[4,3-c]pyridin-5(3H)-yl)-3-((5-chloropyridin-3-yl)oxy)-1-oxopropan-2-yl)-2-methylpropanamide | | 1.35 | 527.1 | (M+H)⁺ | A | QC1 |
| 16 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(3-cyanophenoxy)-1-oxopropan-2-yl)-2-methylpropanamide | | 1.39 | 517.2 | (M+H)⁺ | A | QC1 |
| 17 | 2-amino-N-((R)-1-((R)-3a-benzyl-2-methyl-3-oxo-3a,4,6,7-tetrahydro-2H-pyrazolo[4,3-c]pyridin-5(3H)-yl)-1-oxo-3-(pyridin-2-yloxy)propan-2-yl)-2-methylpropanamide | | 1.31 | 493.2 | (M+H)⁺ | A | QC1 |
| 18 | 2-amino-N-((R)-1-((R)-3a-benzyl-2-methyl-3-oxo-3a,4,6,7-tetrahydro-2H-pyrazolo[4,3-c]pyridin-5(3H)-yl)-3-((5-fluoropyridin-3-yl)oxy)-1-oxopropan-2-yl)-2-methylpropanamide | | 1.26 | 511.2 | (M+H)⁺ | A | QC1 |

| # | Name | Structure | RT | MS | Ion | A | QC |
|---|---|---|---|---|---|---|---|
| 19 | 2-amino-N-((R)-1-((R)-3a-benzyl-2-methyl-3-oxo-3a,4,6,7-tetrahydro-2H-pyrazolo[4,3-c]pyridin-5(3H)-yl)-1-oxo-3-((6-(trifluoromethyl)pyridin-2-yl)oxy)propan-2-yl)-2-methylpropanamide | 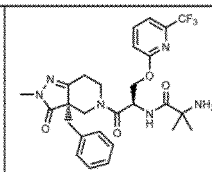 | 1.54 | 561.2 | (M+H)+ | A | QC1 |
| 20 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(4-cyanophenoxy)-1-oxopropan-2-yl)-2-methylpropanamide | 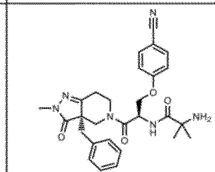 | 1.37 | 517.2 | (M+H)+ | A | QC1 |
| 21 | 2-amino-N-((R)-1-((R)-3a-benzyl-2-(2,2-difluoroethyl)-3-oxo-3a,4,6,7-tetrahydro-2H-pyrazolo[4,3-c]pyridin-5(3H)-yl)-1-oxo-3-phenoxypropan-2-yl)-2-methylpropanamide | 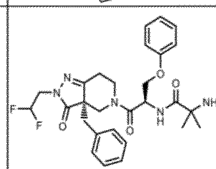 | 1.54 | 542.3 | (M+H)+ | A | QC1 |
| 22 | 2-amino-N-((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-1-oxo-3-phenoxypropan-2-yl)-2-methylpropanamide | 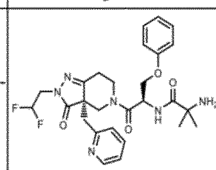 | 1.38 | 541.2 | (M-H)- | A | QC1 |
| 23 | 2-amino-N-((R)-3-(2-chlorophenoxy)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-1-oxopropan-2-yl)-2-methylpropanamide | 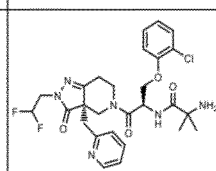 | 1.46 | 577 | (M+H)+ | A | QC1 |
| 24 | 2-amino-N-((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-3-(2-fluorophenoxy)-1-oxopropan-2-yl)-2-methylpropanamide | 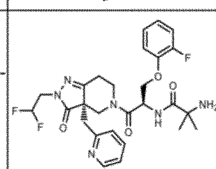 | 1.39 | 559.2 | (M-H)- | A | QC1 |
| 25 | 2-amino-N-((R)-3-(3-chlorophenoxy)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-1-oxopropan-2-yl)-2-methylpropanamide | 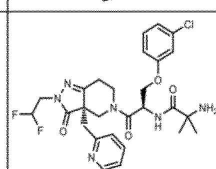 | 1.50 | 577 | (M+H)+ | A | QC1 |
| 26 | 2-amino-N-((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-3-(3-methoxyphenoxy)-1-oxopropan-2-yl)-2-methylpropanamide | 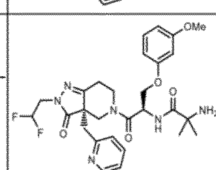 | 1.39 | 573.1 | (M+H)+ | A | QC1 |
| 27 | 2-amino-N-((R)-1-((R)-2-(2,2-difluoroethyl)-3-oxo-3a-(pyridin-2-ylmethyl)-3a,4,6,7-tetrahydro-2H-pyrazolo[4,3-c]pyridin-5(3H)-yl)-3-(3-fluorophenoxy)-1-oxopropan-2-yl)-2-methylpropanamide | 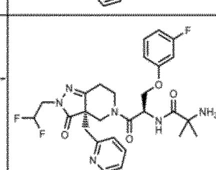 | 1.41 | 559.4 | (M-H)- | A | QC1 |
| 28 | 2-amino-N-((R)-1-((R)-3a-benzyl-2-methyl-3-oxo-3a,4,6,7-tetrahydro-2H-pyrazolo[4,3-c]pyridin-5(3H)-yl)-3-(4-fluorophenoxy)-1-oxopropan-2-yl)-2-methylpropanamide | 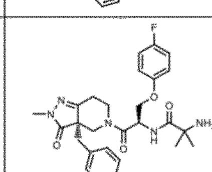 | 1.44 | 510.8 | (M+H)+ | A | QC1 |

In Column 99, Line 1 to Column 106, Line 62, Table 6,

| Example | Name | Structure | tR (min) | m/z | Ion mode | Condition | Method |
|---|---|---|---|---|---|---|---|
| 1 | 2-amino-N-((R)-1-((R)-3a-benzyl-2-methyl-3-oxo-3a,4,6,7-tetrahydro-2H-pyrazolo[4,3-c]pyridin-5(3H)-yl)-1-oxo-4-phenoxybutan-2-yl)-2-methylpropanamide | 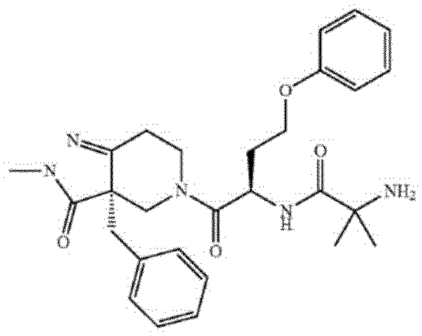 | 1.47 | 506.3 | (M + H)+ | A | QC1 |
| 2 | 2-amino-N-((R)-1-((R)-3a-benzyl-2-methyl-3-oxo-3a,4,6,7-tetrahydro-2H-pyrazolo[4,3-c]pyridin-5(3H)-yl)-4-(3,4-difluorophenoxy)-1-oxobutan-2-yl)-2-methylpropanamide | 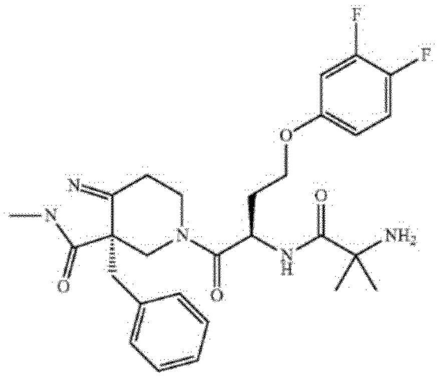 | 1.54 | 542.2 | (M + H)+ | B | QC1 |
| 3 | 2-amino-N-((R)-1-((R)-3a-benzyl-2-methyl-3-oxo-3a,4,6,7-tetrahydro-2H-pyrazolo[4,3-c]pyridin-5(3H)-yl)-4-(3,5-bis(trifluoromethyl)phenoxy)-1-oxobutan-2-yl)-2-methylpropanamide | 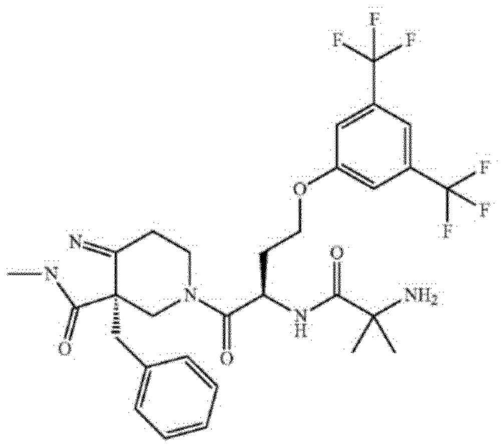 | 1.80 | 642.3 | (M + H)+ | B | QC1 |
| 4 | 2-amino-N-((R)-1-((R)-3a-benzyl-2-methyl-3-oxo-3a,4,6,7-tetrahydro-2H-pyrazolo[4,3-c]pyridin-5(3H)-yl)-4-(4-fluorophenoxy)-1-oxobutan-2-yl)-2-methylpropanamide | 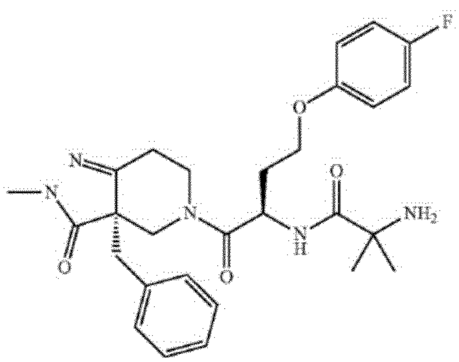 | 1.50 | 524.3 | (M + H)+ | B | QC1 |

| Example | Name | Structure | tR (min) | m/z | Ion mode | Condition | Method |
|---|---|---|---|---|---|---|---|
| 5 | 2-amino-N-((R)-1-((R)-3a-benzyl-2-methyl-3-oxo-3a,4,6,7-tetrahydro-2H-pyrazolo[4,3-c]pyridin-5(3H)-yl)-4-((5-fluoro-pyridin-3-yl)oxy)-1-oxobutan-2-yl)-2-methyl-propanamide | 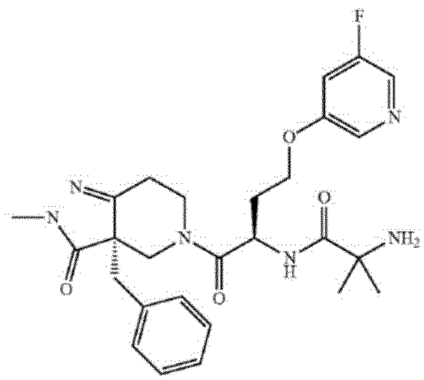 | 1.28 | 523.3 | (M − H)⁻ | B | QC1 |
| 6 | 2-amino-N-((R)-1-((R)-3a-benzyl-2-methyl-3-oxo-3a,4,6,7-tetrahydro-2H-pyrazolo[4,3-c]pyridin-5(3H)-yl)-4-(3-cyano-phenoxy)-1-oxobutan-2-yl)-2-methylpropanamide | 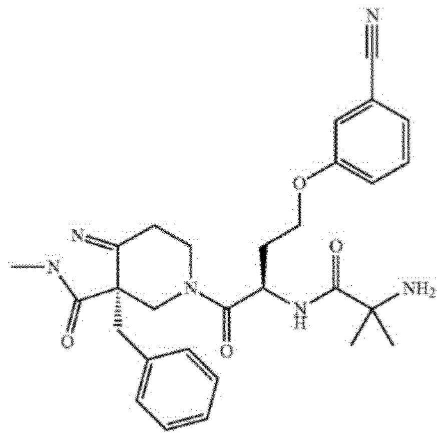 | 1.43 | 528.4 | (M − H)⁻ | A | QC1 |

"

should read

TABLE 6

| Example | Name | Structure | tR (min) | m/z | Ion mode | Condition | Method |
|---|---|---|---|---|---|---|---|
| 1 | 2-amino-N-((R)-1-((R)-3a-benzyl-2-methyl-3-oxo-3a,4,6,7-tetrahydro-2H-pyrazolo[4,3-c]pyridin-5(3H)-yl)-1-oxo-4-phenoxybutan-2-yl)-2-methylpropanamide | 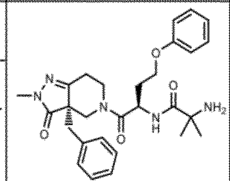 | 1.47 | 506.3 | (M+H)+ | A | QC1 |
| 2 | 2-amino-N-((R)-1-((R)-3a-benzyl-2-methyl-3-oxo-3a,4,6,7-tetrahydro-2H-pyrazolo[4,3-c]pyridin-5(3H)-yl)-4-(3,4-difluorophenoxy)-1-oxobutan-2-yl)-2-methylpropanamide | 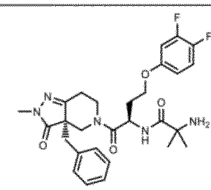 | 1.54 | 542.2 | (M+H)+ | B | QC1 |
| 3 | 2-amino-N-((R)-1-((R)-3a-benzyl-2-methyl-3-oxo-3a,4,6,7-tetrahydro-2H-pyrazolo[4,3-c]pyridin-5(3H)-yl)-4-(3,5-bis(trifluoromethyl)phenoxy)-1-oxobutan-2-yl)-2-methylpropanamide | 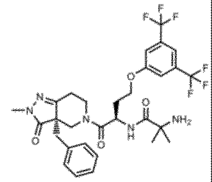 | 1.80 | 642.3 | (M+H)+ | B | QC1 |
| 4 | 2-amino-N-((R)-1-((R)-3a-benzyl-2-methyl-3-oxo-3a,4,6,7-tetrahydro-2H-pyrazolo[4,3-c]pyridin-5(3H)-yl)-4-(4-fluorophenoxy)-1-oxobutan-2-yl)-2-methylpropanamide | 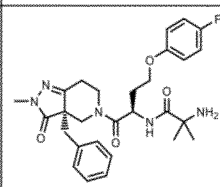 | 1.50 | 524.3 | (M+H)+ | B | QC1 |
| 5 | 2-amino-N-((R)-1-((R)-3a-benzyl-2-methyl-3-oxo-3a,4,6,7-tetrahydro-2H-pyrazolo[4,3-c]pyridin-5(3H)-yl)-4-((5-fluoropyridin-3-yl)oxy)-1-oxobutan-2-yl)-2-methylpropanamide | 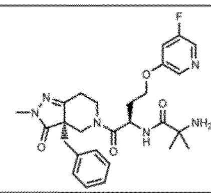 | 1.28 | 523.3 | (M-H)- | B | QC1 |
| 6 | 2-amino-N-((R)-1-((R)-3a-benzyl-2-methyl-3-oxo-3a,4,6,7-tetrahydro-2H-pyrazolo[4,3-c]pyridin-5(3H)-yl)-4-(3-cyanophenoxy)-1-oxobutan-2-yl)-2-methylpropanamide | 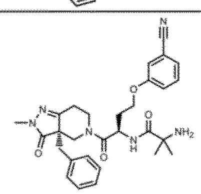 | 1.43 | 529.4 | (M-H)- | A | QC1 |

In Column 106, in Table 7, Line 13,
"Example 18  Comparative Example 6  12.6" should read
--Example 18  Comparative Example 6  12.8--.